United States Patent
Gradl et al.

(10) Patent No.: US 12,427,153 B2
(45) Date of Patent: Sep. 30, 2025

(54) 1,2,4-TRIAZIN-3(2H)-ONE COMPOUNDS FOR THE TREATMENT OF HYPERPROLIFERATIVE DISEASES

(71) Applicants: BAYER AKTIENGESELLSCHAFT, Leverkusen (DE); THE BROAD INSTITUTE, INC., Cambridge, MA (US)

(72) Inventors: Stefan Nikolaus Gradl, Berlin (DE); Manuel Ellermann, Berlin (DE); Philip Lienau, Berlin (DE); Charlotte Christine Kopitz, Falkensee (DE); Martin Lange, Berlin (DE); Adrian Tersteegen, Wuppertal (DE); Detlev Sülzle, Berlin (DE); Timothy A. Lewis, Cambridge, MA (US); Heidi Greulich, Cambridge, MA (US); Xiaoyun Wu, Cambridge, MA (US)

(73) Assignees: Bayer Aktiengesellschaft, Leverkusen (DE); The Broad Institute, Inc., Cambridge, MA (US)

( * ) Notice: Subject to any disclaimer, the term of this patent is extended or adjusted under 35 U.S.C. 154(b) by 792 days.

(21) Appl. No.: 17/389,940

(22) Filed: Jul. 30, 2021

(65) Prior Publication Data
US 2021/0353630 A1    Nov. 18, 2021

Related U.S. Application Data

(63) Continuation of application No. PCT/EP2020/052287, filed on Jan. 30, 2020.

(60) Provisional application No. 62/800,126, filed on Feb. 1, 2019.

(51) Int. Cl.
| | | |
|---|---|---|
| A61K 31/53 | (2006.01) | |
| A61P 35/00 | (2006.01) | |
| C07D 253/06 | (2006.01) | |
| C07D 403/10 | (2006.01) | |
| C07D 403/12 | (2006.01) | |

(52) U.S. Cl.
CPC ............. *A61K 31/53* (2013.01); *A61P 35/00* (2018.01); *C07D 253/06* (2013.01); *C07D 403/10* (2013.01); *C07D 403/12* (2013.01)

(58) Field of Classification Search
CPC ....... A61K 31/53; A61P 35/00; C07D 253/06; C07D 403/10; C07D 403/12
USPC .................................................... 514/210.2
See application file for complete search history.

(56) References Cited

U.S. PATENT DOCUMENTS

| | | | |
|---|---|---|---|
| 4,052,395 A | 10/1977 | Jojima et al. | |
| 4,158,094 A | 6/1979 | Niznik | |
| 4,334,030 A | 6/1982 | Kochanowski | |
| 4,423,045 A | 12/1983 | Brown et al. | |
| 4,493,835 A | 1/1985 | Hargreaves et al. | |
| 4,495,185 A | 1/1985 | Brown et al. | |
| 4,503,054 A | 3/1985 | Brown et al. | |
| 4,584,298 A | 4/1986 | Brown et al. | |
| 4,616,015 A * | 10/1986 | Teraji | C07D 253/06 544/182 |
| 4,624,951 A | 11/1986 | Goschke | |
| 4,629,789 A | 12/1986 | Gainer et al. | |
| 4,694,005 A | 9/1987 | Brown et al. | |
| 4,906,628 A | 3/1990 | Coates | |
| 4,933,336 A | 6/1990 | Martin et al. | |
| 5,552,409 A | 9/1996 | Michelotti et al. | |
| 8,501,731 B2 | 8/2013 | Hu et al. | |
| 9,212,146 B2 | 12/2015 | Hu et al. | |
| 9,549,932 B2 | 1/2017 | Wortmann et al. | |
| 10,287,353 B2 | 5/2019 | Bissonnette et al. | |
| 10,385,131 B2 | 8/2019 | Bissonnette et al. | |
| 10,729,680 B2 | 8/2020 | Lücking et al. | |
| 11,427,553 B2 | 8/2022 | Ellermann et al. | |
| 11,773,070 B2 | 10/2023 | Ellermann et al. | |
| 2016/0287604 A1 | 10/2016 | Wortmann et al. | |

(Continued)

FOREIGN PATENT DOCUMENTS

| | | |
|---|---|---|
| DE | 19929787 A1 | 1/2001 |
| EP | 86301 A1 | 12/1981 |

(Continued)

OTHER PUBLICATIONS

Gavezzotti Acc. Chem Res. 1994, 27, 309-314 (Year: 1994).*

(Continued)

*Primary Examiner* — Yevgeny Valenrod

(74) *Attorney, Agent, or Firm* — Greenberg Traurig, LLP; Melissa Hunter-Ensor; Scott Goncher

(57) ABSTRACT

The present invention includes name compounds of general formula (I): (I) in which $R^1$, $R^2$, $R^3$ and $R^4$ are as defined herein, methods for their preparation, pharmaceutical compositions and combinations comprising said compounds, and their use for the treatment of hyperproliferative diseases.

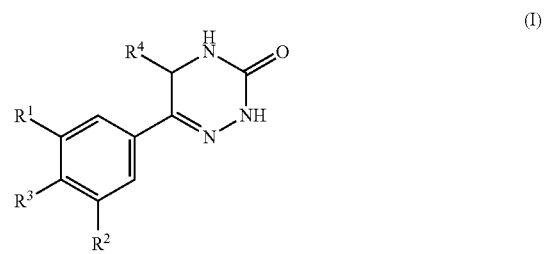

8 Claims, No Drawings

(56) References Cited

U.S. PATENT DOCUMENTS

| | | |
|---|---|---|
| 2020/0247783 A1 | 8/2020 | Ellermann et al. |
| 2020/0369633 A1 | 11/2020 | Ellermann et al. |
| 2021/371935 A1 | 12/2021 | Wu et al. |
| 2022/0396554 A1 | 12/2022 | Ellermann et al. |
| 2023/0017200 A1 | 1/2023 | Ellermann et al. |

FOREIGN PATENT DOCUMENTS

| | | |
|---|---|---|
| EP | 52442 A1 | 5/1982 |
| EP | 0059688 A1 | 9/1982 |
| EP | 80296 A1 | 1/1983 |
| EP | 122494 A2 | 10/1984 |
| EP | 122627 A2 | 10/1984 |
| EP | 123254 A1 | 10/1984 |
| EP | 0175363 A2 | 3/1986 |
| EP | 0220044 A2 | 4/1987 |
| EP | 0478195 A1 | 4/1992 |
| EP | 2253625 A1 | 11/2010 |
| EP | 2281822 A1 | 2/2011 |
| JP | H05148250 A | 6/1993 |
| JP | H07291968 A | 11/1995 |
| TW | 201613920 A | 4/2016 |
| WO | 1994001412 A1 | 1/1994 |
| WO | 2002072103 A1 | 9/2002 |
| WO | 2008108602 A1 | 9/2008 |
| WO | 2009114993 A1 | 9/2009 |
| WO | 2010/121022 A1 | 10/2010 |
| WO | 2011138427 A2 | 11/2011 |
| WO | 2012161812 A1 | 11/2012 |
| WO | 2014/164704 A2 | 10/2014 |
| WO | 2016020320 A1 | 2/2016 |
| WO | 2017027854 A1 | 2/2017 |
| WO | 2017134231 A1 | 8/2017 |
| WO | 2017/150654 A1 | 9/2017 |
| WO | 2020157194 A1 | 8/2020 |

OTHER PUBLICATIONS

Mohammed A. Dahab++, et al., "Thieme Chemistry Journals Awardees—Where Are They Now? A Cascade Synthesis of 1,2,4-Triazin-3(2H)-ones Using Nitrogen-Substituted Isocyanates," New York—Synlett 2017, vol. 28, pp. 456-460.

C.G.Wermuth, et al. "Molecular Variations Based on Isosteric Replacements", The Practice of Medicinal Chemistry, Elsevier, 2003, pp. 189-214.

Masakatsu Nozaki, et al., MedChem, 1rst, edition, Kagaku-Dojin Publishing Co. Inc. 1995, p. 98-99.

International Search Report and Written Opinion in International Application No. PCT/EP2020/052287, mailed on Mar. 31, 2020 (9 pages).

Forest et al., "A novel class of cardiotonic agents: synthesis and biological evaluation of 5-substituted 3,6-dihydrothiadiazin-2-ones with cyclic AMP phosphodiesterase inhibiting and myofibrillar calcium sensitizing properties," Journal of Medicinal Chemistry, 1992, vol. 35, No. 1, pp. 163-172.

Goeschke et al., "6-(4-Morpholino-phenyl)-4,5-dihydro-2H-pyridazine-3-ones: potent platelet aggregation inhibitors and antithrombotics," European Journal of Medicinal Chemistry, Oct. 1991, vol. 26, No. 7, pp. 715-721.

Hurd et al., "On Acylhydrazones and 1,2,3-Thiadiazoles," Journal of the American Chemical Society, 1955, vol. 77, No. 20, pp. 5359-5364.

James, Christopher W., "Anagrelide-Induced Cardiomyopathy," Pharmacotherapy, 2012, vol. 20, No. 10, pp. 1224-1227.

King, Frank D., "Bioisosteres, Conformational Restriction, and Pro-drugs—Case History: An Example of a Conformational Restriction Approach," Medical Chemistry: Principles and Practice, 1994, Chapter 14, pp. 206-208.

Maurice et al., "Advances in targeting cyclic nucleotide phosphodiesterases," Nature Reviews Drug Discovery, 2014, vol. 13, No. 4, pp. 290-314.

Movesian et al., "Phosphodiesterase Inhibition in Heart Failure," Phosphodiesterases as Drug Targets, Handbook of Experimental Pharmacology, 2011, vol. 204, pp. 237-249.

Packer et al., "Effect of Oral Milrinone on Mortality in Severe Chronic Heart Failure," The New England Journal of Medicine, Nov. 21, 1991, vol. 325, pp. 1468-1475.

Page II et al., "Drugs That May Cause or Exacerbate Heart Failure," Circulation, 2016, vol. 134, No. 6, pp. e32-e69.

Rosenblum et al., "Synthesis of Dihydrooxadiazinones and Study of Geometrical Isomerism in α-Ketol Carbethoxyhydrazones," Journal of the American Chemical Society, 1963, vol. 85, No. 23, pp. 3874-3878.

Rosenblum et al., "The Chemistry of 1,3,4 Oxadiazin-2-ones. Preparation and Thermal Stability," Journal of the American Chemical Society, 1965, vol. 87, No. 24, pp. 5716-5719.

Rosenblum et al., "Thermal Decomposition of 2,3-Dihydro-5,6-Diphenyl-1,3,-4,6-Oxadiazin-2-one," Chemistry & Industry, Dec. 15, 1956, pp. 1480-1481.

Savai et al., "Targeting cancer with phosphodiesterase inhibitors," Expert Opinion on Investigational Drugs, 2010, vol. 19, No. 1, pp. 117-131.

Steck et al., "Pyridazines. VI. Some 6-Substituted 3(2H)pyridazinones," Journal of Heterocyclic Chemistry, Oct. 1974, vol. 11, No. 5, pp. 755-761.

Burger, Alfred, "Isosterism and bioisosterism in drug design," Progress in Drug Research, 1991, pp. 287-371.

Wuts, Peter G. M., "Protection for the Amino Acid Group," Greene's Protective Groups in Organic Synthesis, Fifth Edition, 2014, Chapter 7, pp. 907-1193.

Matthews et al., "Dominant-Negative Activator Protein 1 (TAM67) Targets Cyclooxygenase-2 and Osteopontin under Conditions in which It Specifically Inhibits Tumorigenesis," Cancer Research, Mar. 15, 2007, vol. 67, No. 6, pp. 2430-2438.

* cited by examiner

1,2,4-TRIAZIN-3(2H)-ONE COMPOUNDS FOR THE TREATMENT OF HYPERPROLIFERATIVE DISEASES

CROSS-REFERENCE TO RELATED APPLICATIONS

This application is a continuation of PCT International Application No. PCT/EP2020/052287, filed Jan. 30, 2020, designating the United States and published in English, which claims the benefit of U.S. Provisional Application No. 62/800,126, filed Feb. 1, 2019, the entire contents of each of which are incorporated herein by reference.

The present invention includes triazine-3(2H)-one compounds of general formula (I) as described and defined herein, methods for their preparation and intermediates, pharmaceutical compositions, combinations comprising said compounds, and their use.

BACKGROUND

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by predictive chemogenomics to identify the cell features associated with drug response. In the 1990s, Weinstein and colleagues demonstrated that the cytotoxic profile of a compound can be used to identify cellular characteristics, such as gene-expression profiles and DNA copy number, which correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small molecule sensitivity can be linked to expression patterns or somatic alterations, as in the case of trastuzumab-sensitive HER2-amplified breast cancer or erlotinib-sensitive EGFR-mutant lung cancer.

Phenotypic screening identified some of the compounds known in the literature to be PDE3 inhibitors to be useful for the treatment of certain cancers. Co-expression of PDE3A and/or PDE3B and Schlafen 12 (SLFN12) polynucleotides or polypeptides are typically required for cells to be sensitive. PDE3A and/or B inhibitors which cause drug sensitivity have been found to stabilize the formation of a complex between PDE3A and/or PDE3B and SLFN12. PDE3A and/or B inhibitors which do not cause inhibition of tumor cell proliferation typically do not stabilize the PDE3A- and/or PDE3B-SLFN12 complex.

Some triazinone derivatives are known, especially in the context of treatment of cardiovascular diseases: JP 07291968 A 19951107 (1995) U.S. Pat. No. 4,616,015 (EP0122627), EP0052442, EP0080296, EP0123254, EP 0122627, EP0122494,

SUMMARY

It has now been found, and this constitutes at least in part one basis of the present invention, that the compounds of the present invention have surprising and advantageous properties.

In particular, the compounds of the present invention have surprisingly been found to inhibit tumor cell proliferation with $IC_{50}$ values of <100 nM in e.g. HeLa cells. Additionally, the compounds do not inhibit enzymatic PDE3A and/or PDE3B at the concentration at which they inhibit tumor cell proliferation but at concentrations where $IC_{50}$ values for enzymatic PDE3A and/or PDE3B inhibition may be >10 times higher than $IC_{50}$ values for tumor cell proliferation. Without wishing to be bound by theory, this distinction in inhibitory properties may be associated with PDE3A and/or PDE3B-SLFN12 complex induction and/or improved pharmacokinetic parameters in vitro or in vivo and/or improved physicochemical properties and/or improved safety pharmacological properties. With these advantageous properties, the compounds described herein may therefore be used for the treatment or prophylaxis of hyperproliferative diseases, such as cancer diseases.

The present invention provides compounds of general formula (I) which modulate formation of a PDE3A-SLFN12 complex and/or PDE3B-SLFN12 complex, methods for their preparation, pharmaceutical composition and the use thereof and methods of treatment or prophylaxis of diseases, in particular of hyperproliferative diseases more particularly of cancer diseases. These and other features of the present teachings are set forth herein.

In accordance with a first aspect, the present invention includes compounds of general formula (I):

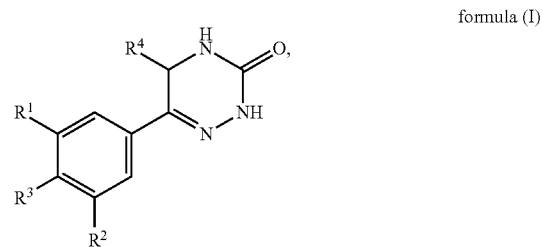

formula (I)

wherein
$R^1$ is a hydrogen atom, a halogen atom, a $C_1$-$C_3$-alkyl group, a $C_1$-$C_3$-haloalkyl group;
$R^2$ is a hydrogen atom, a halogen atom;
with the proviso that both, $R^1$ and $R^2$, may not be a hydrogen atom at the same time with the exception if $R^3$ is an ortho substituted phenyl group, both, $R^1$ and $R^2$, may also be a hydrogen atom;
$R^3$ is
a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group,
a $C_2$-$C_6$-alkenyl group, which is optionally substituted with a $C_1$-$C_3$-alkoxy group,
a $C_5$-$C_6$-cycloalkenyl group,
a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

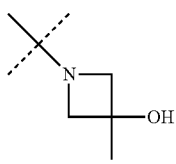

group, a

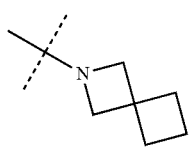

group, a

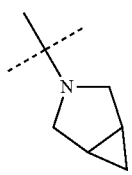

group, a 5- to 10-membered heteroaryl group which is substituted one or more times with a group independently selected from an amino group, a halogen atom, and a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

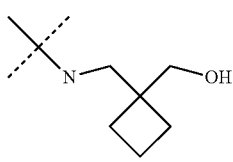

group, $R^4$ is a hydrogen atom or a $C_1$-$C_3$-alkyl group;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

Another aspect of the invention is the use of the compounds of formula (I)

wherein $R^1$ is a hydrogen atom, a halogen atom, a $C_1$-$C_3$-alkyl group, a $C_1$-$C_3$-haloalkyl group;

$R^2$ is a hydrogen atom, a halogen atom;

$R^3$ is a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

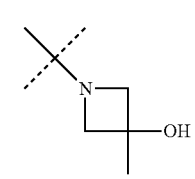

group, a

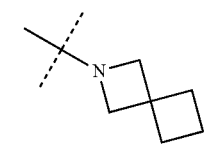

group, a

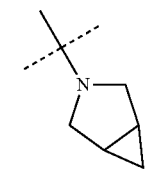

group, a 5- to 10-membered heteroaryl group which is substituted one or more times with a group independently selected from an amino group, a halogen atom, and a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group;
a $NR^5R^6$ group, and
a

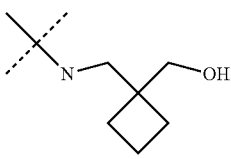

group, $R^4$ is a hydrogen atom or a $C_1$-$C_3$-alkyl group;
$R^5$ is a hydrogen atom
$R^6$ is selected from
   a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and
   a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same,
for the treatment of hyperproliferative diseases, particularly cancer, more particularly brain cancer, cervical cancer, a skin cancer and an ovarian cancer.

DETAILED DESCRIPTION

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.
Structures drawn include all permissible rotations about bonds.

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, or 3, in particular 1, or 2.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one substituent.

As used herein, an oxo substituent represents an oxygen atom, which is bound to a carbon atom or to a sulfur atom via a double bond.

The terms "oxo", "an oxo group" or "an oxo substituent" mean a doubly attached oxygen atom =O. Oxo may be attached to atoms of suitable valency, for example to a saturated carbon atom or to a sulfur atom. For example, but without limitation, one oxo group can be attached to a carbon atom, resulting in the formation of a carbonyl group C(=O), or two oxo groups can be attached to one sulfur atom, resulting in the formation of a sulfonyl group —S(=O)$_2$.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of.

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The term "halogen atom" means a fluorine, chlorine, bromine or iodine atom, particularly a fluorine, or chlorine atom except where halogen is intended to be a leaving group.

The term "$C_1$-$C_6$-alkyl-" means a linear or branched, saturated hydrocarbon group having 1, 2, 3, 4, 5, or 6, carbon atoms, such as, for example, a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-group, or an isomer thereof. Particularly, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or a tert-butyl-group, 1, 2 or 3 carbon atoms ("$C_1$-$C_3$-alkyl-"), e.g., a methyl-, ethyl-, n-propyl- or a iso-propyl group, or 1 or 2 carbon atoms ("$C_1$-$C_2$-alkyl-"), e.g., a methyl group or an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_1$-$C_3$-hydroxyalkyl" means a linear or branched, saturated, monovalent hydrocarbon group in which the term "$C_1$-$C_6$-alkyl" is defined supra, and in which 1, 2 or 3 hydrogen atoms are replaced with a hydroxy group, such as, for example, a hydroxymethyl-, 1-hydroxyethyl-, 2-hydroxyethyl-, 1,2-dihydroxyethyl-, 3-hydroxypropyl-, 2-hydroxypropyl-, 1-hydroxypropyl-, 1-hydroxypropan-2-yl-, 2-hydroxypropan-2-yl-, 2,3-dihydroxypropyl-, 1,3-dihydroxypropan-2-yl-, group.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, a fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group. Particularly haloalkyl is trifluoromethyl or difluoromethyl.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, such as, for example, a methoxy-, ethoxy-, n-propoxy-, isopropoxy-, n-butoxy-, sec-butoxy-, isobutoxy-, tert-butoxy-, pentyloxy-, isopentyloxy or a n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, a fluoromethoxy-, difluoromethoxy-, trifluoromethoxy-, 2,2,2-trifluoroethoxy- or a pentafluoroethoxy group.

The term "$C_2$-$C_6$-alkenyl" means a linear or branched, monovalent hydrocarbon group, which contains one or two double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then it is possible for said double bonds to be isolated from, or conjugated with, each other. Said alkenyl group is, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- or a 1-(1,1-dimethylethyl-)ethenyl group.

The same definitions can be applied should the alkenyl group be placed within a chain as a bivalent "$C_1$-$C_6$-alkenylene" moiety. All names as mentioned above then will bear a "ene" added to their end, thus e.g., a "pentenyl" becomes a bivalent "pentenylene" group.

The term "$C_3$-$C_6$-cycloalkyl-" means a saturated monocyclic or bicyclic hydrocarbon ring which contains 3, 4, 5, or 6, carbon atoms ("$C_3$-$C_6$-cycloalkyl-"). Said $C_3$-$C_6$-cycloalkyl-group may be, for example, a monocyclic hydrocarbon ring, such as, for example, a cyclopropyl-, cyclobutyl-, cyclopentyl-, or a cyclohexyl-ring. Particularly, said hydrocarbon ring is monocyclic and contains 3, 4, 5, or 6 carbon atoms ("$C_3$-$C_6$-cycloalkyl-"), such as, for example, a cyclopropyl-, cyclobutyl-, cyclopentyl-, or a cyclohexyl ring. A cycloalkyl group may be optionally substituted as defined at the respective part wherein such term is used.

The term "$C_5$-$C_6$-cycloalkenyl" means a monovalent, mono- or bicyclic hydrocarbon ring which contains 5, or 6, carbon atoms and one double bond. Said $C_5$-$C_6$-cycloalkenyl group is for example, a monocyclic hydrocarbon ring, such as, for example, a cyclopentenyl-, or a cyclohexenyl-, group. More particularly the cycloalkenyl group is a $C_5$-$C_6$-cycloalkenyl group.

The term "4- to 6-membered heterocycloalkyl" mean a monocyclic, saturated or partially unsaturated heterocycle with 4, 5, or 6, ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as, for example, a azetidinyl-, oxetanyl- or thietanyl group; or a 5-membered ring, such as a tetrahydrofuranyl-, 1,3-dioxolanyl-, thiolanyl-, pyrrolidinyl-, imidazolidinyl-, pyrazolidinyl-, 1,1-dioxidothiolanyl-, 1,2-oxazolidinyl-, 1,3-oxazolidinyl- or a 1,3-thiazolidinyl group, for example; or a 6-membered ring, such as, for example, a tetrahydropyranyl-, tetrahydrothiopyranyl-, piperidinyl-, morpholinyl-, dithianyl-, thiomorpholinyl-, piperazinyl-, 1,3-dioxanyl-, 1,4-dioxanyl- or a 1,2-oxazinanyl group, for example.

The term "aryl" means a phenyl-, naphthyl-, 5,6-dihydronaphthyl-, 7,8-dihydronaphthyl-, 5,6,7,8-tetrahydronaphthyl-, an indanyl-, or an indenyl group, which is unsubstituted or substituted with one, two, three, four or five substituents, each substituent independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $C_1$-$C_3$-halothioalkyl group, a $C_3$-$C_6$-cycloalkyl group, particularly a halogen atom, a $C_1$-$C_3$-alkyl group, a $C_1$-$C_3$-haloalkyl group, a $C_1$-$C_3$-alkoxy group, and a $C_1$-$C_3$-haloalkoxy group. Particularly "aryl" is phenyl. Furthermore an "ortho substituted phenyl group $R^3$" as used in the proviso for $R^3$ is meant to be a phenyl group which bears a substitutent directly on the subsequent carbon atom to the bond by which the phenyl substitutent $R^3$ is linked to the rest of the molecule.

The term "heteroaryl" means a monovalent, monocyclic, bicyclic or tricyclic aromatic ring having 5, 6, 8, 9, or 10, ring atoms (a "5- to 10-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl-group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group; or a tricyclic heteroaryl group, such as, for example, a carbazolyl-, acridinyl- or a phenazinyl group; or a 9-membered heteroaryl group, such as, for example, a benzofuranyl-, benzothienyl-, benzoxazolyl-, benzisoxazolyl-, benzimidazolyl-, benzothiazolyl-, benzotriazolyl-, indazolyl-, indolyl-, isoindolyl-, indolizinyl- or a purinyl group.

In general, and unless otherwise mentioned, the heteroaryl or heteroarylene groups include all possible isomeric forms thereof, for example: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_6$, $C_1$-$C_6$ particularly $C_1$-$C_2$, $C_1$-$C_3$, $C_1$-$C_4$, $C_1$-$C_6$, $C_1$-$C_6$; more particularly $C_1$-$C_4$; in the case of "$C_1$-$C_6$-haloalkyl-" or "$C_1$-$C_6$-haloalkoxy-" even more particularly $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl-group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_6$, $C_3$-$C_4$, $C_2$-$C_3$, $C_2$-$C_4$, $C_2$-$C_5$ particularly $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl-group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_6$, $C_3$-$C_4$, $C_4$-$C_6$, $C_5$-$C_7$; particularly $C_3$-$C_6$.

As used herein, the term "leaving group" means an atom or a group of atoms that is displaced in a chemical reaction as stable species taking with it the bonding electrons. In particular, such a leaving group is selected from the group comprising: halide, in particular a chloro-, bromo- or iodo group, a (methylsulfonyl)oxy-, [(4-methylphenyl)sulfonyl]oxy-, [(trifluoromethyl)sulfonyl]oxy-, [(nona-fluorobutyl)sulfonyl]oxy-, [(4-bromophenyl)sulfonyl]oxy-, [(4-nitrophenyl)sulfonyl]oxy-, [(2-nitrophenyl)sulfonyl]oxy-, [(4-isopropylphenyl)sulfonyl]oxy-, [(2,4,6-triisopropylphenyl)sulfonyl]oxy-, [(2,4,6-trimethylphenyl)sulfonyl]oxy-, [(4-tert-butylphenyl)sulfonyl]oxy-, (phenylsulfonyl)oxy- and a [(4-methoxyphenyl)-sulfonyl]oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis,* $4^{th}$ edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc. and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

An "oxo" substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the diseases specified herein the isotopic variant(s) of the compounds of general formula (I) particularly contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, particularly for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron Letters, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1995; J. Atzrodt et al., Angew. Chem., Int. Ed. 2007, 46, 7744; K. Matoishi et al., Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, particularly higher than 90%, 95%, 96% or 97%, even more particularly higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol.

Pharmacol., 1999, 77, 79). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity should they be different for the isomers. These separated, pure or partially purified isomers or racemic mixtures of the compounds of this invention are also included within the scope of the present invention. The purification and the separation of such materials can be accomplished by standard techniques known in the art including chiral high pressure liquid chromatography (HPLC), the formation and crystallization of chiral salts, or prepared by asymmetric syntheses.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention can be achieved by any suitable state of the art method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

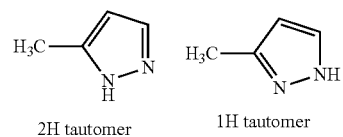

2H tautomer     1H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as hydrochloric acid, hydrobromic acid, hydroiodic acid, sulfuric acid, bisulfuric acid, phosphoric acid, and nitric acid or with an organic acid, such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)-benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonate acid, itaconic acid, sulfamic acid, trifluoromethanesulfonic acid, dodecylsulfuric acid, ethansulfonic acid, benzenesulfonic acid, para-toluenesulfonic acid, methansulfonic acid, 2-naphthalenesulfonic acid, naphthalenedisulfonic acid, camphorsulfonic acid acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid and thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) or an aluminium salt or a zinc salt, or an ammonium salt derived from ammonia or from an organic primary, secondary or tertiary amine having 1 to 20 carbon atoms, such as by way of example and by preference, ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methylglucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol.

Additionally, the compounds according to the invention may form salts with a quaternary ammonium ion obtainable, e.g., by quaternisation of a basic nitrogen-containing group with agents such as lower alkylhalides, such as alkylchlorides, e.g. methylchloride, ethylchloride, propylchloride and butylchloride; such as alkylbromides, e.g. methylbromide, ethylbromide, propylbromide and butylbromide; and such as alkyliodides; e.g. methyliodide, ethyliodide, propyliodide and butyliodide; dialkylsulfates such as dimethylsulfate, diethylsulfate, dibutylsulfate and diamylsulfates, long chain halides such as e.g. decylchloride, laurylchloride, myristylchloride and stearylchloride, decylbromide, laurylbromide, myristylbromide and stearylbromide, decyliodide, lauryliodide, myristyliodide and stearyliodide, aralkylhalides such as benzylchloride, benzylbromide, benzyliodide and phenethylbromides and others. Examples of suitable quaternary ammonium ions are tetramethylammonium, tetraethylammonium, tetra(n-propyl)ammonium, tetra(n-butyl)ammonium, or N-benzyl-N,N,N-trimethylammonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

DESCRIPTION

In accordance with a first aspect, the present invention includes compounds of general formula (I), supra,

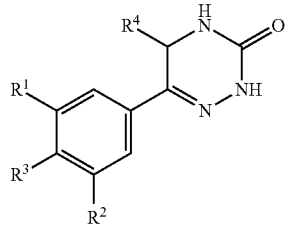

formula (I)

in which:
R$^1$ is a hydrogen atom, a halogen atom, a C$_1$-C$_3$-alkyl group, or a C$_1$-C$_3$-haloalkyl group;
R$^2$ is a hydrogen atom, or a halogen atom;
with the proviso that both, R$^1$ and R$^2$, may not be a hydrogen atom at the same time with the exception if R$^3$ is an ortho substituted phenyl group, both, R$^1$ and R$^2$, may also be a hydrogen atom;
R$^3$ is selected from
  a C$_1$-C$_3$-alkyl group which is substituted one or more times with a group independently selected from a C$_1$-C$_3$-alkyl group, a C$_1$-C$_3$-alkoxy group, a heterocycloalkyl group, and a NR$^5$R$^6$ group,
  a C$_2$-C$_6$-alkenyl group, which is optionally substituted with a C$_1$-C$_3$-alkoxy group,
  a C$_5$-C$_6$-cycloalkenyl group,
  a phenyl group which is substituted one or more times with a group independently selected from halogen atom, C$_1$-C$_3$-alkyl group, and a C$_1$-C$_3$-haloalkyl group,
  a 4- to 6-membered heterocycloalkyl group which is substituted one or more times with a group independently selected from a fluorine atom, a hydroxy group, and a C$_1$-C$_3$-alkyl group, a

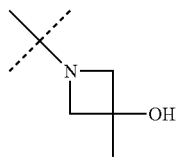

group, a

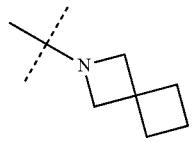

group, a

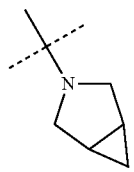

group,
a 5- to 10-membered heteroaryl group which is substituted one or more times with a group independently selected from an amino group, a halogen atom, a C$^1$-C$^3$-haloalkyl group group,
a C$_1$-C$_6$-alkoxy group which is optionally substituted with a group independently selected from C$_1$-C$_3$-haloalkyl group, a hydroxy group, a C$_1$-C$_3$-alkyoxy group, a C$_4$-C$_6$-cycloalkyl group, a 4- to 6-membered heterocycloalkyl group, a 5- to 6-membered heteroaryl group, with the proviso that an unsubstituted methoxy group is excluded;
a NR$^5$R$^6$ group, and
a

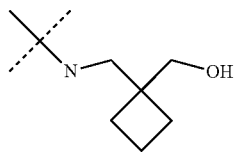

group,
R$^4$ is a hydrogen atom or a C$_1$-C$_3$-alkyl group;
R$^5$ is a hydrogen atom
R$^6$ is selected from
  a C$_1$-C$_3$-alkyl group which is substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group,
  and
  a C$_5$-C$_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with an embodiment of the first aspect the present invention includes compounds of general formula (I), supra, in which:

R¹ is a hydrogen atom, a halogen atom, a $C_1$-$C_3$-alkyl group, or a $C_1$-$C_3$-haloalkyl group;

R² is a hydrogen atom, or a halogen atom;

with the proviso that both, R¹ and R², may not be a hydrogen atom at the same time with the exception if R³ is an ortho substituted phenyl group, both, R¹ and R², may also be a hydrogen atom;

R³ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

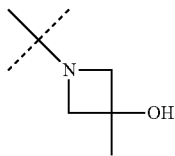

group, a

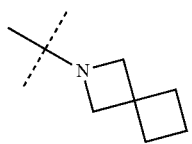

group, a

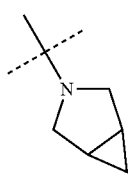

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

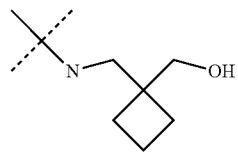

group,

R⁴ is a hydrogen atom or a $C_1$-$C_3$-alkyl group;

R⁵ is a hydrogen atom

R⁶ is selected from a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with an embodiment of the first aspect the present invention includes compounds of general formula (I), supra, in which:

R¹ is a hydrogen atom, a halogen atom, a $C_1$-$C_3$-alkyl group, or a $C_1$-$C_3$-haloalkyl group;

R² is a hydrogen atom, or a halogen atom;

with the proviso that both, R¹ and R², may not be a hydrogen atom at the same time with the exception if R³ is an ortho substituted phenyl group, both, R¹ and R², may also be a hydrogen atom;

R³ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

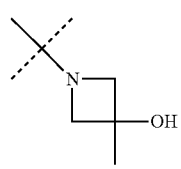

group, a

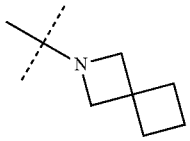

group, a

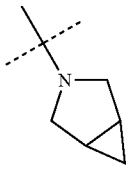

group, a 5- to 10-membered heteroaryl group which is substituted one or more times with a group independently selected from an amino group, a halogen atom, a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

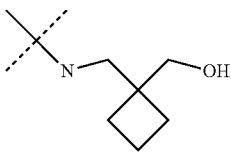

group, $R^4$ is a hydrogen atom;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with an embodiment of the first aspect the present invention includes compounds of general formula (I), supra,

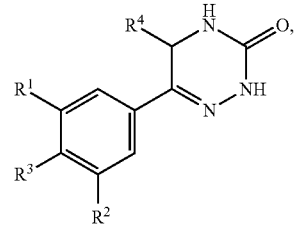

formula (I)

in which:

$R^1$ is a hydrogen atom, a halogen atom, a $C_1$-$C_3$-alkyl group, or a $C_1$-$C_3$-haloalkyl group;

$R^2$ is a hydrogen atom, or a halogen atom;

with the proviso that both, $R^1$ and $R^2$, may not be a hydrogen atom at the same time with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

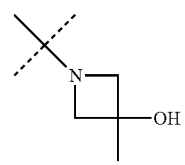

group, a

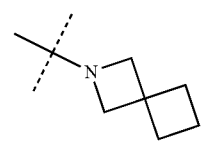

group, a

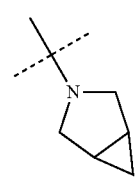

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

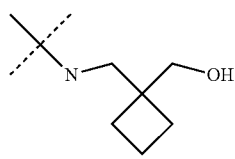

group, $R^4$ is a hydrogen atom;
$R^5$ is a hydrogen atom
$R^6$ is selected from
  a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and
  a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with an embodiment of the first aspect the present invention includes compounds of general formula (I), supra, in which:
$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
with the proviso that both, $R^1$ and $R^2$, may not be a hydrogen atom at the same time with the exception if $R^3$ is an ortho substituted phenyl group, both, $R^1$ and $R^2$, may also be a hydrogen atom;
$R^3$ is selected from
  a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group,
  a $C_2$-$C_6$-alkenyl group, which is substituted with a $C_1$-$C_3$-alkoxy group,
  a $C_5$-$C_6$-cycloalkenyl group,
  a phenyl group which is substituted one or more times with a group independently selected from halogen atom, $C_1$-$C_3$-alkyl group, and a $C_1$-$C_3$-haloalkyl group,
  a 4- to 6-membered heterocycloalkyl group which is substituted one or more times with a group independently selected from a fluorine atom, a hydroxy group, and a $C_1$-$C_3$-alkyl group, a

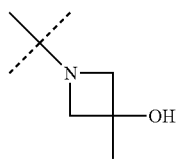

group, a

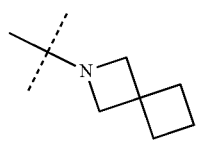

group, a

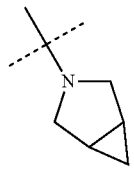

group,
a 5- to 10-membered heteroaryl group which is substituted one or more times with a group independently selected from an amino group, a halogen atom, a $C^1$-$C^3$-haloalkyl group,
a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;
a $NR^5R^6$ group, and
a

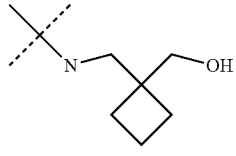

group,
$R^4$ is a $C_1$-$C_3$-alkyl group;
$R^5$ is a hydrogen atom
$R^6$ is selected from
  a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and
  a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with an embodiment of the first aspect the present invention includes compounds of general formula (I), supra,

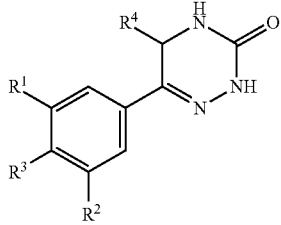

formula (I)

in which:

$R^1$ is a hydrogen atom, a halogen atom, a $C_1$-$C_3$-alkyl group, or a $C_1$-$C_3$-haloalkyl group;

$R^2$ is a hydrogen atom, or a halogen atom;

with the proviso that both, $R^1$ and $R^2$, may not be a hydrogen atom at the same time with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

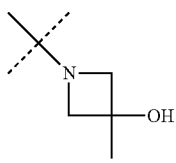

group, a

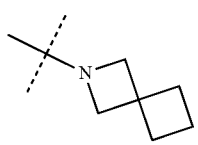

group, a

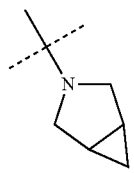

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

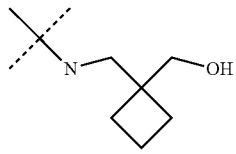

group, $R^4$ is a $C_1$-$C_3$-alkyl group;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, a $C_1$-$C_3$-haloalkyl group;

$R^2$ is a hydrogen atom, a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

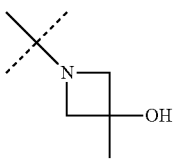

group, a

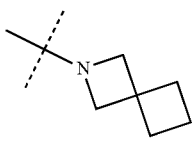

group, a

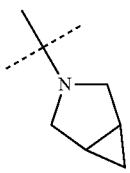

group, a 5- to 10-membered heteroaryl group which is substituted one or more times with a group independently selected from an amino group, a halogen atom, a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

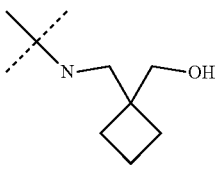

group, $R^4$ is a hydrogen atom or a $C_1$-$C_3$-alkyl group;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, a $C_1$-$C_3$-haloalkyl group;

$R^2$ is a hydrogen atom, a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

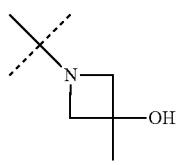

group, a

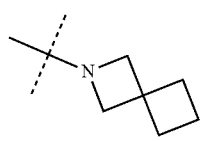

group, a

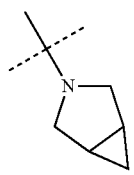

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

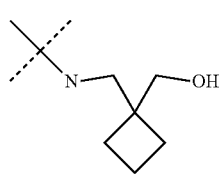

group, $R^4$ is a hydrogen atom or a $C_1$-$C_3$-alkyl group;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, a $C_1$-$C_3$-haloalkyl group;

$R^2$ is a hydrogen atom, a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

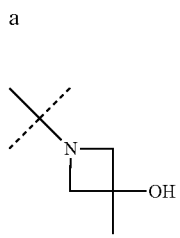

group, a

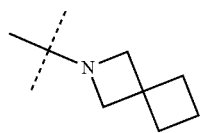

group, a

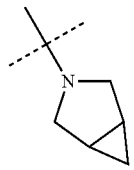

group, a 5- to 10-membered heteroaryl group which is substituted one or more times with a group independently selected from an amino group, a halogen atom, a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

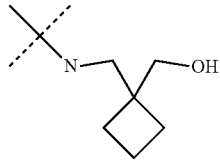

group, $R^4$ is a hydrogen atom;

$R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, or a $C_1$-$C_3$-haloalkyl group;

$R^2$ is a hydrogen atom, or a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

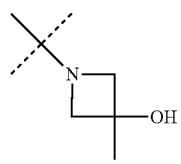

group, a

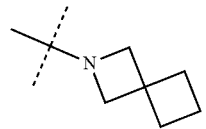

group, a

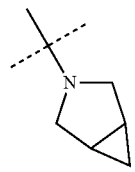

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

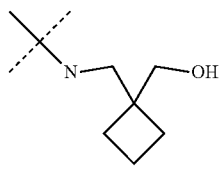

group, $R^4$ is a hydrogen atom;

$R^5$ is a hydrogen atom $R^6$ is selected from a $C_1$-$C_3$-alkyl group which is substituted one or more times with a group independently selected from a 5 to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, a $C_1$-$C_3$-haloalkyl group;

$R^2$ is a hydrogen atom, a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is selected from a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

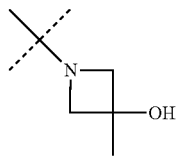

group, a

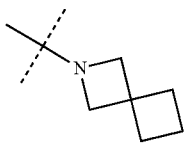

group, a

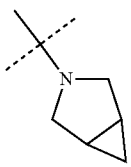

group, a 5- to 10-membered heteroaryl group which is substituted one or more times with a group independently selected from an amino group, a halogen atom, a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

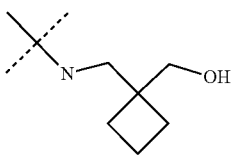

group, $R^4$ is a $C_1$-$C_3$-alkyl group $R^5$ is a hydrogen atom $R^6$ is selected from a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

$R^1$ is a hydrogen atom, a halogen atom, a $C_1$-$C_3$-alkyl group, or a $C_1$-$C_3$-haloalkyl group;

$R^2$ is a hydrogen atom, or a halogen atom;

with the proviso that both, $R^1$ and $R^2$, may not be a hydrogen atom at the same time, with the exception if $R^3$ is an ortho substituted phenyl group, both, $R^1$ and $R^2$, may also be a hydrogen atom;

$R^3$ is a $C_1$-$C_3$-alkyl group which is substituted one or more times with a group independently selected from a $C_1$-$C_3$-alkyl group, a $C_1$-$C_3$-alkoxy group, a heterocycloalkyl group, and a $NR^5R^6$ group, a $C_2$-$C_6$-alkenyl group, which is optionally substituted with a $C_1$-$C_3$-alkoxy group, a $C_5$-$C_6$-cycloalkenyl group, a phenyl group which is substituted one or more times with a group independently selected from halogen atom, $C_1$-$C_3$-alkyl group, a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

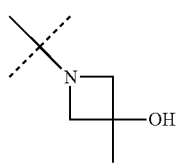

group, a

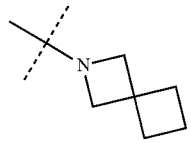

group, a

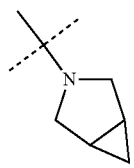

group, a 5- to 10-membered heteroaryl group which is substituted one or more times with a group independently selected from an amino group, a chlorine atom, a fluorine atom, a trifluormethyl group, and a difluoromethyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

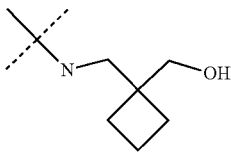

group,
$R^4$ is a $C_1$-$C_3$-alkyl group;
$R^5$ is a hydrogen atom
$R^6$ is selected from
  a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group,
  and
  a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:
$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
with the proviso that both, $R^1$ and $R^2$, may not be a hydrogen atom at the same time
$R^3$ is
  a phenyl group which is substituted one or more times with a group independently selected from halogen atom, $C_1$-$C_3$-alkyl group, and a $C_1$-$C_3$-haloalkyl group,
  a 4- to 6-membered heterocycloalkyl group which is substituted one or more times with a group independently selected from a fluorine atom, a hydroxy group, and a $C_1$-$C_3$-alkyl group,
  a

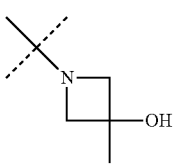

group, a

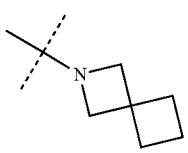

group, a

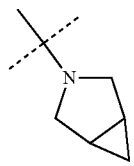

group,
a 5- to 10-membered heteroaryl group which is substituted one or more times with a group independently selected from an amino group, a chlorine atom, a fluorine atom, a trifluormethyl group, and a difluoromethyl group,
a $NR^5R^6$ group, and
a

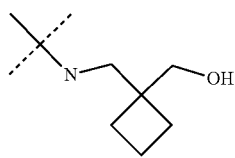

group,
$R^4$ is a hydrogen atom or a $C_1$-$C_3$-alkyl group;
$R^5$ is a hydrogen atom
$R^6$ is selected from
  a $C_1$-$C_3$-alkyl group which is substituted one or more times with a group selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group,
  and
  a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:
$R^1$ is a hydrogen atom, a fluorine atom, a chlorine atom, a methyl group, or a trifluoromethyl group;
$R^2$ is a hydrogen atom, a fluorine atom, or a chlorine atom;
with the proviso that both, $R^1$ and $R^2$, may not be a hydrogen atom at the same time;
$R^3$ is selected from a —(CH$_2$)—CH(CH$_3$)$_2$ group, a —(CH$_2$)$_3$O—CH$_3$ group, a —CH$_2$-(morpholin-4-yl) group, a —CH$_2$—N(CH$_3$)$_2$ group,
a —CH=C(CH$_3$)$_2$ group, a —CH=CH—CH$_2$—O—CH$_3$ group, a —CH=CH—CH$_2$—O—CH$_2$—CH$_3$ group,
a cyclopent-1-en-1-yl group,
a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group,
a piperidin1-yl group, a 3-hydroxy-piperidin-1-yl group, a 4,4-difluoro-piperidin-1-yl group, a 4-ethyl-4-hydroxy-piperidin-1-yl group, a group, a

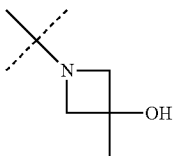

group, a

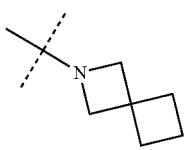

group, a

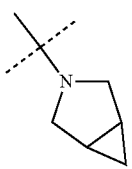

group, a 3-hydroxy-3-methyl-pyrrolidin-1-yl group, a 4-methyl-piperazin-1-yl group, a morpholin-4-yl group, a pyridin-4-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group, a —NH—CH$_2$-(pyrazol-3-yl) group, a —NH—CH$_2$-(pyrazol-5-yl) group, a —NH—CH$_2$-pyrazin-2-yl group, a —NH—(CH$_2$)$_2$O—CH$_3$ group, a —NH—CH$_2$—CH(OH)CF$_3$ group, a

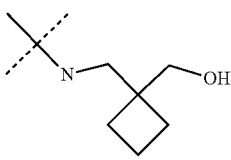

group, a NH-cyclopentyl group, a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH$_2$)—C(CH$_3$)$_2$—OH group, a —O—CH$_2$-(pyrazol-3-yl) group, a —O—(CH$_2$)$_2$—O—CH$_3$ group, a —O—CH$_2$-cyclobutyl group, a —O—CH$_2$-tetrahydofuran-2-yl group, a —O—(CH$_2$)$_2$—CF$_3$ group, and a —O—(CH$_2$)$_3$CH$_3$ group, R$^4$ is a hydrogen atom or a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

R$^1$ is a hydrogen atom, a fluorine atom, a chlorine atom, a methyl group, or a trifluoromethyl group;

R$^2$ is a hydrogen atom, a fluorine atom, or a chlorine atom;

with the proviso that both, R$^1$ and R$^2$, may not be a hydrogen atom at the same time;

R$^3$ is selected from a —(CH$_2$)—CH(CH$_3$)$_2$ group, a —(CH$_2$)$_3$—O—CH$_3$ group, a —CH$_2$-(morpholin-4-yl) group, a —CH$_2$—N(CH$_3$)$_2$ group, a —CH═C(CH$_3$)$_2$ group, a —CH═CH—CH$_2$—O—CH$_3$ group, a —CH═CH—CH$_2$—O—CH$_2$—CH$_3$ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a piperidin1-yl group, a 3-hydroxy-piperidin-1-yl group, a 4,4-difluoro-piperidin-1-yl group, a 4-ethyl-4-hydroxy-piperidin-1-yl group, a

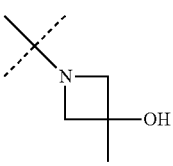

group, a

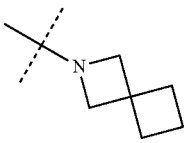

group, a

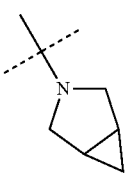

group, a 3-hydroxy-3-methyl-pyrrolidin-1-yl group, a 4-methyl-piperazin-1-yl group, a morpholin-4-yl group, a pyridin-4-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group, a —NH—CH$_2$-(pyrazol-3-yl) group, a —NH—CH$_2$-(pyrazol-5-yl) group, a —NH—CH$_2$-pyrazin-2-yl group, a —NH—(CH$_2$)$_2$O—CH$_3$ group, a —NH—CH$_2$—CH(OH)CF$_3$ group, a

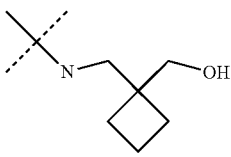

group, a NH-cyclopentyl group,
a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH$_2$)—C(CH$_3$)$_2$—OH group, a —O—CH$_2$-(pyrazol-3-yl) group, a —O—(CH$_2$)$_2$—O—CH$_3$ group, a —O—CH$_2$-cyclobutyl group, a —O—CH$_2$-tetrahydofuran-2-yl group, a —O—(CH$_2$)$_2$—CF$_3$ group, and a —O—(CH$_2$)$_3$CH$_3$ group, R$^4$ is a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

R$^1$ is a hydrogen atom, a fluorine atom, a chlorine atom, a methyl group, or a trifluoromethyl group;

R$^2$ is a hydrogen atom, a fluorine atom, or a chlorine atom;
with the proviso that both, R$^1$ and R$^2$, may not be a hydrogen atom at the same time;

R$^3$ is selected from a —(CH$_2$)—CH(CH$_3$)$_2$ group, a —(CH$_2$)$_3$O—CH$_3$ group, a —CH$_2$-(morpholin-4-yl) group, a —CH$_2$—N(CH$_3$)$_2$ group,
a —CH═C(CH$_3$)$_2$ group, a —CH═CH—CH$_2$—O—CH$_3$ group, a —CH═CH—CH$_2$—O—CH$_2$—CH$_3$ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a piperidin1-yl group, a 3-hydroxy-piperidin-1-yl group, a 4,4-difluoro-piperidin-1-yl group, a 4-ethyl-4-hydroxy-piperidin-1-yl group, a

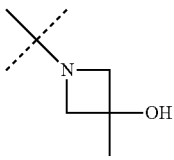

group, a

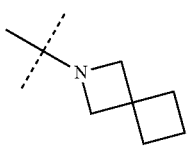

group, a

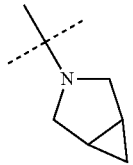

group, a 3-hydroxy-3-methyl-pyrrolidin-1-yl group, a 4-methyl-piperazin-1-yl group, a morpholin-4-yl group, a pyridin-4-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group, a —NH—CH$_2$-(pyrazol-3-yl) group, a —NH—CH$_2$-(pyrazol-5-yl) group, a —NH—CH$_2$-pyrazin-2-yl group, a —NH—(CH$_2$)$_2$—O—CH$_3$ group, a —NH—CH$_2$—CH(OH)CF$_3$ group, a

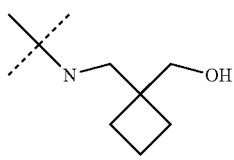

group, a NH-cyclopentyl group,
a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH$_2$)—C(CH$_3$)$_2$—OH group, a —O—CH$_2$-(pyrazol-3-yl) group, a —O—(CH$_2$)$_2$—O—CH$_3$ group, a —O—CH$_2$-cyclobutyl group, a —O—CH$_2$-tetrahydofuran-2-yl group, a —O—(CH$_2$)$_2$—CF$_3$ group, and a —O—(CH$_2$)$_3$CH$_3$ group, R$^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

R$^1$ is a hydrogen atom, a fluorine atom, a chlorine atom, a methyl group, or a trifluoromethyl group;

R$^2$ is a hydrogen atom, a fluorine atom, or a chlorine atom;
with the proviso that both, R$^1$ and R$^2$, may not be a hydrogen atom at the same time with the exception if R$^3$ is an ortho substituted phenyl group, both, R$^1$ and R$^2$, may also be a hydrogen atom;

R$^3$ is selected from a —(CH$_2$)$_3$—O—CH$_3$ group, a —CH$_2$-(morpholin-4-yl) group, a —CH$_2$—N(CH$_3$)$_2$ group,
a —CH═C(CH$_3$)$_2$ group, a —CH═CH—CH$_2$—O—CH$_3$ group, a —CH═CH—CH$_2$—O—CH$_2$—CH$_3$ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a 3-hydroxy-piperidin-1-yl group, a 4,4-difluoro-piperidin-1-yl group, a 4-ethyl-4-hydroxy-piperidin-1-yl group, a

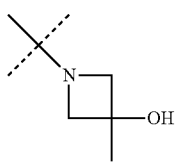

group, a

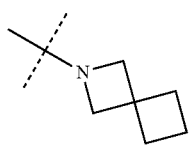

group, a

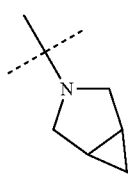

group,
a 3-hydroxy-3-methyl-pyrrolidin-1-yl group, a 4-methyl-piperazin-1-yl group,
a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group,
a —NH—CH$_2$-(pyrazol-3-yl) group, a —NH—CH$_2$-(pyrazol-5-yl) group, a —NH—CH$_2$-pyrazin-2-yl group, a —NH—CH$_2$—CH(OH)CF$_3$ group, a

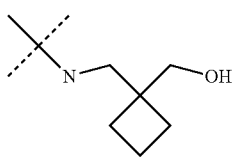

group, a NH-cyclopentyl group,
a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH$_2$)—C(CH$_3$)$_2$—OH group, a —O—CH$_2$-(pyrazol-3-yl) group, a —O—(CH$_2$)$_2$—O—CH$_3$ group, a —O—CH$_2$-cyclobutyl group, a —O—CH$_2$-tetrahydofuran-2-yl group, a —O—(CH$_2$)$_2$—CF$_3$ group, and a —O—(CH$_2$)$_3$CH$_3$ group,
R$^4$ is a hydrogen atom or a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:
R$^1$ is a hydrogen atom, a fluorine atom, a chlorine atom, a methyl group, or a trifluoromethyl group;
R$^2$ is a hydrogen atom, a fluorine atom, or a chlorine atom;
R$^3$ is selected from a —(CH$_2$)$_3$—O—CH$_3$ group, a —CH$_2$-(morpholin-4-yl) group, a —CH$_2$—N(CH$_3$)$_2$ group,
a —CH═C(CH$_3$)$_2$ group, a —CH═CH—CH$_2$—O—CH$_3$ group, a —CH═CH—CH$_2$—O—CH$_2$—CH$_3$ group,
a cyclopent-1-en-1-yl group,
a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group,
a 3-hydroxy-piperidin-1-yl group, a 4,4-difluoro-piperidin-1-yl group, a 4-ethyl-4-hydroxy-piperidin-1-yl group, a

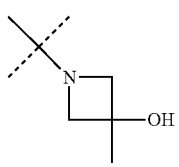

group, a

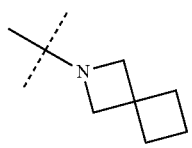

group, a

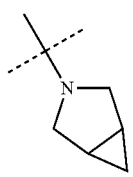

group,
a 3-hydroxy-3-methyl-pyrrolidin-1-yl group, a 4-methyl-piperazin-1-yl group,
a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group,
a —NH—CH$_2$-(pyrazol-3-yl) group, a —NH—CH$_2$-(pyrazol-5-yl) group, a —NH—CH$_2$-pyrazin-2-yl group, a —NH—CH$_2$—CH(OH)CF$_3$ group, a

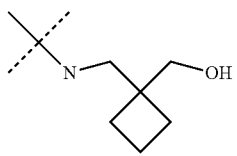

group, a NH-cyclopentyl group,
a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH₂)—C(CH₃)₂—OH group, a —O—CH₂-(pyrazol-3-yl) group, a —O—(CH₂)₂—O—CH₃ group, a —O—CH₂-cyclobutyl group, a —O—CH₂-tetrahydofuran-2-yl group, a —O—(CH₂)₂—CF₃ group, and a —O—(CH₂)₃CH₃ group, R⁴ is a hydrogen atom or a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

R¹ is a hydrogen atom, a fluorine atom, a chlorine atom, a methyl group, or a trifluoromethyl group;

R² is a hydrogen atom, a fluorine atom, or a chlorine atom; with the proviso that both, R¹ and R², may not be a hydrogen atom at the same time with the exception if R³ is an ortho substituted phenyl group, both, R¹ and R², may also be a hydrogen atom;

R³ is selected from a —(CH₂)₃—O—CH₃ group, a —CH₂-(morpholin-4-yl) group, a —CH₂—N(CH₃)₂ group, a —CH=C(CH₃)₂ group, a —CH=CH—CH₂—O—CH₃ group, a —CH=CH—CH₂—O—CH₂—CH₃ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a 3-hydroxy-piperidin-1-yl group, a 4,4-difluoro-piperidin-1-yl group, a 4-ethyl-4-hydroxy-piperidin-1-yl group, a

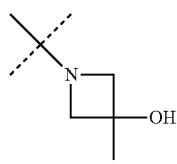

group, a

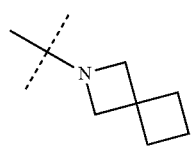

group, a

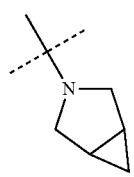

group, a 3-hydroxy-3-methyl-pyrrolidin-1-yl group, a 4-methyl-piperazin-1-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group, a —NH—CH₂-(pyrazol-3-yl) group, a —NH—CH₂-(pyrazol-5-yl) group, a —NH—CH₂-pyrazin-2-yl group, a —NH—CH₂—CH(OH)CF₃ group, a

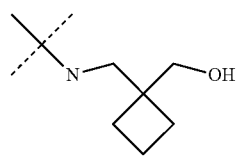

group, a NH-cyclopentyl group, a —O—(CH₂)₂—CH₃ group, a —O—(CH₂)₂—C(CH₃)₃ group, a —O—(CH₂)—CH(CH₃)—OH group, a —O—(CH₂)—C(CH₃)₂—OH group, a —O—CH₂-(pyrazol-3-yl) group, a —O—(CH₂)₂—O—CH₃ group, a —O—CH₂-cyclobutyl group, a —O—CH₂-tetrahydofuran-2-yl group, a —O—(CH₂)₂—CF₃ group, and a —O—(CH₂)₃CH₃ group, R⁴ is a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

R¹ is a hydrogen atom, a fluorine atom, a chlorine atom, a methyl group, or a trifluoromethyl group;

R² is a hydrogen atom, a fluorine atom, or a chlorine atom; with the proviso that both, R¹ and R², may not be a hydrogen atom at the same time with the exception if R³ is an ortho substituted phenyl group, both, R¹ and R², may also be a hydrogen atom;

R³ is selected from a —(CH₂)₃—O—CH₃ group, a —CH₂-(morpholin-4-yl) group, a —CH₂—N(CH₃)₂ group, a —CH=C(CH₃)₂ group, a —CH=CH—CH₂—O—CH₃ group, a —CH=CH—CH₂—O—CH₂—CH₃ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a 3-hydroxy-piperidin-1-yl group, a 4,4-difluoro-piperidin-1-yl group, a 4-ethyl-4-hydroxy-piperidin-1-yl group, a

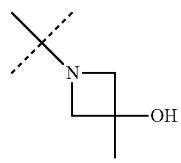

group, a

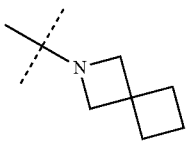

group, a

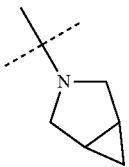

group,
a 3-hydroxy-3-methyl-pyrrolidin-1-yl group, a 4-methyl-piperazin-1-yl group,
a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group,
a —NH—$CH_2$-(pyrazol-3-yl) group, a —NH—$CH_2$-(pyrazol-5-yl) group, a —NH—$CH_2$-pyrazin-2-yl group, a —NH—$CH_2$—CH(OH)$CF_3$ group, a

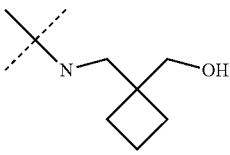

group, a NH-cyclopentyl group,
a —O—$(CH_2)_2$—$CH_3$ group, a —O—$(CH_2)_2$—C$(CH_3)_3$ group, a —O—$(CH_2)$—CH($CH_3$)—OH group, a —O—$(CH_2)$—C$(CH_3)_2$—OH group, a —O—$CH_2$-(pyrazol-3-yl) group, a —O—$(CH_2)_2$—O—$CH_3$ group, a —O—$CH_2$-cyclobutyl group, a —O—$CH_2$-tetrahydofuran-2-yl group, a —O—$(CH_2)_2$—$CF_3$ group, and a —O—$(CH_2)_3CH_3$ group,
$R^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a another embodiment of the first aspect, the present invention includes compounds of general formula (I), supra, in which:
$R^1$ is a hydrogen atom, a fluorine atom, a chlorine atom, a methyl group, or a trifluoromethyl group,
$R^2$ is a hydrogen atom, a fluorine atom, or a chlorine atom, with the proviso that both, $R^1$ and $R^2$, may not be a hydrogen atom at the same time;
$R^3$ is selected from a 5- to 6-membered heteroaryl group, which is substituted with a trifluoromethyl group,
a 4- to 6-membered heterocycloalkyl group,
which is substituted with a group independently selected from a hydroxy group or a $C_1$-$C_3$-alkyl group,
a $C_4$-$C_6$-heterocycloalkyl group which is optionally substituted with one or two groups independently selected from a $C_1$-$C_3$-alkyl group and a hydroxy group,
and
a $NR^5R^6$ group
$R^4$ is a methyl group;
$R^5$ is a hydrogen atom;
$R^6$ is
an $C_1$-$C_3$-alkyl group which itself is substituted one or more times with a group independently selected from a heteroaryl group, a $C_1$-$C_3$-haloalkyl group, and a hydroxy group,
and
a $C_5$-$C_6$-cycloalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a another embodiment of the first aspect, the present invention includes compounds of general formula (I), supra, in which:
$R^1$ is a hydrogen atom, a fluorine atom, a chlorine atom, a methyl group, or a trifluoromethyl group,
$R^2$ is a hydrogen atom, a fluorine atom, or a chlorine atom, with the proviso that both, $R^1$ and $R^2$, may not be a hydrogen atom at the same time;
$R^3$ is selected from a 5- to 6-membered heteroaryl group, which is substituted with a trifluoromethyl group,
a 4- to 6-membered heterocycloalkyl group,
which is substituted with a group independently selected from a hydroxy group or a $C_1$-$C_3$-alkyl group,
a $C_4$-$C_6$-heterocycloalkyl group which is optionally substituted with one or two groups independently selected from a $C_1$-$C_3$-alkyl group and a hydroxy group,
and
a $NR^5R^6$ group
$R^4$ is a methyl group;
$R^5$ is a hydrogen atom;
$R^6$ is
an $C_1$-$C_3$-alkyl group which itself is optionally substituted one or more times with a group independently selected from a heteroaryl group, a $C_1$-$C_3$-haloalkyl group, and a hydroxy group,
with the proviso that a $C_1$-$C_3$-alkyl group which is substituted with a pyridyl or a furanyl group and a hydroxy group as a single substituent is excluded
and
a $C_5$-$C_6$-cycloalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In accordance with yet another embodiment of the first aspect, the present invention includes compounds of general formula (I), supra, in which:
$R^1$ is a trifluormethyl group;
$R^2$ is a hydrogen atom
$R^3$ is selected from a —NH—$CH_2$—CH(OH)$CF_3$ group, a —NH-cyclopentyl group, a —NH—$CH_2$-(pyrazol-5-yl) group, a —NH—$CH_2$-pyrazin-2-yl group, a 3-hydroxy-3-methyl-azetidin-1-yl group, and a 3-trifluoromethyl-pyrazol-1-yl group, and
$R^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with yet another embodiment of the first aspect, the present invention includes compounds of general formula (I), supra, in which:

$R^1$ is a trifluormethyl group;
$R^2$ is a hydrogen atom
$R^3$ is selected from a —NH—CH$_2$—CH(OH)CF$_3$ group, a —NH-cyclopentyl group, a —NH—CH$_2$-(pyrazol-5-yl) group, a —NH—CH$_2$-pyrazin-2-yl group, a 3-hydroxy-3-methyl-azetidin-1-yl group, and a 3-trifluoromethyl-pyrazol-1-yl group, 3-difluoromethyl-pyrazol-1-yl group and
$R^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, selected from (5S)-6-{4-[(2-methoxyethyl)amino]-3-(trifluoromethyl)phenyl}-5-methyl-4,5-dihydro-1,2,4-triazin-3(2H)-one,
(5S)-6-[4-(2-azaspiro[3.3]heptan-2-yl)-3-(trifluoromethyl)phenyl]-5-methyl-4,5-dihydro-1,2,4-triazin-3(2H)-one,
(5S)-5-methyl-6-[4-{[(2S)-3,3,3-trifluoro-2-hydroxypropyl]amino}-3-(trifluoromethyl)phenyl]-4,5-dihydro-1,2,4-triazin-3(2H)-one,
(5S)-5-methyl-6-[4-(morpholin-4-yl)-3-(trifluoromethyl)phenyl]-4,5-dihydro-1,2,4-triazin-3(2H)-one,
(5S)-5-methyl-6-{3-(trifluoromethyl)-4-[4-(trifluoromethyl)-2H-1,2,3-triazol-2-yl]phenyl}-4,5-dihydro-1,2,4-triazin-3(2H)-one,
(5S)-5-methyl-6-{3-(trifluoromethyl)-4-[3-(difluoromethyl)-1H-pyrazol-1-yl]phenyl}-4,5-dihydro-1,2,4-triazin-3(2H)-one,
rel-(5R)-6-{4-[(1R,5R)-3-azabicyclo[3.1.0]hexan-3-yl]-3-(trifluoromethyl)phenyl}-5-methyl-4,5-dihydro-1,2,4-triazin-3(2H)-one,
(5S)-6-[4-({[1-(hydroxymethyl)cyclobutyl]methyl}amino)-3-(trifluoromethyl)phenyl]-5-methyl-4,5-dihydro-1,2,4-triazin-3(2H)-one,
(5S)-6-[4-(3-fluoro-1H-pyrazol-1-yl)-3-(trifluoromethyl)phenyl]-5-methyl-4,5-dihydro-1,2,4-triazin-3(2H)-one,
(5S)-6-[4-(4-ethyl-4-hydroxypiperidin-1-yl)-3-(trifluoromethyl)phenyl]-5-methyl-4,5-dihydro-1,2,4-triazin-3(2H)-one,
(5S)-6-{4-[(3S)-3-hydroxypiperidin-1-yl]-3-(trifluoromethyl)phenyl}-5-methyl-4,5-dihydro-1,2,4-triazin-3(2H)-one,
(5S)-6-{4-[(3R)-3-hydroxypiperidin-1-yl]-3-(trifluoromethyl)phenyl}-5-methyl-4,5-dihydro-1,2,4-triazin-3(2H)-one,
(5S)-5-methyl-6-[4-(piperidin-1-yl)-3-(trifluoromethyl)phenyl]-4,5-dihydro-1,2,4-triazin-3(2H)-one,
(5S)-6-{4-[(3R)-3-hydroxy-3-methylpyrrolidin-1-yl]-3-(trifluoromethyl)phenyl}-5-methyl-4,5-dihydro-1,2,4-triazin-3(2H)-one,
(5S)-6-{4-[(3S)-3-hydroxy-3-methylpyrrolidin-1-yl]-3-(trifluoromethyl)phenyl}-5-methyl-4,5-dihydro-1,2,4-triazin-3(2H)-one,
(5S)-5-methyl-6-[4-(4-methylpiperazin-1-yl)-3-(trifluoromethyl)phenyl]-4,5-dihydro-1,2,4-triazin-3(2H)-one,
(5S)-6-[4-(4,4-difluoropiperidin-1-yl)-3-(trifluoromethyl)phenyl]-5-methyl-4,5-dihydro-1,2,4-triazin-3(2H)-one,
(5S)-6-[4'-fluoro-2-(trifluoromethyl)[biphenyl]-4-yl]-5-methyl-4,5-dihydro-1,2,4-triazin-3(2H)-one,
(5S)-6-[4-(2-aminopyridin-4-yl)-3-(trifluoromethyl)phenyl]-5-methyl-4,5-dihydro-1,2,4-triazin-3(2H)-one,
(5S)-6-{4-[1-(difluoromethyl)-1H-pyrazol-4-yl]-3-(trifluoromethyl)phenyl}-5-methyl-4,5-dihydro-1,2,4-triazin-3(2H)-one,
(5S)-6-[4-(5-chloropyridin-2-yl)-3-(trifluoromethyl)phenyl]-5-methyl-4,5-dihydro-1,2,4-triazin-3(2H)-one,
(5S)-5-methyl-6-[4-(2-methylprop-1-en-1-yl)-3-(trifluoromethyl)phenyl]-4,5-dihydro-1,2,4-triazin-3(2H)-one,
(5S)-6-{4-[(1E)-3-methoxyprop-1-en-1-yl]-3-(trifluoromethyl)phenyl}-5-methyl-4,5-dihydro-1,2,4-triazin-3(2H)-one, (5S)-6-{4-[(E)-2-ethoxyvinyl]-3-(trifluoromethyl)phenyl}-5-methyl-4,5-dihydro-1,2,4-triazin-3(2H)-one,
(5S)-5-methyl-6-[4-(pyridin-4-yl)-3-(trifluoromethyl)phenyl]-4,5-dihydro-1,2,4-triazin-3(2H)-one,
(5S)-5-methyl-6-[4-(morpholin-4-ylmethyl)-3-(trifluoromethyl)phenyl]-4,5-dihydro-1,2,4-triazin-3(2H)-one,
(5S)-6-[4-(cyclopent-1-en-1-yl)-3-(trifluoromethyl)phenyl]-5-methyl-4,5-dihydro-1,2,4-triazin-3(2H)-one,
(5S)-6-[4'-chloro-2-(trifluoromethyl)[biphenyl]-4-yl]-5-methyl-4,5-dihydro-1,2,4-triazin-3(2H)-one,
(5S)-6-[3'-fluoro-4'-methyl-2-(trifluoromethyl)[biphenyl]-4-yl]-5-methyl-4,5-dihydro-1,2,4-triazin-3(2H)-one,
(5S)-6-{4-[(dimethylamino)methyl]-3-(trifluoromethyl)phenyl}-5-methyl-4,5-dihydro-1,2,4-triazin-3(2H)-one,
(5S)-6-{4-[(2R)-2-hydroxypropoxy]-3-(trifluoromethyl)phenyl}-5-methyl-4,5-dihydro-1,2,4-triazin-3(2H)-one,
(5S)-6-[4-(2-hydroxy-2-methylpropoxy)-3-(trifluoromethyl)phenyl]-5-methyl-4,5-dihydro-1,2,4-triazin-3(2H)-one,
(5S)-6-{4-[(2S)-2-hydroxypropoxy]-3-(trifluoromethyl)phenyl}-5-methyl-4,5-dihydro-1,2,4-triazin-3(2H)-one,
(5S)-5-methyl-6-[4-propoxy-3-(trifluoromethyl)phenyl]-4,5-dihydro-1,2,4-triazin-3(2H)-one,
(5S)-6-[4-(2-methoxyethoxy)-3-(trifluoromethyl)phenyl]-5-methyl-4,5-dihydro-1,2,4-triazin-3(2H)-one,
(5S)-6-[4-(cyclobutylmethoxy)-3-(trifluoromethyl)phenyl]-5-methyl-4,5-dihydro-1,2,4-triazin-3(2H)-one,
(5S)-5-methyl-6-{4-[(2S)-tetrahydrofuran-2-ylmethoxy]-3-(trifluoromethyl)phenyl}-4,5-dihydro-1,2,4-triazin-3(2H)-one,
(5S)-5-methyl-6-{4-[(2R)-tetrahydrofuran-2-ylmethoxy]-3-(trifluoromethyl)phenyl}-4,5-dihydro-1,2,4-triazin-3(2H)-one,
(5S)-5-methyl-6-[3-(trifluoromethyl)-4-(3,3,3-trifluoropropoxy)phenyl]-4,5-dihydro-1,2,4-triazin-3(2H)-one,
(5S)-6-[4-butoxy-3-(trifluoromethyl)phenyl]-5-methyl-4,5-dihydro-1,2,4-triazin-3(2H)-one,
(5S)-6-[4-(3,3-dimethylbutoxy)-3-(trifluoromethyl)phenyl]-5-methyl-4,5-dihydro-1,2,4-triazin-3(2H)-one,
(5S)-6-[4-(3-methoxypropyl)-3-(trifluoromethyl)phenyl]-5-methyl-4,5-dihydro-1,2,4-triazin-3(2H)-one,
(5S)-6-[4-isobutyl-3-(trifluoromethyl)phenyl]-5-methyl-4,5-dihydro-1,2,4-triazin-3(2H)-one,
(5S)-5-methyl-6-[4-(1H-pyrazol-3-ylmethoxy)-3-(trifluoromethyl)phenyl]-4,5-dihydro-1,2,4-triazin-3(2H)-one,
(5S)-6-(4'-fluoro-2'-methyl[biphenyl]-4-yl)-5-methyl-4,5-dihydro-1,2,4-triazin-3(2H)-one,
(5S)-6-[4'-fluoro-2'-(trifluoromethyl)[biphenyl]-4-yl]-5-methyl-4,5-dihydro-1,2,4-triazin-3(2H)-one,
(5S)-5-methyl-6-{3-(trifluoromethyl)-4-[3-(trifluoromethyl)-1H-pyrazol-1-yl]phenyl}-4,5-dihydro-1,2,4-triazin-3(2H)-one,
(5S)-5-methyl-6-[4-{[(1H-pyrazol-5-yl)methyl]amino}-3-(trifluoromethyl)phenyl]-4,5-dihydro-1,2,4-triazin-3(2H)-one,
(5S)-6-[4-(3-hydroxy-3-methylazetidin-1-yl)-3-(trifluoromethyl)phenyl]-5-methyl-4,5-dihydro-1,2,4-triazin-3(2H)-one,
(5S)-6-[4-(cyclopentylamino)-3-(trifluoromethyl)phenyl]-5-methyl-4,5-dihydro-1,2,4-triazin-3(2H)-one,
(5S)-5-methyl-6-[4-{[(2R)-3,3,3-trifluoro-2-hydroxypropyl]amino}-3-(trifluoromethyl)phenyl]-4,5-dihydro-1,2,4-triazin-3(2H)-one and
(5S)-5-methyl-6-[4-{[(pyrazin-2-yl)methyl]amino}-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

(5S)-6-[4'-fluoro-2-(trifluoromethyl)[biphenyl]-4-yl]-5-methyl-4,5-dihydro-1,2,4-triazin-3(2H)-one,
(5S)-6-[4-(2-aminopyridin-4-yl)-3-(trifluoromethyl)phenyl]-5-methyl-4,5-dihydro-1,2,4-triazin-3(2H)-one,
(5S)-6-{4-[1-(difluoromethyl)-1H-pyrazol-4-yl]-3-(trifluoromethyl)phenyl}-5-methyl-4,5-dihydro-1,2,4-triazin-3(2H)-one,
(5S)-6-[4-(5-chloropyridin-2-yl)-3-(trifluoromethyl)phenyl]-5-methyl-4,5-dihydro-1,2,4-triazin-3(2H)-one,
(5S)-5-methyl-6-[4-(2-methylprop-1-en-1-yl)-3-(trifluoromethyl)phenyl]-4,5-dihydro-1,2,4-triazin-3(2H)-one,
(5S)-6-{4-[(1E)-3-methoxyprop-1-en-1-yl]-3-(trifluoromethyl)phenyl}-5-methyl-4,5-dihydro-1,2,4-triazin-3(2H)-one,
(5S)-6-{4-[(E)-2-ethoxyvinyl]-3-(trifluoromethyl)phenyl}-5-methyl-4,5-dihydro-1,2,4-triazin-3(2H)-one,
(5S)-5-methyl-6-[4-(pyridin-4-yl)-3-(trifluoromethyl)phenyl]-4,5-dihydro-1,2,4-triazin-3(2H)-one,
(5S)-5-methyl-6-[4-(morpholin-4-ylmethyl)-3-(trifluoromethyl)phenyl]-4,5-dihydro-1,2,4-triazin-3(2H)-one,
(5S)-6-[4-(cyclopent-1-en-1-yl)-3-(trifluoromethyl)phenyl]-5-methyl-4,5-dihydro-1,2,4-triazin-3(2H)-one,
(5S)-6-[4'-chloro-2-(trifluoromethyl)[biphenyl]-4-yl]-5-methyl-4,5-dihydro-1,2,4-triazin-3(2H)-one,
(5S)-6-[3'-fluoro-4'-methyl-2-(trifluoromethyl)[biphenyl]-4-yl]-5-methyl-4,5-dihydro-1,2,4-triazin-3(2H)-one,
(5S)-6-{4-[(dimethylamino)methyl]-3-(trifluoromethyl)phenyl}-5-methyl-4,5-dihydro-1,2,4-triazin-3(2H)-one,
(5S)-6-{4-[(2R)-2-hydroxypropoxy]-3-(trifluoromethyl)phenyl}-5-methyl-4,5-dihydro-1,2,4-triazin-3(2H)-one,
(5S)-6-[4-(2-hydroxy-2-methylpropoxy)-3-(trifluoromethyl)phenyl]-5-methyl-4,5-dihydro-1,2,4-triazin-3(2H)-one,
(5S)-6-{4-[(2S)-2-hydroxypropoxy]-3-(trifluoromethyl)phenyl}-5-methyl-4,5-dihydro-1,2,4-triazin-3(2H)-one,
(5S)-5-methyl-6-[4-propoxy-3-(trifluoromethyl)phenyl]-4,5-dihydro-1,2,4-triazin-3(2H)-one,
(5S)-6-[4-(2-methoxyethoxy)-3-(trifluoromethyl)phenyl]-5-methyl-4,5-dihydro-1,2,4-triazin-3(2H)-one,
(5S)-6-[4-(cyclobutylmethoxy)-3-(trifluoromethyl)phenyl]-5-methyl-4,5-dihydro-1,2,4-triazin-3(2H)-one,
(5S)-5-methyl-6-{4-[(2S)-tetrahydrofuran-2-ylmethoxy]-3-(trifluoromethyl)phenyl}-4,5-dihydro-1,2,4-triazin-3(2H)-one,
(5S)-5-methyl-6-{4-[(2R)-tetrahydrofuran-2-ylmethoxy]-3-(trifluoromethyl)phenyl}-4,5-dihydro-1,2,4-triazin-3(2H)-one,
(5S)-5-methyl-6-[3-(trifluoromethyl)-4-(3,3,3-trifluoropropoxy)phenyl]-4,5-dihydro-1,2,4-triazin-3(2H)-one,
(5S)-6-[4-butoxy-3-(trifluoromethyl)phenyl]-5-methyl-4,5-dihydro-1,2,4-triazin-3(2H)-one,
(5S)-6-[4-(3,3-dimethylbutoxy)-3-(trifluoromethyl)phenyl]-5-methyl-4,5-dihydro-1,2,4-triazin-3(2H)-one,
(5S)-6-[4-(3-methoxypropyl)-3-(trifluoromethyl)phenyl]-5-methyl-4,5-dihydro-1,2,4-triazin-3(2H)-one,
(5S)-6-[4-isobutyl-3-(trifluoromethyl)phenyl]-5-methyl-4,5-dihydro-1,2,4-triazin-3(2H)-one,
(5S)-5-methyl-6-[4-(1H-pyrazol-3-ylmethoxy)-3-(trifluoromethyl)phenyl]-4,5-dihydro-1,2,4-triazin-3(2H)-one,
(5S)-6-(4'-fluoro-2'-methyl[biphenyl]-4-yl)-5-methyl-4,5-dihydro-1,2,4-triazin-3(2H)-one, (5S)-6-[4'-fluoro-2'-(trifluoromethyl)[biphenyl]-4-yl]-5-methyl-4,5-dihydro-1,2,4-triazin-3(2H)-one,
(5S)-5-methyl-6-{3-(trifluoromethyl)-4-[3-(trifluoromethyl)-1H-pyrazol-1-yl]phenyl}-4,5-dihydro-1,2,4-triazin-3(2H)-one,
(5S)-5-methyl-6-{3-(trifluoromethyl)-4-[3-(difluoromethyl)-1H-pyrazol-1-yl]phenyl}-4,5-dihydro-1,2,4-triazin-3(2H)-one,
(5S)-5-methyl-6-[4-{[(1H-pyrazol-5-yl)methyl]amino}-3-(trifluoromethyl)phenyl]-4,5-dihydro-1,2,4-triazin-3(2H)-one,
(5S)-6-[4-(3-hydroxy-3-methylazetidin-1-yl)-3-(trifluoromethyl)phenyl]-5-methyl-4,5-dihydro-1,2,4-triazin-3(2H)-one,
(5S)-6-[4-(cyclopentylamino)-3-(trifluoromethyl)phenyl]-5-methyl-4,5-dihydro-1,2,4-triazin-3(2H)-one,
(5S)-5-methyl-6-[4-{[(2R)-3,3,3-trifluoro-2-hydroxypropyl]amino}-3-(trifluoromethyl)phenyl]-4,5-dihydro-1,2,4-triazin-3(2H)-one and
(5S)-5-methyl-6-[4-{[(pyrazin-2-yl)methyl]amino}-3-(trifluoromethyl)phenyl]-4,5-dihydro-1,2,4-triazin-3(2H)-one, or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes (5S)-6-{4-[(2-methoxyethyl)amino]-3-(trifluoromethyl)phenyl}-5-methyl-4,5-dihydro-1,2,4-triazin-3(2H)-one,
(5S)-6-[4-(2-azaspiro[3.3]heptan-2-yl)-3-(trifluoromethyl)phenyl]-5-methyl-4,5-dihydro-1,2,4-triazin-3(2H)-one,
(5S)-5-methyl-6-[4-{[(2S)-3,3,3-trifluoro-2-hydroxypropyl]amino}-3-(trifluoromethyl)phenyl]-4,5-dihydro-1,2,4-triazin-3(2H)-one,
(5S)-5-methyl-6-[4-(morpholin-4-yl)-3-(trifluoromethyl)phenyl]-4,5-dihydro-1,2,4-triazin-3(2H)-one,
(5S)-5-methyl-6-{3-(trifluoromethyl)-4-[4-(trifluoromethyl)-2H-1,2,3-triazol-2-yl]phenyl}-4,5-dihydro-1,2,4-triazin-3(2H)-one,
rel-(5R)-6-{4-[(1R,5R)-3-azabicyclo[3.1.0]hexan-3-yl]-3-(trifluoromethyl)phenyl}-5-methyl-4,5-dihydro-1,2,4-triazin-3(2H)-one,
(5S)-6-[4-({[1-(hydroxymethyl)cyclobutyl]methyl}amino)-3-(trifluoromethyl)phenyl]-5-methyl-4,5-dihydro-1,2,4-triazin-3(2H)-one,
(5S)-6-[4-(3-fluoro-1H-pyrazol-1-yl)-3-(trifluoromethyl)phenyl]-5-methyl-4,5-dihydro-1,2,4-triazin-3(2H)-one,
(5S)-6-[4-(4-ethyl-4-hydroxypiperidin-1-yl)-3-(trifluoromethyl)phenyl]-5-methyl-4,5-dihydro-1,2,4-triazin-3(2H)-one,
(5S)-6-{4-[(3S)-3-hydroxypiperidin-1-yl]-3-(trifluoromethyl)phenyl}-5-methyl-4,5-dihydro-1,2,4-triazin-3(2H)-one,
(5S)-6-{4-[(3R)-3-hydroxypiperidin-1-yl]-3-(trifluoromethyl)phenyl}-5-methyl-4,5-dihydro-1,2,4-triazin-3(2H)-one,
(5S)-5-methyl-6-[4-(piperidin-1-yl)-3-(trifluoromethyl)phenyl]-4,5-dihydro-1,2,4-triazin-3(2H)-one,
(5S)-6-{4-[(3R)-3-hydroxy-3-methylpyrrolidin-1-yl]-3-(trifluoromethyl)phenyl}-5-methyl-4,5-dihydro-1,2,4-triazin-3(2H)-one,
(5S)-6-{4-[(3S)-3-hydroxy-3-methylpyrrolidin-1-yl]-3-(trifluoromethyl)phenyl}-5-methyl-4,5-dihydro-1,2,4-triazin-3(2H)-one,
(5S)-5-methyl-6-[4-(4-methylpiperazin-1-yl)-3-(trifluoromethyl)phenyl]-4,5-dihydro-1,2,4-triazin-3(2H)-one,
(5S)-6-[4-(4,4-difluoropiperidin-1-yl)-3-(trifluoromethyl)phenyl]-5-methyl-4,5-dihydro-1,2,4-triazin-3(2H)-one,
(5S)-6-[4'-fluoro-2'-(trifluoromethyl)[biphenyl]-4-yl]-5-methyl-4,5-dihydro-1,2,4-triazin-3(2H)-one,
(5S)-6-[4-(2-aminopyridin-4-yl)-3-(trifluoromethyl)phenyl]-5-methyl-4,5-dihydro-1,2,4-triazin-3(2H)-one,
(5S)-6-{4-[1-(difluoromethyl)-1H-pyrazol-4-yl]-3-(trifluoromethyl)phenyl}-5-methyl-4,5-dihydro-1,2,4-triazin-3(2H)-one,
(5S)-6-[4-(5-chloropyridin-2-yl)-3-(trifluoromethyl)phenyl]-5-methyl-4,5-dihydro-1,2,4-triazin-3(2H)-one,
(5S)-5-methyl-6-[4-(2-methylprop-1-en-1-yl)-3-(trifluoromethyl)phenyl]-4,5-dihydro-1,2,4-triazin-3(2H)-one,
(5S)-6-{4-[(1E)-3-methoxyprop-1-en-1-yl]-3-(trifluoromethyl)phenyl}-5-methyl-4,5-dihydro-1,2,4-triazin-3(2H)-one,
(5S)-6-{4-[(E)-2-ethoxyvinyl]-3-(trifluoromethyl)phenyl}-5-methyl-4,5-dihydro-1,2,4-triazin-3(2H)-one,
(5S)-5-methyl-6-[4-(pyridin-4-yl)-3-(trifluoromethyl)phenyl]-4,5-dihydro-1,2,4-triazin-3(2H)-one,
(5S)-5-methyl-6-[4-(morpholin-4-ylmethyl)-3-(trifluoromethyl)phenyl]-4,5-dihydro-1,2,4-triazin-3(2H)-one,
(5S)-6-[4-(cyclopent-1-en-1-yl)-3-(trifluoromethyl)phenyl]-5-methyl-4,5-dihydro-1,2,4-triazin-3(2H)-one,
(5S)-6-[4'-chloro-2-(trifluoromethyl)[biphenyl]-4-yl]-5-methyl-4,5-dihydro-1,2,4-triazin-3(2H)-one,
(5S)-6-[3'-fluoro-4'-methyl-2-(trifluoromethyl)[biphenyl]-4-yl]-5-methyl-4,5-dihydro-1,2,4-triazin-3(2H)-one,
(5S)-6-{4-[(dimethylamino)methyl]-3-(trifluoromethyl)phenyl}-5-methyl-4,5-dihydro-1,2,4-triazin-3(2H)-one,
(5S)-6-{4-[(2R)-2-hydroxypropoxy]-3-(trifluoromethyl)phenyl}-5-methyl-4,5-dihydro-1,2,4-triazin-3(2H)-one,
(5S)-6-[4-(2-hydroxy-2-methylpropoxy)-3-(trifluoromethyl)phenyl]-5-methyl-4,5-dihydro-1,2,4-triazin-3(2H)-one,
(5S)-6-{4-[(2S)-2-hydroxypropoxy]-3-(trifluoromethyl)phenyl}-5-methyl-4,5-dihydro-1,2,4-triazin-3(2H)-one,
(5S)-5-methyl-6-[4-propoxy-3-(trifluoromethyl)phenyl]-4,5-dihydro-1,2,4-triazin-3(2H)-one,
(5S)-6-[4-(2-methoxyethoxy)-3-(trifluoromethyl)phenyl]-5-methyl-4,5-dihydro-1,2,4-triazin-3(2H)-one,
(5S)-6-[4-(cyclobutylmethoxy)-3-(trifluoromethyl)phenyl]-5-methyl-4,5-dihydro-1,2,4-triazin-3(2H)-one,
(5S)-5-methyl-6-{4-[(2S)-tetrahydrofuran-2-ylmethoxy]-3-(trifluoromethyl)phenyl}-4,5-dihydro-1,2,4-triazin-3(2H)-one,
(5S)-5-methyl-6-{4-[(2R)-tetrahydrofuran-2-ylmethoxy]-3-(trifluoromethyl)phenyl}-4,5-dihydro-1,2,4-triazin-3(2H)-one,
(5S)-5-methyl-6-[3-(trifluoromethyl)-4-(3,3,3-trifluoropropoxy)phenyl]-4,5-dihydro-1,2,4-triazin-3(2H)-one,
(5S)-6-[4-butoxy-3-(trifluoromethyl)phenyl]-5-methyl-4,5-dihydro-1,2,4-triazin-3(2H)-one,
(5S)-6-[4-(3,3-dimethylbutoxy)-3-(trifluoromethyl)phenyl]-5-methyl-4,5-dihydro-1,2,4-triazin-3(2H)-one,
(5S)-6-[4-(3-methoxypropyl)-3-(trifluoromethyl)phenyl]-5-methyl-4,5-dihydro-1,2,4-triazin-3(2H)-one,
(5S)-6-[4-isobutyl-3-(trifluoromethyl)phenyl]-5-methyl-4,5-dihydro-1,2,4-triazin-3(2H)-one,
(5S)-5-methyl-6-[4-(1H-pyrazol-3-ylmethoxy)-3-(trifluoromethyl)phenyl]-4,5-dihydro-1,2,4-triazin-3(2H)-one,
(5S)-6-(4'-fluoro-2'-methyl[biphenyl]-4-yl)-5-methyl-4,5-dihydro-1,2,4-triazin-3(2H)-one and
(5S)-6-[4'-fluoro-2'-(trifluoromethyl)[biphenyl]-4-yl]-5-methyl-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

(5S)-6-{4-[(2-methoxyethyl)amino]-3-(trifluoromethyl) phenyl}-5-methyl-4,5-dihydro-1,2,4-triazin-3(2H)-one
(5S)-6-[4-(2-azaspiro[3.3]heptan-2-yl)-3-(trifluoromethyl) phenyl]-5-methyl-4,5-dihydro-1,2,4-triazin-3(2H)-one
(5S)-5-methyl-6-[4-{[(2S)-3,3,3-trifluoro-2-hydroxypropyl] amino}-3-(trifluoromethyl)phenyl]-4,5-dihydro-1,2,4-triazin-3(2H)-one
(5S)-5-methyl-6-[4-(morpholin-4-yl)-3-(trifluoromethyl) phenyl]-4,5-dihydro-1,2,4-triazin-3(2H)-one
(5S)-5-methyl-6-{3-(trifluoromethyl)-4-[4-(trifluoromethyl)-2H-1,2,3-triazol-2-yl]phenyl}-4,5-dihydro-1,2,4-triazin-3(2H)-one rel-(5R)-6-{4-[(1R,5R)-3-azabicyclo [3.1.0]hexan-3-yl]-3-(trifluoromethyl)phenyl}-5-methyl-4,5-dihydro-1,2,4-triazin-3(2H)-one
(5S)-6-[4-({[1-(hydroxymethyl)cyclobutyl]methyl}amino)-3-(trifluoromethyl)phenyl]-5-methyl-4,5-dihydro-1,2,4-triazin-3(2H)-one
(5S)-6-[4-(3-fluoro-1H-pyrazol-1-yl)-3-(trifluoromethyl) phenyl]-5-methyl-4,5-dihydro-1,2,4-triazin-3(2H)-one
(5S)-6-[4-(4-ethyl-4-hydroxypiperidin-1-yl)-3-(trifluoromethyl)phenyl]-5-methyl-4,5-dihydro-1,2,4-triazin-3(2H)-one
(5S)-6-{4-[(3S)-3-hydroxypiperidin-1-yl]-3-(trifluoromethyl)phenyl}-5-methyl-4,5-dihydro-1,2,4-triazin-3(2H)-one
(5S)-6-{4-[(3R)-3-hydroxypiperidin-1-yl]-3-(trifluoromethyl)phenyl}-5-methyl-4,5-dihydro-1,2,4-triazin-3(2H)-one
(5S)-5-methyl-6-[4-(piperidin-1-yl)-3-(trifluoromethyl)phenyl]-4,5-dihydro-1,2,4-triazin-3(2H)-one
(5S)-6-{4-[(3R)-3-hydroxy-3-methylpyrrolidin-1-yl]-3-(trifluoromethyl)phenyl}-5-methyl-4,5-dihydro-1,2,4-triazin-3(2H)-one
(5S)-6-{4-[(3S)-3-hydroxy-3-methylpyrrolidin-1-yl]-3-(trifluoromethyl)phenyl}-5-methyl-4,5-dihydro-1,2,4-triazin-3(2H)-one
(5S)-5-methyl-6-[4-(4-methylpiperazin-1-yl)-3-(trifluoromethyl)phenyl]-4,5-dihydro-1,2,4-triazin-3(2H)-one
(5S)-6-[4-(4,4-difluoropiperidin-1-yl)-3-(trifluoromethyl) phenyl]-5-methyl-4,5-dihydro-1,2,4-triazin-3(2H)-one
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

(5S)-6-[4'-fluoro-2-(trifluoromethyl)[biphenyl]-4-yl]-5-methyl-4,5-dihydro-1,2,4-triazin-3(2H)-one
(5S)-6-[4-(2-aminopyridin-4-yl)-3-(trifluoromethyl)phenyl]-5-methyl-4,5-dihydro-1,2,4-triazin-3(2H)-one
(5S)-6-{4-[1-(difluoromethyl)-1H-pyrazol-4-yl]-3-(trifluoromethyl)phenyl}-5-methyl-4,5-dihydro-1,2,4-triazin-3 (2H)-one
(5S)-6-[4-(5-chloropyridin-2-yl)-3-(trifluoromethyl)phenyl]-5-methyl-4,5-dihydro-1,2,4-triazin-3(2H)-one
(5S)-5-methyl-6-[4-(2-methylprop-1-en-1-yl)-3-(trifluoromethyl)phenyl]-4,5-dihydro-1,2,4-triazin-3(2H)-one
(5S)-6-{4-[(1E)-3-methoxyprop-1-en-1-yl]-3-(trifluoromethyl)phenyl}-5-methyl-4,5-dihydro-1,2,4-triazin-3(2H)-one
(5S)-6-{4-[(E)-2-ethoxyvinyl]-3-(trifluoromethyl)phenyl}-5-methyl-4,5-dihydro-1,2,4-triazin-3(2H)-one
(5S)-5-methyl-6-[4-(pyridin-4-yl)-3-(trifluoromethyl)phenyl]-4,5-dihydro-1,2,4-triazin-3(2H)-one
(5S)-5-methyl-6-[4-(morpholin-4-ylmethyl)-3-(trifluoromethyl)phenyl]-4,5-dihydro-1,2,4-triazin-3(2H)-one
(5S)-6-[4-(cyclopent-1-en-1-yl)-3-(trifluoromethyl)phenyl]-5-methyl-4,5-dihydro-1,2,4-triazin-3(2H)-one
(5S)-6-[4'-chloro-2-(trifluoromethyl)[biphenyl]-4-yl]-5-methyl-4,5-dihydro-1,2,4-triazin-3(2H)-one
(5S)-6-[3'-fluoro-4'-methyl-2-(trifluoromethyl)[biphenyl]-4-yl]-5-methyl-4,5-dihydro-1,2,4-triazin-3(2H)-one
(5S)-6-{4-[(dimethylamino)methyl]-3-(trifluoromethyl) phenyl}-5-methyl-4,5-dihydro-1,2,4-triazin-3(2H)-one
(5S)-6-{4-[(2R)-2-hydroxypropoxy]-3-(trifluoromethyl) phenyl}-5-methyl-4,5-dihydro-1,2,4-triazin-3(2H)-one
(5S)-6-[4-(2-hydroxy-2-methylpropoxy)-3-(trifluoromethyl)phenyl]-5-methyl-4,5-dihydro-1,2,4-triazin-3(2H)-one
(5S)-6-{4-[(2S)-2-hydroxypropoxy]-3-(trifluoromethyl) phenyl}-5-methyl-4,5-dihydro-1,2,4-triazin-3(2H)-one
(5S)-5-methyl-6-[4-propoxy-3-(trifluoromethyl)phenyl]-4,5-dihydro-1,2,4-triazin-3(2H)-one
(5S)-6-[4-(2-methoxyethoxy)-3-(trifluoromethyl)phenyl]-5-methyl-4,5-dihydro-1,2,4-triazin-3(2H)-one
(5S)-6-[4-(cyclobutylmethoxy)-3-(trifluoromethyl)phenyl]-5-methyl-4,5-dihydro-1,2,4-triazin-3(2H)-one
(5S)-5-methyl-6-{4-[(2S)-tetrahydrofuran-2-ylmethoxy]-3-(trifluoromethyl)phenyl}-4,5-dihydro-1,2,4-triazin-3 (2H)-one
(5S)-5-methyl-6-{4-[(2R)-tetrahydrofuran-2-ylmethoxy]-3-(trifluoromethyl)phenyl}-4,5-dihydro-1,2,4-triazin-3 (2H)-one
(5S)-5-methyl-6-[3-(trifluoromethyl)-4-(3,3,3-trifluoropropoxy)phenyl]-4,5-dihydro-1,2,4-triazin-3(2H)-one
(5S)-6-[4-butoxy-3-(trifluoromethyl)phenyl]-5-methyl-4,5-dihydro-1,2,4-triazin-3(2H)-one
(5S)-6-[4-(3,3-dimethylbutoxy)-3-(trifluoromethyl)phenyl]-5-methyl-4,5-dihydro-1,2,4-triazin-3(2H)-one
(5S)-6-[4-(3-methoxypropyl)-3-(trifluoromethyl)phenyl]-5-methyl-4,5-dihydro-1,2,4-triazin-3(2H)-one
(5S)-6-[4-isobutyl-3-(trifluoromethyl)phenyl]-5-methyl-4,5-dihydro-1,2,4-triazin-3(2H)-one
(5S)-5-methyl-6-[4-(1H-pyrazol-3-ylmethoxy)-3-(trifluoromethyl)phenyl]-4,5-dihydro-1,2,4-triazin-3(2H)-one
(5S)-6-(4'-fluoro-2'-methyl[biphenyl]-4-yl)-5-methyl-4,5-dihydro-1,2,4-triazin-3(2H)-one
(5S)-6-[4'-fluoro-2'-(trifluoromethyl)[biphenyl]-4-yl]-5-methyl-4,5-dihydro-1,2,4-triazin-3(2H)-one
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, in which:

(5S)-6-[4'-fluoro-2-(trifluoromethyl)[biphenyl]-4-yl]-5-methyl-4,5-dihydro-1,2,4-triazin-3(2H)-one
(5S)-6-[4-(2-aminopyridin-4-yl)-3-(trifluoromethyl)phenyl]-5-methyl-4,5-dihydro-1,2,4-triazin-3(2H)-one
(5S)-6-{4-[1-(difluoromethyl)-1H-pyrazol-4-yl]-3-(trifluoromethyl)phenyl}-5-methyl-4,5-dihydro-1,2,4-triazin-3 (2H)-one
(5S)-6-[4-(5-chloropyridin-2-yl)-3-(trifluoromethyl)phenyl]-5-methyl-4,5-dihydro-1,2,4-triazin-3(2H)-one
(5S)-5-methyl-6-[4-(2-methylprop-1-en-1-yl)-3-(trifluoromethyl)phenyl]-4,5-dihydro-1,2,4-triazin-3(2H)-one (5S)-6-{4-[(1E)-3-methoxyprop-1-en-1-yl]-3-(trifluoromethyl)phenyl}-5-methyl-4,5-dihydro-1,2,4-triazin-3(2H)-one (5S)-6-{4-[(E)-2-ethoxyvinyl]-3-(trifluoromethyl)phenyl}-5-methyl-4,5-dihydro-1,2,4-triazin-3(2H)-one (5S)-5-methyl-6-[4-(pyridin-4-yl)-3-(trifluoromethyl)phenyl]-4,5-dihydro-1,2,4-triazin-3(2H)-one (5S)-5-methyl-6-[4-(morpholin-4-ylmethyl)-3-(trifluoromethyl)phenyl]-4,5-dihydro-1,2,4-triazin-3(2H)-one (5S)-6-[4-(cyclopent-1-en-1-yl)-3-(trifluoromethyl)phenyl]-5-methyl-4,5-dihydro-1,2,4-triazin-3(2H)-one (5S)-6-[4'-chloro-2-(trifluoromethyl)[biphenyl]-4-yl]-5-methyl-4,5-dihydro-1,2,4-triazin-3(2H)-one (5S)-6-[3'-fluoro-4'-methyl-2-(trifluoromethyl)[biphenyl]-4-yl]-5-methyl-4,5-dihydro-1,2,4-triazin-3(2H)-one (5S)-6-{4-[(dimethylamino)methyl]-3-(trifluoromethyl)phenyl}-5-methyl-4,5-dihydro-1,2,4-triazin-3(2H)-one (5S)-6-{4-[(2R)-2-hydroxypropoxy]-3-(trifluoromethyl)phenyl}-5-methyl-4,5-dihydro-1,2,4-triazin-3(2H)-one (5S)-6-[4-(2-hydroxy-2-methylpropoxy)-3-(trifluoromethyl)phenyl]-5-methyl-4,5-dihydro-1,2,4-triazin-3(2H)-one (5S)-6-{4-[(2S)-2-hydroxypropoxy]-3-(trifluoromethyl)phenyl}-5-methyl-4,5-dihydro-1,2,4-triazin-3(2H)-one (5S)-5-methyl-6-[4-propoxy-3-(trifluoromethyl)phenyl]-4,5-dihydro-1,2,4-triazin-3(2H)-one (5S)-6-[4-(2-methoxyethoxy)-3-(trifluoromethyl)phenyl]-5-methyl-4,5-dihydro-1,2,4-triazin-3(2H)-one (5S)-6-[4-(cyclobutylmethoxy)-3-(trifluoromethyl)phenyl]-5-methyl-4,5-dihydro-1,2,4-triazin-3(2H)-one (5S)-5-methyl-6-{4-[(2S)-tetrahydrofuran-2-ylmethoxy]-3-(trifluoromethyl)phenyl}-4,5-dihydro-1,2,4-triazin-3(2H)-one (5S)-5-methyl-6-{4-[(2R)-tetrahydrofuran-2-ylmethoxy]-3-(trifluoromethyl)phenyl}-4,5-dihydro-1,2,4-triazin-3(2H)-one (5S)-5-methyl-6-[3-(trifluoromethyl)-4-(3,3,3-trifluoropropoxy)phenyl]-4,5-dihydro-1,2,4-triazin-3(2H)-one (5S)-6-[4-butoxy-3-(trifluoromethyl)phenyl]-5-methyl-4,5-dihydro-1,2,4-triazin-3(2H)-one (5S)-6-[4-(3,3-dimethylbutoxy)-3-(trifluoromethyl)phenyl]-5-methyl-4,5-dihydro-1,2,4-triazin-3(2H)-one (5S)-6-[4-(3-methoxypropyl)-3-(trifluoromethyl)phenyl]-5-methyl-4,5-dihydro-1,2,4-triazin-3(2H)-one (5S)-6-[4-isobutyl-3-(trifluoromethyl)phenyl]-5-methyl-4,5-dihydro-1,2,4-triazin-3(2H)-one (5S)-5-methyl-6-[4-(1H-pyrazol-3-ylmethoxy)-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra:

(5S)-6-(4'-fluoro-2'-methyl[biphenyl]-4-yl)-5-methyl-4,5-dihydro-1,2,4-triazin-3(2H)-one (5S)-6-[4'-fluoro-2'-(trifluoromethyl)[biphenyl]-4-yl]-5-methyl-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes compounds of general formula (I), supra, selected from (5S)-5-methyl-6-{3-(trifluoromethyl)-4-[3-(trifluoromethyl)-1H-pyrazol-1-yl]phenyl}-4,5-dihydro-1,2,4-triazin-3(2H)-one (5S)-5-methyl-6-[4-{[(1H-pyrazol-5-yl)methyl]amino}-3-(trifluoromethyl)phenyl]-4,5-dihydro-1,2,4-triazin-3(2H)-one (5S)-6-[4-(3-hydroxy-3-methylazetidin-1-yl)-3-(trifluoromethyl)phenyl]-5-methyl-4,5-dihydro-1,2,4-triazin-3(2H)-one (5S)-6-[4-(cyclopentylamino)-3-(trifluoromethyl)phenyl]-5-methyl-4,5-dihydro-1,2,4-triazin-3(2H)-one (5S)-5-methyl-6-[4-{[(2R)-3,3,3-trifluoro-2-hydroxypropyl]amino}-3-(trifluoromethyl)phenyl]-4,5-dihydro-1,2,4-triazin-3(2H)-one (5S)-5-methyl-6-[4-{[(pyrazin-2-yl)methyl]amino}-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), (5S)-5-methyl-6-{3-(trifluoromethyl)-4-[3-(trifluoromethyl)-1H-pyrazol-1-yl]phenyl}-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), (5S)-5-methyl-6-[4-{[(1H-pyrazol-5-yl)methyl]amino}-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), supra, (5S)-6-[4-(3-hydroxy-3-methylazetidin-1-yl)-3-(trifluoromethyl)phenyl]-5-methyl-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), supra, (5S)-6-[4-(cyclopentylamino)-3-(trifluoromethyl)phenyl]-5-methyl-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), supra, (5S)-5-methyl-6-[4-{[(2R)-3,3,3-trifluoro-2-hydroxypropyl]amino}-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further embodiment of the first aspect, the present invention includes the compound of general formula (I), supra, (5S)-5-methyl-6-[4-{[(pyrazin-2-yl)methyl]amino}-3-(trifluoromethyl)phenyl]-4,5-dihydro-1,2,4-triazin-3(2H)-one or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
$R^3$ is
a phenyl group which is substituted one or more times with a group independently selected from halogen atom, a $C_1$-$C_3$-alkyl group, a $C_1$-$C_3$-haloalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
$R^3$ is
a phenyl group which is substituted one or more times with a group independently selected from halogen atom, a $C_1$-$C_3$-alkyl group, a $C_1$-$C_3$-fluoroalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
with the proviso that both, $R^1$ and $R^2$, may not be a hydrogen atom at the same time, with the exception if $R^3$ is an ortho substituted phenyl group, both, $R^1$ and $R^2$, may also be a hydrogen atom;
$R^3$ is
a phenyl group which is substituted one or more times with a group independently selected from halogen atom, a $C_1$-$C_3$-alkyl group, a $C_1$-$C_3$-haloalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
with the proviso that both, $R^1$ and $R^2$, may not be a hydrogen atom at the same time, with the exception if $R^3$ is an ortho substituted phenyl group, both, $R^1$ and $R^2$, may also be a hydrogen atom;
$R^3$ is
a phenyl group which is substituted one or more times with a group independently selected from halogen atom, a $C_1$-$C_3$-alkyl group, a $C_1$-$C_3$-fluoroalkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
with the proviso that both, $R^1$ and $R^2$, may not be a hydrogen atom at the same time, with the exception if $R^3$ is an ortho substituted phenyl group, both, $R^1$ and $R^2$, may also be a hydrogen atom;
$R^3$ is a phenyl group which is substituted one or more times with a group independently selected from fluorine atom, a chlorine atom, a methyl group, a trifluoromethyl group and a difluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a trifluoromethyl group
$R^2$ is a hydrogen atom
$R^3$ is a phenyl group which is substituted one or more times with a group independently selected from halogen atom, a $C_1$-$C_3$-alkyl group, a $C_1$-$C_3$-haloalkyl group,
$R^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a trifluoromethyl group
$R^2$ is a hydrogen atom
$R^3$ is a phenyl group which is substituted one or more times with a group independently selected from fluorine atom, a chlorine atom, a methyl group, a trifluoromethyl group and a difluoromethyl group,
$R^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a trifluoromethyl group
$R^2$ is a hydrogen atom
$R^3$ is selected from a 4-chlorophenyl group, a 4-fluorophenyl group, a 4-fluoro-2-methyl-phenyl group, a 3-fluoro-4-methyl-phenyl group, and a 4-fluoro-2-trifluoromethyl-phenyl group, and
$R^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a phenyl group which is substituted one or more times with a group independently selected from a fluorine atom, a chlorine atom, a methyl group, a trifluoromethyl group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a C$_1$-C$_6$-alkyl group, or a C$_1$-C$_3$-alkyl group which is optionally substituted one or more times with a group independently selected from a C$_1$-C$_3$-alkoxy group, a heterocycloalkyl group, and a NR$^5$R$^6$ group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a C$_1$-C$_3$-haloalkyl group
R$^2$ is a hydrogen atom
R$^3$ is a C$_1$-C$_6$-alkyl group, or a C$_1$-C$_3$-alkyl group which is optionally substituted one or more times with a group independently selected from a C$_1$-C$_3$-alkoxy group, a heterocycloalkyl group, and a NR$^5$R$^6$ group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a C$_2$-C$_6$-alkenyl group, which is optionally substituted with a C$_1$-C$_3$-alkoxy group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a C$_5$-C$_6$-cycloalkenyl group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a 4- to 6-membered heterocycloalkyl group which is optionally substituted one or more times with a group independently selected from a fluorine atom, a hydroxy group, and a C$_1$-C$_3$-alkyl group;
a

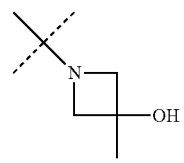

group, a

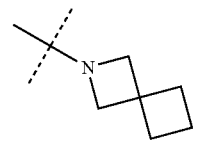

group, or a

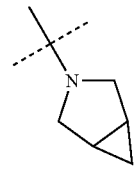

group, and
R$^4$ is a methyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a C$_1$-C$_3$-haloalkyl group
R$^2$ is a hydrogen atom or halogen atom;
R$^3$ is a 5- to 10-membered heteroaryl group which is optionally substituted one or more times with a group independently selected from an amino group, a chlorine atom, a fluorine atom, a trifluormethyl group, and a difluormethyl group,
R$^4$ is a C$_1$-C$_3$-alkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a $C_1$-$C_3$-haloalkyl group
- $R^2$ is a hydrogen atom;
- $R^3$ is a 5- to 10-membered heteroaryl group which is optionally substituted one or more times with a group independently selected from an amino group, a chlorine atom, a fluorine atom, a trifluormethyl group, and a difluoromethyl group,
- $R^4$ is a $C_1$-$C_3$-alkyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a $C_1$-$C_3$-haloalkyl group
- $R^2$ is halogen atom;
- $R^3$ is a 5- to 10-membered heteroaryl group which is optionally substituted one or more times with a group independently selected from an amino group, a chlorine atom, a fluorine atom, a trifluormethyl group, and a difluoromethyl group,
- $R^4$ is a $C_1$-$C_3$-alkyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a $C_1$-$C_3$-haloalkyl group
- $R^2$ is a hydrogen atom;
- $R^3$ is a 5- to 10-membered heteroaryl group which is optionally substituted one or more times with a group independently selected from an amino group, a chlorine atom, a fluorine atom, a trifluormethyl group, and a difluoromethyl group,
- $R^4$ is a methyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom;
- $R^3$ is a 5 to 10-membered heteroaryl group which is optionally substituted one or more times with a group independently selected from an amino group, a chlorine atom, a fluorine atom, a trifluormethyl group, and a difluoromethyl group,
- $R^4$ is a $C_1$-$C_3$-alkyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom
- $R^3$ is a 5- to 10-membered heteroaryl group which is optionally substituted one or more times with a group independently selected from an amino group, a chlorine atom, a fluorine atom, a trifluormethyl group, and a difluoromethyl group,
- $R^4$ is a methyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom
- $R^3$ is a 5- to 6-membered heteroaryl group which is optionally substituted one or more times with a group independently selected from an amino group, a chlorine atom, a fluorine atom, a trifluormethyl group, and a difluoromethyl group,
- $R^4$ is a methyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom
- $R^3$ is a 5-membered heteroaryl group which is optionally substituted one or more times with a group independently selected from an amino group, a chlorine atom, a fluorine atom, a trifluormethyl group, and a difluoromethyl group,
- $R^4$ is a methyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom
- $R^3$ is a 6-membered heteroaryl group which is optionally substituted one or more times with a group independently selected from an amino group, a chlorine atom, a fluorine atom, a trifluormethyl group, and a difluoromethyl group,
- $R^4$ is a methyl group;
- or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
- $R^1$ is a trifluoromethyl group
- $R^2$ is a hydrogen atom
- $R^3$ is a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, and a 5- to 6-membered heteroaryl group, and
- $R^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a NR$^5$R$^6$ group, or a

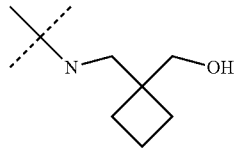

group,
R$^4$ is a methyl group;
R$^5$ is a hydrogen atom
R$^6$ is selected from
   a C$_1$-C$_3$-alkyl group which is optionally substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group,
   and
   a C$_5$-C$_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a NR$^5$R$^6$ group,
R$^4$ is a methyl group;
R$^5$ is a hydrogen atom
R$^6$ is selected from
   a C$_1$-C$_3$-alkyl group which is optionally substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group,
   and
   a C$_5$-C$_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a trifluoromethyl group
R$^2$ is a hydrogen atom
R$^3$ is a

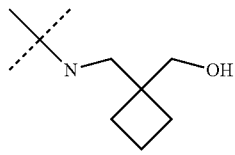

group,
R$^4$ is a methyl group;
R$^5$ is a hydrogen atom
R$^6$ is selected from
   a C$_1$-C$_3$-alkyl group which is optionally substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group,
   and
   a C$_5$-C$_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a hydrogen atom, a halogen atom, a C$_1$-C$_3$-alkyl group, or a C$_1$-C$_3$-haloalkyl group; with the proviso that both, R$^1$ and R$^2$, may not be a hydrogen atom at the same time; or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a hydrogen atom, a halogen atom, a C$_1$-C$_3$-alkyl group, or a C$_1$-C$_3$-haloalkyl group; with the proviso that both, R$^1$ and R$^2$, may not be a hydrogen atom at the same time with the exception if R$^3$ is an ortho substituted phenyl group, both, R$^1$ and R$^2$, may also be a hydrogen atom;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a hydrogen atom, a fluorine atom, a chlorine atom, a methyl group, or a trifluoromethyl group;
   with the proviso that both, R$^1$ and R$^2$, may not be a hydrogen atom at the same time;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R$^1$ is a hydrogen atom, a fluorine atom, a chlorine atom, a methyl group, or a trifluoromethyl group;
   with the proviso that both, R$^1$ and R$^2$, may not be a hydrogen atom at the same time with the exception if $R^3$ is an ortho substituted phenyl group, both, $R^1$ and $R^2$, may also be a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, or a $C_1$-$C_3$-haloalkyl group;

with the proviso that both, $R^1$ and $R^2$, may not be a hydrogen atom at the same time;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, or a $C_1$-$C_3$-haloalkyl group;

with the proviso that both, $R^1$ and $R^2$, may not be a hydrogen atom at the same time with the exception if $R^3$ is an ortho substituted phenyl group, both, $R^1$ and $R^2$, may also be a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom;

with the proviso that both, $R^1$ and $R^2$, may not be a hydrogen atom at the same time;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom;

with the proviso that both, $R^1$ and $R^2$, may not be a hydrogen atom at the same time with the exception if $R^3$ is an ortho substituted phenyl group, both, $R^1$ and $R^2$, may also be a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is $C_1$-$C_3$-alkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a $C_1$-$C_3$-alkyl group or a $C_1$-$C_3$-haloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a halogen atom, or a $C_1$-$C_3$-haloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a halogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is $C_1$-$C_3$-haloalkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, a $C_1$-$C_3$-haloalkyl group; and $R^2$ is a hydrogen atom or a halogen atom;

with the proviso that both, $R^1$ and $R^2$, may not be a hydrogen atom at the same time or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^1$ is a hydrogen atom, a halogen atom, a $C_1$-$C_3$-alkyl group, a $C_1$-$C_3$-haloalkyl group; and $R^2$ is a hydrogen atom or a halogen atom;

with the proviso that both, $R^1$ and $R^2$, may not be a hydrogen atom at the same time with the exception if $R^3$ is an ortho substituted phenyl group, both, $R^1$ and $R^2$, may also be a hydrogen atom or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^2$ is a hydrogen atom, or a halogen atom;

with the proviso that both, $R^1$ and $R^2$, may not be a hydrogen atom at the same time;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

67

$R^2$ is a hydrogen atom, or a halogen atom;
with the proviso that both, $R^1$ and $R^2$, may not be a hydrogen atom at the same time with the exception if $R^3$ is an ortho substituted phenyl group, both, $R^1$ and $R^2$, may also be a hydrogen atom;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^2$ is a hydrogen atom, a fluorine atom, or a chlorine atom;
with the proviso that both, $R^1$ and $R^2$, may not be a hydrogen atom at the same time;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^2$ is a hydrogen atom, a fluorine atom, or a chlorine atom;
with the proviso that both, $R^1$ and $R^2$, may not be a hydrogen atom at the same time with the exception if $R^3$ is an ortho substituted phenyl group, both, $R^1$ and $R^2$, may also be a hydrogen atom;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^1$ is a trifluormethyl group;
$R^2$ is; a hydrogen atom
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^1$ is; a hydrogen atom
$R^2$ is a trifluormethyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a $C_1$-$C_3$-alkyl group which is substituted one or more times with a group independently selected from a $C_1$-$C_3$-alkyl group, a $C_1$-$C_3$-alkoxy group, a heterocycloalkyl group, and an amino group, which is substituted once or twice with a $C_1$-$C_3$-alkyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a $C_1$-$C_3$-alkyl group which is substituted one or more times with a group independently selected from a $C_1$-$C_3$-alkyl group, a $C_1$-$C_3$-alkoxy group, a heterocycloalkyl group, and an amino group, which is optionally substituted once or twice with a $C_1$-$C_3$-alkyl group,
or a stereoisomer, a tautomer, an N-oxide, a hydrate, a solvate, or a salt thereof, or a salt of a stereoisomer, a salt of a tautomer, a salt of an N-oxide or a mixture of same.

68

In a further embodiment of the first aspect, the present invention includes compounds of formula (I), supra, in which:
$R^3$ is a $C_1$-$C_3$-alkyl group which is substituted one or more times with a group independently selected from a $C_1$-$C_3$-alkyl group, a $C_1$-$C_3$-alkoxy group, a heterocycloalkyl group, and an amino group, which is optionally substituted once or twice with a $C_1$-$C_3$-alkyl group,
with the proviso that methyl is excluded.
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a $C_1$-$C_3$-alkyl group which is substituted one or more times with a group independently selected from a $C_1$-$C_3$-alkoxy group, a heterocycloalkyl group, and an amino group, which is optionally substituted once or twice with a $C_1$-$C_3$-alkyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is selected from a —$(CH_2)_3$—O—$CH_3$ group, a —$CH_2$-(morpholin-4-yl) group, and a —$CH_2$—N$(CH_3)_2$ group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a $C_2$-$C_6$-alkenyl group, which is optionally substituted with a $C_1$-$C_3$-alkoxy group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a halogen atom, a $C_1$-$C_3$-alkyl group, and a $C_1$-$C_3$-haloalkyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times independently with a halogen atom, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a $C_1$-$C_3$-alkyl group, and a $C_1$-$C_3$-haloalkyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times independently with a $C_1$-$C_3$-alkyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times independently with a $C_1$-$C_3$-haloalkyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a fluorine atom, a chlorine atom, a methyl group, a trifluoromethyl group, and a difluoromethyl group
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a fluorine atom, a chlorine atom, a methyl group, a trifluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a fluorine atom, a chlorine atom, and a trifluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted with a chlorine atom, or a trifluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted with a fluorine atom, or a trifluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a group independently selected from a fluorine atom, and a chlorine atom,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted one or more times with a fluorine atom,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted with a fluorine atom,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted with a chlorine atom,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
$R^3$ is a phenyl group which is substituted with a trifluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 4- to 6-membered heterocycloalkyl group which is substituted one or more times with a group independently selected from a fluorine atom, a hydroxy group, and a C₁-C₃-alkyl group, a

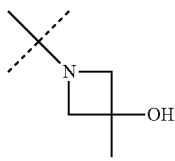

group, a

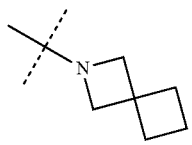

group, a

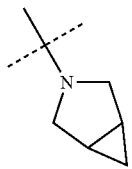

group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 5- to 10-membered heteroaryl group which is substituted one or more times with a group independently selected from an amino group, a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 5- to 10-membered heteroaryl group which is substituted one or more times with a group independently selected from an amino group, a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same with the proviso that one unsubstituted. R³=piperidin, morpholin, pyridine are excluded.

In a further embodiment of the first aspect, the present invention includes compounds of formula (I), supra, in which:

R³ is a 5- to 6-membered heteroaryl group which is substituted one or more times with a group independently selected from an amino group, a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 5- to 6-membered heteroaryl group which is substituted one or more times with a group independently selected from a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same with the proviso that one unsubstituted. R³=piperidin, morpholin, pyridine are excluded.

In a further embodiment of the first aspect, the present invention includes compounds of formula (I), supra, in which:

R³ is a 5- to 6-membered heteroaryl group which is substituted one or more times with a group independently selected from a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 5- to 6-membered heteroaryl group which is substituted one or more times with a group independently selected from a trifluormethyl group and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 5-membered heteroaryl group which is substituted one or more times with a group independently selected from an amino group, a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R³ is a 6-membered heteroaryl group which is substituted one or more times with a group independently selected from an amino group, a chlorine atom, a fluorine atom, a trifluormethyl group, and a difluoromethyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a 7-membered heteroaryl group which is substituted one or more times with a group independently selected from an amino group, a chlorine atom, a fluorine atom, a trifluormethyl group, and a difluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a 8-membered heteroaryl group which is substituted one or more times with a group independently selected from an amino group, a chlorine atom, a fluorine atom, a trifluormethyl group, and a difluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a 9-membered heteroaryl group which is substituted one or more times with a group independently selected from an amino group, a chlorine atom, a fluorine atom, a trifluormethyl group, and a difluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a 10-membered heteroaryl group which is substituted one or more times with a group independently selected from an amino group, a chlorine atom, a fluorine atom, a trifluormethyl group, and a difluoromethyl group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, and a 5- to 6-membered heteroaryl group, with the proviso that an unsubstituted methoxy group is excluded;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a NR⁵R⁶ group, and
R⁵ is a hydrogen atom;

R⁶ is selected from
a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group,
with the proviso that a $C_1$-$C_3$-alkyl group which is substituted with an unsubstituted pyridyl group or an unsubstituted furanyl group and a hydroxy group as a single substituent is excluded
and
a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is a

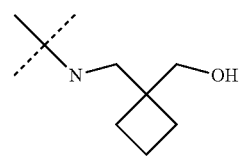

group,
or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:
R³ is selected from a —(CH₂)₃O—CH₃ group, a —CH₂-(morpholin-4-yl) group, a —CH₂—N(CH₃)₂ group, a —CH=C(CH₃)₂ group, a —CH=CH—CH₂—O—CH₃ group, a —CH=CH—CH₂—O—CH₂—CH₃ group, a cyclopent-1-en-1-yl group, a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group, a 3-hydroxy-piperidin-1-yl group, a 4,4-difluoro-piperidin-1-yl group, a 4-ethyl-4-hydroxy-piperidin-1-yl group, a

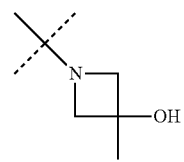

group, a 3-hydroxy-3-methyl-pyrrolidin-1-yl group, a 4-methyl-piperazin-1-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group, a —NH—CH$_2$-(pyrazol-3-yl) group, a —NH—CH$_2$-(pyrazol-5-yl) group, a —NH—CH$_2$-pyrazin-2-yl group, a —NH—CH$_2$—CH(OH)CF$_3$ group, a

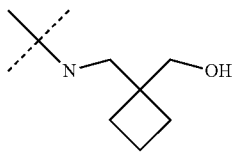

group, a NH-cyclopentyl group, a —O—(CH$_2$)$_2$—CH$_3$ group, a —O—(CH$_2$)$_2$—C(CH$_3$)$_3$ group, a —O—(CH$_2$)—CH(CH$_3$)—OH group, a —O—(CH$_2$)—C(CH$_3$)$_2$—OH group, a —O—CH$_2$-(pyrazol-3-yl) group, a —O—(CH$_2$)$_2$—O—CH$_3$ group, a —O—CH$_2$-cyclobutyl group, a —O—CH$_2$-tetrahydofuran-2-yl group, a —O—(CH$_2$)$_2$—CF$_3$ group, and a —O—(CH$_2$)$_3$CH$_3$ group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^4$ is a hydrogen atom or a C$_1$-C$_3$-alkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^4$ is a hydrogen atom;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^4$ is a C$_1$-C$_3$-alkyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^4$ is a methyl group;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^4$ is a methyl group with S-configuration;

or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^6$ is
a C$_1$-C$_3$-alkyl group which is substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^6$ is
a C$_1$-C$_3$-alkyl group which is substituted one or more times with a group independently selected from a 5- to 6-membered heteroaryl group, a C$_1$-C$_3$-alkoxy group, a hydroxy group, a C$_1$-C$_3$-haloalkyl group, and a C$_4$-C$_6$-cycloalkyl group which itself is optionally substituted with a C$_1$-C$_3$-hydroxyalkyl group,
with the proviso that a C$_1$-C$_3$-alkyl group which is substituted with an unsubstituted pyridyl group or an unsubstituted furanyl group or a hydroxy group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^6$ is
a C$_1$-C$_3$-alkyl group which is substituted one or more times with a group independently selected from a 5- to 6-membered heteroaryl group, a C$_1$-C$_3$-haloalkyl group, and a C$_4$-C$_6$-cycloalkyl group which itself is optionally substituted with a C$_1$-C$_3$-hydroxyalkyl group, or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

R$^6$ is
a C$_1$-C$_3$-alkyl group which is substituted one or more times with a group independently selected from a 5- to 6-membered heteroaryl group, a C$_1$-C$_3$-haloalkyl group, and a C$_4$-C$_6$-cycloalkyl group which itself is optionally substituted with a C$_1$-C$_3$-hydroxyalkyl group,
with the proviso that a C$_1$-C$_3$-alkyl group which is substituted with an unsubstituted pyridyl group or an unsubstituted furanyl group and a hydroxy group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^6$ is a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, with the proviso that a $C_1$-$C_3$-alkyl group which is substituted with an unsubstituted pyridyl group or an unsubstituted furanyl group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^6$ is a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, with the proviso that a $C_1$-$C_3$-alkyl group which is substituted with an unsubstituted pyridyl group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^6$ is a $C_1$-$C_3$-alkyl group which is substituted one or more times with a group independently selected from a 5- to 6-membered heteroaryl group, a $C_1$-$C_3$-haloalkyl group, and a $C_4$-$C_6$-cycloalkyl group which itself is optionally substituted with a $C_1$-$C_3$-hydroxyalkyl group, with the proviso that a $C_1$-$C_3$-alkyl group which is substituted with an unsubstituted furanyl group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In a further embodiment of the first aspect, the present invention includes compounds of formula (I), supra, in which:

$R^6$ is a $C_1$-$C_3$-alkyl group which is substituted one or more times with a group independently selected from a $C_1$-$C_3$-haloalkyl group, and a $C_4$-$C_6$-cycloalkyl group which itself is optionally substituted with a $C_1$-$C_3$-hydroxyalkyl group, with the proviso that a $C_1$-$C_3$-alkyl group which is substituted with a hydroxy group as a single substituent is excluded or a stereoisomer, a tautomer, an N-oxide, a hydrate, a solvate, or a salt thereof, or a salt of a stereoisomer, a salt of a tautomer, a salt of an N-oxide or a mixture of same.

In further embodiments, the present invention includes compounds of formula (I), or a stereoisomer, a tautomer, an N-oxide, a hydrate, a solvate, or a salt thereof, or a salt of a stereoisomer, a salt of a tautomer, a salt of an N-oxide or a mixture of same.

In further embodiments, the present invention includes compounds of formula (I), or a tautomer, an N-oxide, or a salt thereof or a salt of a tautomer or a salt of an N-oxide or a mixture of same In further embodiments, the present invention includes compounds of formula (I), or a tautomer, or a salt thereof, or a salt of a tautomer, or a mixture of same In yet further embodiments, the present invention includes compounds of formula (I), or a salt thereof or a mixture of same In further embodiments, the present invention includes compounds of formula (I), which are salts.

In further embodiments, the present invention includes compounds of formula (I), which are amine salts or salts with organic acids.

In further embodiments, the present invention includes compounds of formula (I), which are salts with organic acids particularly formed with pharmaceutically acceptable organic acids.

In further embodiments, the present invention includes compounds of formula (I), which are amine salts, particularly formed with pharmaceutically acceptable amines.

In further embodiments, the present invention includes compounds of formula (I), which are a tautomer, or a salt thereof or a salt of a tautomer or a mixture of same In further embodiments, the present invention includes compounds of formula (I), which are a an N-oxide, or a salt thereof or a salt of an N-oxide or a mixture of same In a particular further embodiment of the first aspect, the present invention includes combinations of two or more of the above mentioned embodiments under the heading "further embodiments of the first aspect of the present invention".

Furthermore it is understood that the invention includes any subcombination of the disclosed single embodiments herein for certain residues or combined with a subcombination of residues of formula (I) as outlined in the claims.

The present invention includes any sub-combination within any embodiment or aspect of the present invention of compounds of general formula (I), supra.

The present invention includes any sub-combination within any embodiment or aspect of the present invention of intermediate compounds of general formula (IV) and (V).

The present invention includes the compounds of general formula (I) which are disclosed in the Example Section of this text, infra.

General Synthesis of Compounds of General Formula (I)

A. General Synthesis Route

The compounds according to the invention of general formula (I) can be prepared according to the following schemes 1, 2, and 3. The schemes and procedures described below illustrate synthetic routes to the compounds of general formula (I) of the invention and are not intended to be limiting. It is clear to the person skilled in the art that the order of transformations as exemplified in schemes 1, 2, and 3 can be modified in various ways. The order of transformations exemplified in these schemes is therefore not intended to be limiting. In addition, interconversion of any of the substituents, $R^1$, $R^2$, $R^3$, or $R^4$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

Five routes for the preparation of compounds of general formula (I) are described in schemes 1, 2, and 3.

Route 1 (Grignard Route)

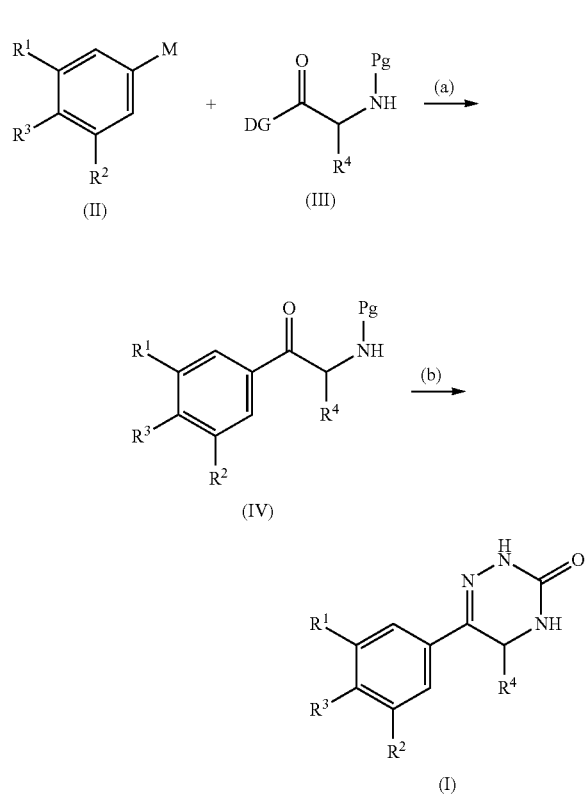

especially for $R^4$=$CH_3$:

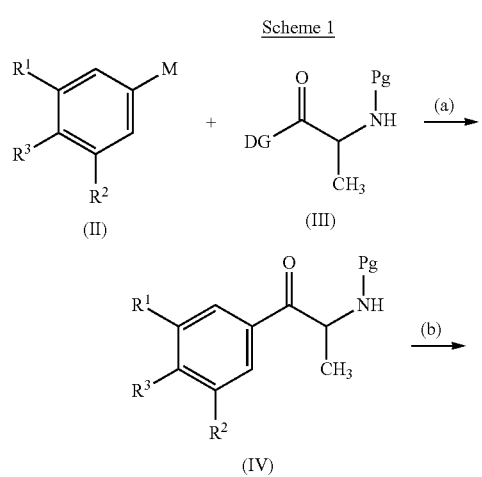

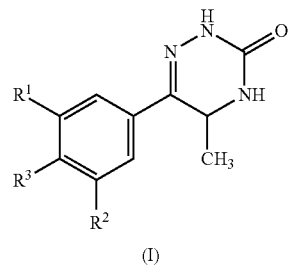

Scheme 1: Route for the preparation of compounds of general formula (I) from compounds of formulae (II) and (III), in which $R^1$, $R^2$, $R^3$ (potential containing functional groups suitably protected), and $R^4$ have the meaning as defined supra and M is a metal-containing group, such as Li, or MgBr, or MgCl; and DG is a group displaceable from compounds of formula (III) by reactants of formula (II), particularly but not limited to $N(OCH_3)CH_3$ (Weinreb amide); and PG is a protecting group suitable for amine groups, e.g. a carbamate group such as tert-butyl-carbamate (Boc). Compounds of formulae (II) and (III) are known to the person skilled in the art and can be readily prepared from commercially available precursors by known methods.

(a) THF, −20° C.-20° C., 1 h-24 h, (b) 1. $H_2NNHCOOCH_3$, HCl, MeOH; 2. TFA, DCM, 0° C.-20° C.; 3. NaOEt/EtOH or NaOMe/MeOH, 20° C.;

Compounds of formula (I) containing chiral centers can be optionally separated by methods known to the person skilled in the art, such as e.g. chiral chromatography, to obtain individual enantiomers or diastereomers.

Compounds (II) are either commercially available or can be prepared according to procedures available from the public domain, as understandable to the person skilled in the art. Specific examples are described in the Experimental Section.

Route 2: Alternative Synthesis of a Subset of Compounds of General Formula (I), Compounds of General Formula (Ia)

Part I: Synthesis of Intermediate Compounds of Formula (V)

Scheme 2

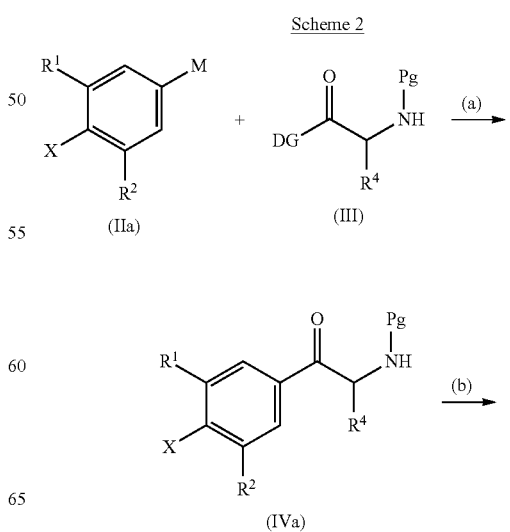

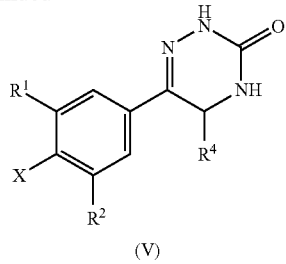

Scheme 2: Route for the preparation of intermediate compounds of formula (V), in which $R^1$, $R^2$ and $R^4$ have the meaning as defined supra; the meaning of X is as defined below in context of Scheme 3 and the paragraphs (i), (j), (k) for compounds of formula (V).

(a) THF, −20° C.-20° C., 1 h-24 h, (b) 1. $H_2NNHCOOCH_3$, HCl, MeOH; 2. TFA, DCM, 0° C.-20° C.; 3. NaOEt/EtOH or NaOMe/MeOH, 20° C.;

Compounds of formula (V) containing chiral centers can be optionally separated by methods known to the person skilled in the art, such as e.g. chiral chromatography, to obtain individual enantiomers or diastereomers.

Part II: Conversion of the Intermediate Compounds of Formula (V) into Compounds of General Formula (Ia):

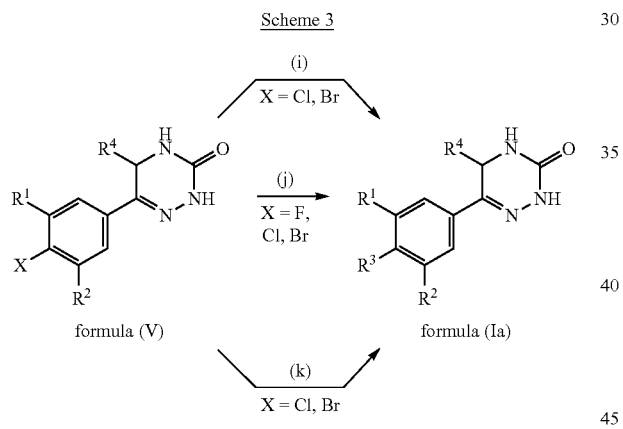

(i): $R^3$ = substituted alkyl group, an optionally substituted alkenyl group, a cycloalkenyl group, a substituted phenyl group, or a substituted heteroaryl group,
(j), (k): $R^3$ = $NR^5R^6$, opt. subst. N-linked heterocycloalkyl, or subst. N-linked heteroaryl.

Scheme 3: Route for the preparation of compounds of general formula (I) via formula (V) in which $R^1$, $R^2$ and $R^4$ have the meaning as defined supra, in which $R^3$ in general formula (Ia) is selected from a substituted methyl group, an optionally substituted alkenyl group, a cycloalkenyl group, a substituted phenyl group, and a substituted heteroaryl group as defined in more detail below in paragraph (i) for $R^x$; or $R^3$ is $NR^5R^6$, or an optionally substituted N-linked heterocycloalkyl group, or a substituted N-linked heteroaryl group, as defined in more detail below in paragraph (j) and (k), respectively; and in which the terms "N-linked heterocycloalkyl", and "N-linked heteroaryl" refer to a 4- to 6-membered heterocycloalkyl, or a heteroaryl group, as defined for $R^3$ supra, which is bonded to the rest of the molecule via a nitrogen atom which constitutes a ring atom of said heterocycloalkyl, or heteroaryl group.

(i) Route 2 Via Suzuki Coupling with Organoboron Compounds

Compounds of general formula (I), in which $R^3$ is $R^x$ as defined below for the formulae (VIa), (VIb), and (VIc), can be obtained by reacting intermediate compounds of formula (V), in which
X is Cl, Br, (as reflected in scheme 3), or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;
$R^1$ or $R^2$ are as defined supra but are different from Cl, Br, I, and
$R^4$ is as defined supra,
with boronic acids $R^xB(OH)_2$ (formula (VIa)), or boronic esters $R^xB(OR^y)_2$ (formula (VIb)), or tetrafluoroborate salts $R^xBF_4$ (formula (VIc)),
in the presence of
a base, such as potassium carbonate or potassium acetate,
a palladium catalyst, such as dichlorobis(triphenylphosphine)palladium, tetrakistriphenylphosphinepalladium (0), palladium(II) acetate/triscyclohexylphosphine, tris (dibenzylideneacetone)dipalladium, bis (diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis (diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl) [2-(2'-amino-1,1'-biphenyl)]palladium(II), palladium (II) acetate and (2-dicyclohexylphosphino-2',4',6'-triisopropyl-1,1'-biphenyl)[2-(2'-amino-1,1'-biphenyl)] palladium(II), particularly chloro(2-dicyclohexylphosphino-2',4',6'-triisopropyl-1,1'-biphenyl)[2-(2'-amino-1,1'-biphenyl)]palladium(II),
and, optionally, an additional ligand, such as 2-(dicyclohexylphosphino)-2',4',6'-triisopropylbiphenyl,
in a solvent, such as dioxane, toluene, or water, or a mixture thereof, under nitrogen or argon atmosphere, at 80° C.-120° C., for 2 h-7 d;
whereby
$R^x$ is
a methyl group which is substituted one or more times with a group selected from a $C_1$-$C_3$-alkyl group, a $C_1$-$C_3$-alkoxy group, a heterocycloalkyl group, and an amino group which is substituted once or twice by a $C_1$-$C_3$-alkyl group, a $C_2$-$C_6$-alkenyl group, which is optionally substituted with a $C_1$-$C_3$-alkoxy group,
a $C_5$-$C_6$-cycloalkenyl group,
a phenyl group which is substituted one or more times with a group independently
selected from a fluorine atom, a chlorine atom, a methyl group, a trifluoromethyl group,
a 5 to 10-membered heteroaryl group which is optionally substituted one or more times with a group independently selected from an amino group, a chlorine atom, a fluorine atom, a trifluormethyl group, and a difluoromethyl group,
$R^y$ is $C_1$-$C_6$-alkyl, or the two residues $R^y$ together are a $C_2$-$C_6$-alkylene group, particularly —$C(CH_3)_2$—$C(CH_3)_2$— to form a pinacol ester.

As readily understood by the person skilled in the art, compounds of general formula (I) prepared e.g. by a Suzuki coupling, in which $R^3$ features a group comprising an olefinic double bond (e.g. if $R^3$ is alkenyl, cycloalkenyl or), can be readily converted into compounds in which $R^3$ features the corresponding saturated group (e.g. alkyl, cycloalkyl, heterocycloalkyl) by methods known to the person skilled in the art, such as catalytic hydrogenolysis using a suitable catalyst, such as palladium on carbon.

(j) Route 2 via nucleophilic aromatic substitution to introduce $R^3$ substituents selected from —$NR^5R^6$, a N-linked 4- to 6-membered heterocycloalkyl group, and a N-linked heteroaryl group, whereby the term "N-linked" is to be understood as described in context of Scheme 3.

Compounds of general formula (I), in which $R^3$ is selected from —$NR^5R^6$, a N-linked 4- to 6-membered heterocycloalkyl group, and a N-linked heteroaryl group, whereby the term "N-linked" is to be understood as described in context of Scheme 3, and in which the terms "4- to 6-membered heterocycloalkyl", and "heteroaryl" are constituted and optionally substituted as defined for $R^3$, supra, can be obtained by reacting intermediate compounds of formula (V), in which $R^4$ has the meaning as defined supra, X is F, Cl, or Br (as reflected in scheme 3), and if X is Cl or Br, $R^1$ or $R^2$ can not be F; particularly X is F;

$R^1$ and $R^2$ have the meaning as defined supra, with the proviso that if X is Cl or Br, $R^1$ or $R^2$ can not be F, and with the proviso that at least one of $R^1$ and $R^2$ exerts an electron withdrawing effect; particularly, $R^1$ is selected from fluorine, and —$CF_3$, and $R^2$ is hydrogen or fluorine; more particularly, $R^1$ is —$CF_3$ and $R^2$ is hydrogen;

with a corresponding amine, optionally as a free base or as a salt, such as a hydrochloride salt, selected from $HNR^5R^6$ and a cyclic amine featuring one N—H as a ring atom, said cyclic amine being selected from a 4- to 6-membered heterocycloalkane, and a heteroarene containing one N—H as a ring atom, respectively, optionally in the presence of a base, such as triethylamine, DIPEA, or cesium carbonate, in an inert solvent, such as THF, $CH_3CN$, DMF or DMSO, at optionally elevated temperatures ranging from RT to 160° C., particularly from 60° C. to 150° C., for 2 h-7 d;

whereby $R^5$ is H, and $R^6$ is selected from a $C_1$-$C_3$-alkyl group which is substituted one or more times with a group independently selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

(k) Alternative Route via transition metal catalyzed, particularly palladium catalyzed amination, to introduce $R^3$ substituents selected from —$NR^5R^6$, a N-linked heterocycloalkyl group, and a N-linked heteroaryl group, whereby the term "N-linked" is to be understood as described in context of Scheme 3.

Compounds of general formula (I), in which $R^3$ is selected from —$NR^5R^6$, a N-linked 4- to 6-membered heterocycloalkyl group, and a N-linked heteroaryl group, whereby the term "N-linked" is to be understood as described in context of Scheme 3, and in which the terms "4- to 6-membered heterocycloalkyl", and "heteroaryl" are constituted and optionally substituted as defined for $R^3$, supra, can be obtained by reacting intermediate compounds of formula (V), in which X is Cl, Br, (as reflected in scheme 3), or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ or $R^2$ are as defined supra but are different from $C_1$, Br; particularly, $R^1$ is —$CF_3$ and $R^2$ is hydrogen;

$R^4$ has the meaning as defined supra, with a corresponding amine, optionally as a free base or as a salt, such as a hydrochloride salt, selected from $HNR^5R^6$ and a cyclic amine featuring one N—H as a ring atom, said cyclic amine being selected from a 4- to 6-membered heterocycloalkane, and a heteroarene containing one N—H as a ring atom, respectively, in the presence of a base, such as potassium phosphate or cesium carbonate, a palladium catalyst, such as tris (dibenzylideneacetone)dipalladium(0), a ligand, such as 2-(dicyclohexylphosphino)-2',4',6'-triisopropyl-1,1'-biphenyl or 2,2'-bis(diphenylphosphino)-1,1'-binaphthalene, in an inert solvent, such as dioxane or toluene, at elevated temperatures ranging from 60-160° C., for 2 h-7 d;

whereby $R^5$ is H, and $R^6$ is selected from a $C_1$-$C_3$-alkyl group which is substituted one or more times with a group independently selected from a 5 to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

The thus obtained compounds of formula (I) containing chiral centers can be optionally separated by chiral chromatography to obtain individual enantiomers or diastereomers.

Route 3: Alternative Synthesis of a Subset of Compounds of General Formula (I), Compounds of General Formula (Ib) Wherein $R^3$ is an Optionally Substituted Alkoxy Group Part I: Synthesis of Intermediate Compounds of Formula (V)

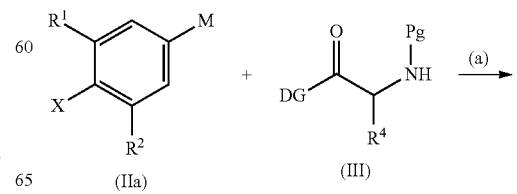

(IIa)    (III)

85
-continued (IVa)

(V)

and especially for R=CH₃:

Scheme 4

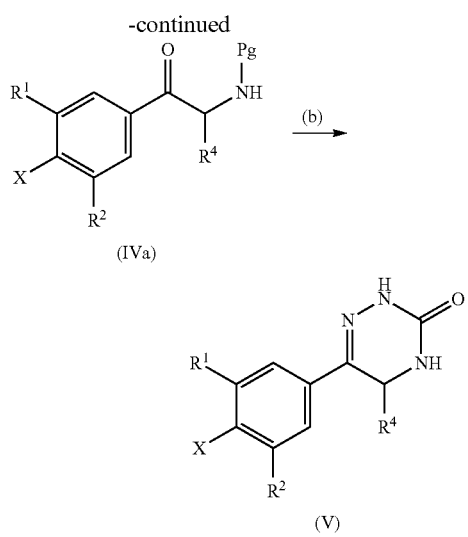

(IIa)  (III)

(IVa)

(V)

Scheme 4: Route for the preparation of intermediate compounds of formula (V), in which $R^1$, $R^2$ and $R^4$ have the meaning as defined supra; the meaning of X is as defined below in context of Scheme 5 and the paragraphs (m), (n), (o) for compounds of formula (V).

(a) THF, −20° C.-20° C., 1 h-24 h, (b) 1. H₂NNHCOOCH₃, HCl, MeOH; 2. TFA, DCM, 0° C.-20° C.; 3. NaOEt/EtOH or NaOMe/MeOH, 20° C.;

Compounds of formula (V) containing chiral centers can be optionally separated by methods known to the person skilled in the art, such as e.g. chiral chromatography, to obtain individual enantiomers or diastereomers.

86
Part II: Conversion of the Intermediate Compounds of Formula (V) into Compounds of General Formula (Ib):

Scheme 5 formula (V)   formula (Ib)

(m), (n), (o):

$R^7$ = a $C_1$-$C_6$-alkyl group which is optionally substituted with a group independently selected from $C_1$-$C_3$-haloalkyl group, a hydroxy group, a $C_1$-$C_3$-alkyloxy group, a $C_4$-$C_6$-cycloalkyl group, a 4- to 6-membered heterocycloalkyl group, a 5- to 6-membered heteroaryl group, with the proviso that an unsubstituted methyl group is excluded; and Pg2 is a protecting group suitable for hydroxy groups, e.g. a benzyl group.

Scheme 5: Route for the preparation of compounds of general formula (Ib) via formula (V) in which $R^1$, $R^2$ and $R^4$ have the meaning as defined supra, in which $R^3$ in general formula (I) is a $C_1$-$C_6$-alkoxy group which is optionally substituted with a group selected from $C_1$-$C_3$-haloalkyl group, a hydroxy group, a $C_1$-$C_3$-alkyoxy group, a $C_4$-$C_6$-cycloalkyl group, a 4 to 6-membered heterocycloalkyl group, and a 5 to 6-membered heteroaryl group, with the proviso that an unsubstituted methoxy group is excluded.

(m) Route 3 Via Nucleophilic Aromatic Substitution to Introduce $R^3$ Substituents, Wherein $R^3$ is an Optionally Substituted Alkoxy Group Compounds of general formula (Ib), can be obtained by reacting intermediate compounds of formula (V), in which $R^4$ has the meaning as defined supra, X is F or Cl (as reflected in scheme 5), and if X is Cl, $R^1$ or $R^2$ can not be F; particularly X is F;

$R^1$ and $R^2$ have the meaning as defined supra, with the proviso that if X is Cl, $R^1$ or $R^2$ can not be F, and with the proviso that at least one of $R^1$ and $R^2$ exerts an electron withdrawing effect; particularly, $R^1$ is selected from fluorine and —CF₃, and $R^2$ is hydrogen or fluorine; more particularly, $R^1$ is —CF₃ and $R^2$ is hydrogen;

with a corresponding alcohol $R^7$—OH ($R^7$ as defined above), optionally as the alcohol or as an alkoxide salt, such as a sodium or potassium salt, optionally in the presence of a strong base, such as potassium tert-butoxide, or sodium hydride, or sodium metal, optionally in an inert solvent, such as THF or DMF, optionally in the presence of a base, such as cesium carbonate, in a solvent, such as DMSO, optionally at elevated temperatures ranging from RT to 160° C., particularly from 60° C. to 150° C., for 2 h-7 d;

whereby $R^7$ is a $C_1$-$C_6$-alkyl group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methyl group is excluded.

(n) Alternative Route Via Transition Metal Catalyzed, Particularly Palladium Catalyzed Amination, to Introduce $R^3$ Substituents, Wherein $R^3$ is an Optionally Substituted Alkoxy Group Compounds of general formula (Ib), can be obtained by reacting intermediate compounds of formula (V), in which
X is Cl, Br, I, (as reflected in scheme 5), or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;
$R^1$ or $R^2$ are as defined supra but are different from Cl, Br, I; particularly, $R^1$ is —$CF_3$ and $R^2$ is hydrogen;
$R^4$ has the meaning as defined supra,
with a corresponding alcohol $R^7$—OH,
in the presence of a base, such as potassium phosphate or cesium carbonate, a palladium catalyst, such as [(2-di-tert-butylphosphino-3,6-dimethoxy-2',4',6'-triisopropyl-1,1'-biphenyl)-2-(2'-amino-1,1'-biphenyl)]palladium(II) methanesulfonate or [(2-di-tert-butylphosphino-3-methoxy-6-methyl-2',4',6'-triisopropyl-1,1'-biphenyl)-2-(2-aminobiphenyl)] palladium(II) methanesulfonate, optionally a ligand, such as 2-di(tert-butyl)phosphino-2',4',6'-triisopropyl-3-methoxy-6-methylbiphenyl or 2-(di-tert-butylphosphino)-2',4',6'-triisopropyl-3,6-dimethoxy-1,1'-biphenyl, in an inert solvent, such as dioxane or toluene, at elevated temperatures ranging from 60-160° C., for 2 h-7 d;
whereby
$R^7$=is a $C_1$-$C_6$-alkyl group which is optionally substituted with a group selected from a $C_1$-$C_3$-haloalkyl group, a hydroxy group, a $C_1$-$C_3$-alkyoxy group, a $C_4$-$C_5$-cycloalkyl group, a 4 to 6-membered heterocycloalkyl group, and a 5 to 6-membered heteroaryl group, with the proviso that an unsubstituted methyl group is excluded.

The thus obtained compounds of formula (I) containing chiral centers can be optionally separated by chiral chromatography to obtain individual enantiomers or diastereomers.

(o) Alternative Route Via Mitsunobu Reaction, to Introduce $R^3$ Substituents, Wherein $R^3$ is an Optionally Substituted Alkoxy Group Compounds of general formula (Ib), can be obtained in a two step procedure (Step o-1 (Removal of the protecting group Pg2), followed by Step o-2 (Mitsunobu reaction)).

(o-1) Compounds of general formula (V), where X is —OH, can be obtained by reacting intermediate compounds of formula (V), in which
X is OPg2, where Pg2 is a protecting group suitable for hydroxy groups, e.g. a benzyl group;
$R^1$, $R^2$, and $R^4$ has the meaning as defined supra,
with hydrogen gas, in the presence of a palladium catalyst, such as Palladium on carbon, in a solvent, such as ethanol, at temperatures ranging from room temperature to 60° C., for 2 h-3 d, at hydrogen pressure ranging from 1 bar to 10 bar, particularly 1 bar.

(o-2) Compounds of general formula (Ib), can be obtained by reacting intermediate compounds of formula (V), in which X is —OH,
$R^1$, $R^2$, and $R^4$ has the meaning as defined supra,
with a corresponding alcohol $R^7$—OH,
in the presence of an dialkylazodicarboxylate, particularly diisopropylazodicarboxylate, a phosphine, such as triphenylphosphine, in an inert solvent, such as THF, at temperatures ranging from 0° C. to room temperature, for 2 h-3 d;
whereby
$R^7$=is a $C_1$-$C_6$-alkyl group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4 to 6-membered heterocycloalkyl group, and a 5 to 6-membered heteroaryl group, with the proviso that an unsubstituted methyl group is excluded.

The thus obtained compounds of formula (I) containing chiral centers can be optionally separated by chiral chromatography to obtain individual enantiomers or diastereomers.

In accordance with a second aspect, the present invention includes methods of preparing compounds of general formula (I) as defined supra, said methods comprising the step of allowing an intermediate compound of general formula (IV)

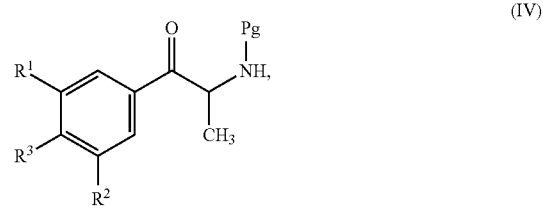

(IV)

in which $R^1$, $R^2$ and $R^3$ are as defined for the compound of general formula (I) as defined supra, and Pg means a protecting group readily suitable for an amine group, such as a carbamate group, more particularly a tert. butoxycarbamate group,
to react in
step 1): with $H_2NNHCOOCH_3$, under acidic conditions (e.g. hydrochloric acid) in an alcoholic solution e.g. in methanol, and in
step 2): with trifluoroacetic acid (TFA) in dichloromethan (DCM), at 0° C.-20° C.; and in
step 3): under basic conditions at room temperature, particularly with NaOEt/EtOH or NaOMe/MeOH, at 20° C.;
thereby giving a compound of general formula (I)

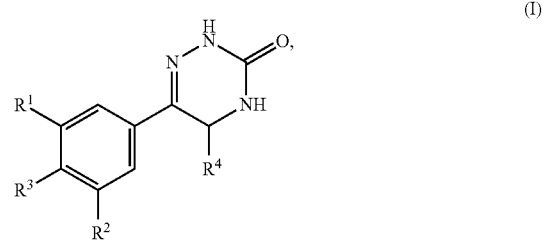

(I)

in which $R^1$, $R^2$, $R^3$ and $R^4$ are as defined in any one of the claims 1-8 or any embodiment supra.

In accordance with a third aspect, the present invention includes methods of preparing compounds of general formula (I) as defined supra, said methods comprising the step of allowing an intermediate compound of general formula (II):

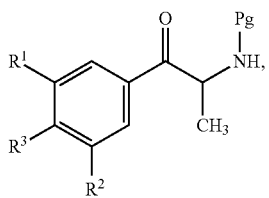

in which R¹, R² and R³ are as defined for the compound of general formula (I) according to claim 1, where functional groups contained in R³ optionally are suitably protected such as e.g. a hydroxy group being protected by PG2 as defined supra, and Pg means a protecting group for an amine group, to react in step 1): with H₂NNHCOOCH₃, under acidic conditions in an alcoholic solution, and in step 2): with trifluoroacetic acid (TFA) in dichloromethan (DCM), at 0° C.-20° C.; and in step 3): under basic conditions at room temperature, particularly with NaOEt/EtOH or NaOMe/MeOH, at 20° C.;

optionally deprotecting any still protected functional groups, thereby giving a compound of general formula (I)

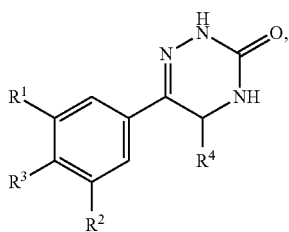

in which R¹, R², R³ and R⁴ are as defined in any one of the claims 1-8 or any embodiment supra.

then optionally converting said compound into solvates, salts and/or solvates of such salts using the corresponding (i) solvents and/or (ii) bases or acids.

In a further embodiment the invention provides a method of preparing a compound of formula (I) as described above further comprising a step for separating enantiomers or diastereoisomers.

In just a further embodiment the invention provides compounds of formula (Ia)

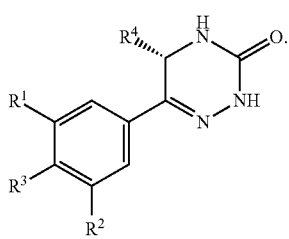

In just a further embodiment the invention provides compounds of formula (Ib)

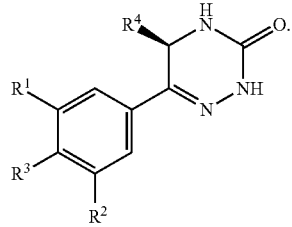

Methods of obtaining compounds of formula (Ia) and formula (Ib) from compounds of formula (I) are known by the person with ordinary skill, such as e.g. chromatography, optionally chiral chromatography.

The present invention includes methods of preparing compounds of the present invention of general formula (I), said methods comprising the steps as described in the Experimental Section herein.

In accordance with a fourth aspect, the present invention includes intermediate compounds which are useful for the preparation of the compounds of general formula (I), supra.

Particularly, the invention includes the intermediate compounds of general formula (IV):

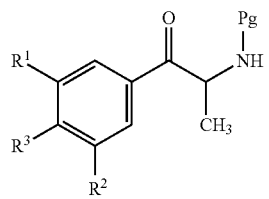

in which R¹, R², R³ and R⁴ are as defined for the compound of general formula (I) supra.

In accordance with a fifth aspect, the present invention includes the use of said intermediate compounds for the preparation of a compound of general formula (I) as defined supra.

Particularly, the inventions includes the use of intermediate compounds of general formula (I)

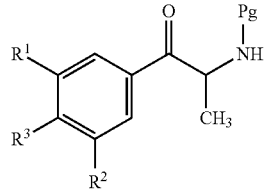

in which R¹, R², R³ and R⁴ and Pg are as defined for the compound of general formula (I) supra, for the preparation of a compound of general formula (I) as defined supra.

Particularly, the invention includes the intermediate compounds of general formula (V):

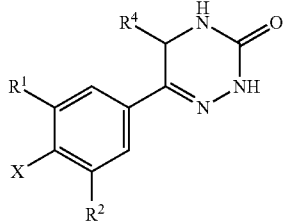

in which $R^1$, $R^2$, $R^3$ and $R^4$ are as defined for the compound of general formula (I) supra and X a halogen atom or OPg2 whereby Pg2 is a suitable protective group, such as a benzyl group.

In accordance with a fifth aspect, the present invention includes the use of said intermediate compounds for the preparation of a compound of general formula (I) as defined supra.

Particularly, the invention includes the use of intermediate compounds of general formula (V)

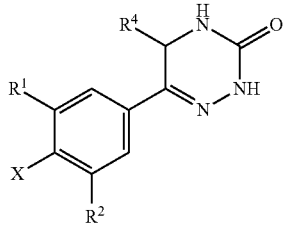

in which $R^1$, $R^2$, and $R^4$ are as defined for the compound of general formula (I) supra, and X is a halogen atom or OPg2 whereby Pg2 is a benzyl group, for the preparation of a compound of general formula (I) as defined supra.

The present invention includes the intermediate compounds which are disclosed in the Example Section of this text, infra.

The present invention includes any sub-combination within any embodiment or aspect of the present invention of intermediate compounds of general formula (IV) and (V), supra.

The compounds of general formula (I) of the present invention can be converted to any salt, particularly pharmaceutically acceptable salts, as described herein, by any method which is known to the person skilled in the art. Similarly, any salt of a compound of general formula (I) of the present invention can be converted into the free compound, by any method which is known to the person skilled in the art.

Methods and Administration

Compounds of general formula (I) of the present invention demonstrate a valuable pharmacological spectrum of action, which could not have been predicted. Compounds of the present invention have surprisingly been found to effectively inhibit cell proliferation and it is likely therefore that said compounds may be used for the treatment or prophylaxis of diseases, particularly hyperproliferative diseases in humans and animals.

More particularly the compounds of formula (I) are suitable for the treatment of a patient having a cancer that is found to be sensitive to treatment with a phosphodiesterase 3A/B, (PDE3A and/or B)-SLF12 complex modulator by detecting co-expression of PDE3A and/or PDE3B and Schlafen 12 (SLFN12) and/or SLFN12L mRNA, polynucleotides or polypeptides and/or a lack of decrease in expression of CREB3L1 mRNA, polynucleotides or polypeptides in a cancer cell derived from such patients. The compounds of formula (I) are selective for cancer cell killing while minimizing enzymatic inhibition of PDE3A and PDE3B Compounds of the present invention can be utilized to inhibit tumor growth by inducing a SLFN12 complex formation. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disease.

Further Definitions

By "alteration" is meant a change (increase or decrease) in the expression levels, structure, or activity of a gene or polypeptide as detected by standard art known methods such as those described herein. As used herein, in one embodiment an alteration includes an about 10% change in expression levels, particularly an about 25% change, more particularly an about 40% change, and most particularly an about 50% or greater change in expression levels. In certain embodiments an alteration includes a 10% or less (including 10%) change in expression levels, particularly a 25% or less (including 25%) change, more particularly 40% or less (including 40%) change, and most particularly a 50% or less (including 50%) or greater change in expression levels. In other embodiments an alteration includes a 9%-11% (including 9% and 11%) change in expression levels, particularly a 10%-25% (including 10% and 25%) change, more particularly a 25%-40% (including 25% and 40%) change, and most particularly a 40%-50% (including 40%-50%) or greater than 50% (including 50%) change in expression levels. In other certain embodiments an alteration includes a 9%-11% (including 9% and 11%) change in expression levels, particularly a 22%-28% (including 22% and 28%) change, more particularly a 35%-45% (including 35% and 45%) change, and most particularly a 45%-55% (including 45%-55%) or a greater or equal to 55% change in expression levels By "fragment" is meant a portion of a polypeptide or nucleic acid molecule. This portion contains, particularly, at least about 10%, about 20%, about 30%, about 40%, about 50%, about 60%, about 70%, about 80%, or about 90% of the entire length of the reference nucleic acid molecule or polypeptide. In certain embodiments this portion contains, particularly, at least 9%-11% (including 9% and 11%), 18%-22% (including 18% ands 22%), 27%-33% (including 27% and 33%), 36%-44% (including 36% and 44%), 45%-55% (including 45% and 55%), 54%-66% (including 54% and 66%), 63%-77% (including 63% and 77%), 72%-88% (including 72% and 88%), or 81%-99% (including 81% and 99%) of the entire length of the reference nucleic acid molecule or polypeptide A fragment may contain about 10, about 20, about 30, about 40, about 50, about 60, about 70, about 80, about 90, about 100, about 200, about 300, about 400, about 500, about 600, about 700, about 800, about 900, or about 1000 nucleotides or amino acids. In certain embodiments a fragment may contain 9-11, about 18-22, 27-33, 36-44, 45-55, 54-66, 63-77, 72-88, 81-99, 90-110, 180-220, 270-330, 360-440, 450-550, 540-660, 630-770, 720-880, 810-990, or 900-1100 nucleotides or amino acids (including for each the mentioned limitation e.g. for "9-11" means including 9 and 11.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide. In some embodiments, the modulator of PDE3A and/or PDE3B polypeptide is a compound of formula (I).

By "hyperproliferative disease" is meant a disease, such as cancer, associated with inappropriately high levels of cell division, inappropriately low levels of apoptosis, or both.

Hyperproliferative diseases include, but are not limited to, hematopoietic and benign hyperproliferative diseases.

"Hematopoietic hyperproliferative diseases" also known as myoproliferative diseases include e.g. polycythemia vera, essential thrombocytosis, thrombocytosis, primary myelofibrosis, and others.

"Benign hyperproliferative diseases" include for example, endometriosis, leiomyoma and benign prostate hyperplasia.

Hyperproliferative diseases include, but are not limited to, for example: psoriasis, keloids, and other hyperplasias affecting the skin, benign prostate hyperplasia (BPH), solid tumours, such as cancers of the brain, breast, digestive tract, eye, head and neck, liver, respiratory tract, reproductive organs, skin, thyroid, parathyroid, urinary tract, and their distant metastases. Those diseases also include leukaemias, lymphomas, and sarcomas.

"Solid tumours" are such as e.g. cancers of the breast, brain, digestive tract, eye, head and neck, liver, parathyroid, reproductive organs, respiratory tract, skin, thyroid, urinary tract, and their distant metastases. Those diseases also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of brain cancers include, but are not limited to, brain stem and hypothalmic glioma, glioblastoma, cerebellar and cerebral astrocytoma, medulloblastoma, ependymoma, as well as neuroectodermal and pineal tumour. In one embodiment brain cancer especially includes glioblastoma, astrocytoma, anaplastic astrocytoma, and primitive neuroectodermal tumor.

Tumours of the digestive tract include, but are not limited to, anal, colon, colorectal, oesophageal, gallbladder, gastric, pancreatic, rectal, small-intestine, and salivary gland cancers.

Eye cancers include, but are not limited to, intraocular melanoma and retinoblastoma.

Head-and-neck cancers include, but are not limited to, laryngeal, hypopharyngeal, nasopharyngeal, oropharyngeal cancer, lip and oral cavity cancer and squamous cell.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Examples of cancers of the respiratory tract include, but are not limited to, small-cell and non-small-cell lung carcinoma, as well as bronchial adenoma and pleuropulmonary blastoma.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the urinary tract include, but are not limited to, bladder, penile, kidney, renal pelvis, ureter, urethral and human papillary renal cancers.

Skin cancers include, but are not limited to, squamous cell carcinoma, Kaposi's sarcoma, malignant melanoma, Merkel cell skin cancer, and non-melanoma skin cancer.

Leukemias include, but are not limited to, acute myeloid leukemia, acute lymphoblastic leukemia, chronic lymphocytic leukemia, chronic myelogenous leukemia, and hairy cell leukemia. More particularly Leucemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system. Particularly Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, osteosarcoma, malignant fibrous histiocytoma, lymphosarcoma, and rhabdomyosarcoma.

Any compositions or methods provided herein can be combined with one or more of any of the other compositions and methods provided herein.

The term "treating" or "treatment" as stated throughout this document is used conventionally, and includes for example the management or care of a subject for the purpose of combating, alleviating, reducing, relieving, and/or improving the condition of a disease or disease, such as a carcinoma. These diseases have been well characterized in humans, but also exist with a similar etiology in other mammals, and can be treated by administering pharmaceutical compositions of the present invention. It will be appreciated that, although not precluded, treating a disease or condition does not require that the disease, condition or symptoms associated therewith be completely eliminated.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents and/or anti-cancer agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other anti-cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death.

In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Compounds of the present invention can be utilized to inhibit tumor growth by inducing a SLFN12 complex formation. This method comprises administering to a mammal in need thereof, including a human, an amount of a compound of this invention, or a pharmaceutically acceptable salt, isomer, polymorph, metabolite, hydrate, solvate or ester thereof; which is effective to treat the disease.

The present invention also includes methods of treating hyperproliferative diseases, cancer diseases.

These diseases have been well characterized in humans, but also exist with a similar etiology in other mammals, and can be treated by administering pharmaceutical compositions of the present invention.

The compounds of the present invention can be used in particular in therapy and prevention, i.e. prophylaxis, of hyperproliferative diseases, cancer diseases.

Another aspect of the invention is a method for controlling cancer (e.g., through treatment and/or prophylaxis) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

Particularly in some embodiments, the present invention includes a method of treating a hyperproliferative disease, more particularly cancer, comprising administering an effective amount of at least one compound of general formula (I) according to any one of claims 1-6.

A method of inhibiting hyperproliferation of a cancer cell is also provided, wherein the method comprises contacting a cancer cell with a compound of general formula (I). The cancer cell may be in vitro or in vivo.

In accordance with a further aspect, the present invention includes a method of treatment or prophylaxis of diseases, in particular hyperproliferative diseases, particularly cancer diseases, using an effective amount of a compound of general formula (I), as described supra, or stereoisomers, tautomers, N-oxides, hydrates, solvates, and salts thereof, particularly pharmaceutically acceptable salts thereof, or mixtures of same.

In some embodiments, the method of treatment and/or prophylaxis of a hyperproliferative disease in a subject may comprise administering to the subject an effective amount of a compound of general formula (I). The hyperproliferative disease may be, for example, cancer (such as e.g., tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor. etc.).

In some embodiments, the method of treatment and/or prophylaxis of a hyperproliferative disease in a subject may comprise administering to the subject an effective amount of a compound of general formula (I). The hyperproliferative disease may be, for example, cancer (such as e.g., cervix cancer and melanoma etc.).

Furthermore in some embodiments, the present invention includes a method of treating cancer, particularly tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor. comprising administering an effective amount of at least one compound of formula (I) according to any one of claims 1-6.

Furthermore in some embodiments, the present invention includes a method of treating cancer, particularly cervix cancer and melanoma comprising administering an effective amount of at least one compound of formula (I) according to any one of claims 1-6.

Furthermore in some embodiments, the present invention includes a method of treating cancer, particularly tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor. comprising administering an effective amount of at least one compound of formula (I) according to any one of claims 1-6.

Furthermore in some embodiments, the present invention includes a method of treating cancer, particularly cervix cancer and melanoma comprising administering an effective amount of at least one compound of formula (I) according to any one of claims 1-6.

In accordance with a further aspect, the present invention includes compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative diseases.

In some embodiments, the present invention includes a method of using a compound of general formula (I) for the treatment of diseases.

The pharmaceutical activity of the compounds according to the invention can be explained by their activity as SLFN12 complex inducer.

In accordance with a further aspect, the present invention includes the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular hyperproliferative diseases, particularly cancer diseases.

In accordance with a further aspect, the present invention includes compounds of formula (I) according to any of claims 1-6 without any disclaimer for the use in the treatment of cancer, in particular for the use in the treatment of brain cancer, cervical cancer, skin cancer and ovarian cancer, more particularly for the use in the treatment of brain cancer, cervical cancer, and skin cancer.

In accordance of another aspect, the present invention includes compounds of formula (I),
wherein
$R^1$ is a hydrogen atom, a halogen atom, a $C_1$-$C_3$-alkyl group, or a $C_1$-$C_3$-haloalkyl group;
$R^2$ is a hydrogen atom, or a halogen atom;
$R^3$ is
  a $C_1$-$C_3$-alkyl group which is substituted one or more times with a group independently selected from a $C_1$-$C_3$-alkyl group, a $C_1$-$C_3$-alkoxy group, a heterocycloalkyl group, and an amino group which is substituted once or twice with a $C_1$-$C_3$-alkyl group,
  a $C_2$-$C_6$-alkenyl group, which is optionally substituted with a $C_1$-$C_3$-alkoxy group,
  a $C_5$-$C_6$-cycloalkenyl group,
  a phenyl group which is substituted one or more times with a group independently selected from halogen atom, $C_1$-$C_3$-alkyl group, and a $C_1$-$C_3$-haloalkyl group,
  a 4- to 6-membered heterocycloalkyl group which is substituted one or more times with a group independently selected from a fluorine atom, a hydroxy group, and a $C_1$-$C_3$-alkyl group,
  a

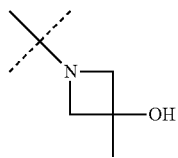

group, a

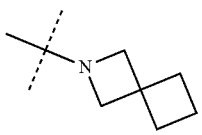

group, a

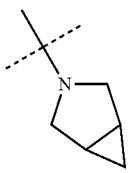

group,
a 5- to 10-membered heteroaryl group which is substituted one or more times with a group independently selected from an amino group, a halogen atom, and a $C_1$-$C_3$-haloalkyl group,
a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group,
a $NR^5R^6$ group, and
a

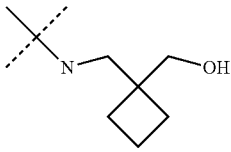

group,
$R^4$ is a hydrogen atom or a $C_1$-$C_3$-alkyl group;
$R^5$ is a hydrogen atom
$R^6$ is selected from
a $C_1$-$C_3$-alkyl group which is substituted one or more times with a group selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group,
and
a $C_5$-$C_6$-cycloalkyl group;
or a stereoisomer, a tautomer, an N-oxide, a hydrate, a solvate, or a salt thereof, or a salt of a stereoisomer, a salt of a tautomer, a salt of an N-oxide or a mixture of same.

In accordance with a further aspect, the present invention includes the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular hyperproliferative diseases, particularly cancer diseases.

In some embodiments, the present invention includes use of the compounds of general formula (I) for the manufacture of a medicament for the treatment of a hyperproliferative disease, particularly cancer and more particularly tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor.

In some embodiments, the present invention includes use of the compounds of general formula (I) for the manufacture of a medicament for the treatment of a hyperproliferative disease, particularly cancer and more particularly cervix cancer and melanoma.

In some embodiments, the present invention includes use of the compounds of general formula (I) for the manufacture of a medicament for the treatment of a hyperproliferative disease, particularly cancer and more particularly brain cancer, cervix cancer, and melanoma.

In some embodiments, the present invention includes use of the compounds of general formula (I) for the manufacture of a medicament for the treatment of a hyperproliferative disease, particularly cancer and more particularly brain cancer, cervix cancer, melanoma and ovarian cancer.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6.

In some embodiments, the present invention includes compound of general formula (I) according to any one of claims 1 to 6 for use in a method of treatment or prophylaxis of a disease.

Particularly in some embodiments, the present invention includes compounds of general formula (I) for use in a method of treating a hyperproliferative disease, more particularly wherein the hyperproliferative disease is cancer, and yet even more particularly wherein the cancer disease is cervix cancer and melanoma.

Particularly in some embodiments, the present invention includes compounds of general formula (I) for use in a method of treating a hyperproliferative disease, more particularly wherein the hyperproliferative disease is cancer, and yet even more particularly wherein the cancer disease is brain cancer, cervix cancer, melanoma and ovarian cancer.

In some embodiments the present invention provides for compounds of general formula (I) for use in a method of treating cancer, particularly where the cancer disease is cervix cancer and melanoma.

In some embodiments the present invention provides for compounds of general formula (I) for use in a method of treating cancer, particularly where the cancer disease is brain cancer, cervix cancer, melanoma and ovarian cancer.

In accordance with a further aspect, the present invention includes use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, particularly a medicament, for the prophylaxis or treatment of diseases, in particular hyperproliferative diseases, particularly cancer diseases.

In accordance with a further aspect, the present invention includes pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore includes pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophilisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphized and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophilisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides, fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention includes pharmaceutical combinations, in particular medicaments, comprising at least one compound of general formula (I) of the present invention and at least one or more further active ingredients, in particular for the treatment and/or prophylaxis of a hyperproloferative disease, e.g. cancer.

Particularly, the present invention includes a pharmaceutical combination, which comprises:
  one or more first active ingredients, in particular compounds of general formula (I) as defined supra, and
  one or more further active ingredients, in particular anti-cancer agent(s).

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of anti-cancer agents include:

131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, alpharadin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, cemiplimab, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tislelizumab, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, such as e.g. cancer diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and particularly from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will particularly be from 0.01 to 200 mg/kg of total body weight. The average daily rectal dosage regimen will particularly be from 0.01 to 200 mg/kg of total body weight. The average daily vaginal dosage regimen will particularly be from 0.01 to 200 mg/kg of total body weight. The average daily topical dosage regimen will particularly be from 0.1 to 200 mg administered between one to four times daily. The transdermal concentration will particularly be that required to maintain a daily dose of from 0.01 to 200 mg/kg. The average daily inhalation dosage regimen will particularly be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Section—NMR Spectra

NMR peak forms are stated as they appear in the spectra, possible higher order effects have not been considered.

Nuclear magnetic resonance (NMR) spectra were recorded on a Bruker (300 or 400 MHz $^1$H, 75 or 101 MHz $^{13}$C) spectrometer. Proton, fluorine, and carbon chemical shifts are reported in ppm ($\delta$) referenced to the NMR solvent. Data are reported as follows: chemical shifts, multiplicity (br=broad, s=singlet, d=doublet, t=triplet, q=quartet, m=multiplet; coupling constant(s) in Hz).

The $^1$H-NMR data of selected compounds are listed in the form of $^1$H-NMR peaklists. Therein, for each signal peak the $\delta$ value in ppm is given, followed by the signal intensity, reported in round brackets. The $\delta$ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within patent applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

Experimental Section—Abbreviations

The following table 1 lists the abbreviations used in this paragraph and in the Examples section as far as they are not explained within the text body. Other abbreviations have their meanings customary per se to the skilled person.

TABLE 1

Abbreviations

| | |
|---|---|
| [α] | specific rotation value |
| d | doublet (NMR coupling pattern) |
| CDI | 1,1'-Carbonyldiimidazole |
| DAD | Diode array detector |
| DIPEA | N,N-diisopropylethylamine |
| DMF | dimethylformamide |
| DMSO | dimethylsulfoxide |
| ESI | electrospray ionisation (MS) |
| EtOAc | Ethyl acetate |
| EtOH | Ethanol |
| LC-MS | liquid chromatography coupled to mass spectrometry |
| M | Molar or molecular Mass |
| m | multiplet (NMR coupling pattern) |
| Me | Methyl |
| MeOH | methanol |
| MeOH | methanol |
| MHz | Megahertz |
| MS | mass spectrometry |
| NMR | nuclear magnetic resonance |
| pH | Potential of Hydrogen |
| q | quartet (NMR coupling pattern) |
| $R_t$ | retention time |
| RT | room temperature |
| s | singlet (NMR coupling pattern) |
| t | triplet (NMR coupling pattern) |
| tBuOH | tert-butanol |
| THF | Tetrahydrofuran |
| TFA | Trifluoroacetic acid |
| UPLC | Ultra Performance Liquid Chromatography |
| UPLC-MS | Ultra High Preformance Liquid Chromatography Mass Spectroscopy |
| UV | ultraviolet |
| WL | wavelength |
| δ | NMR shift in ppm |

The following table lists the abbreviations used herein.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP—NH® in combination with a Biotage autopurifier system (SP4® or Isolera Four®) and eluents such as gradients of hexane/ethyl acetate or DCM/methanol.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Analytical UPLC Methods:

Method 1:

Instrument: Waters Acquity UPLC-MS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:

Instrument: Waters Acquity UPLC-MS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Analytical UPLC Methods:
Method 3:
Instrument: Waters Acquity UPLC-MS SingleQuad; Colum: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm Method 4:
Instrument: Waters Acquity UPLC-MS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm Experimental Section—Intermediates Intermediate 1 tert-Butyl N-[(1S)-2-[methoxy(methyl)amino]-1-methyl-2-oxo-ethyl]carbamate

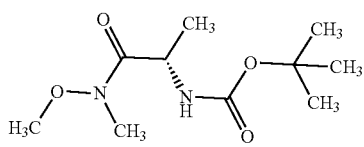 [SMILES: CON(C)C(=O)[C@H](C)NC(=O)OC(C)(C)C]

To a solution of N-(tert-butoxycarbonyl)-L-alanine (250 g, 1.32 mol) in DCM (1.25 L) was added CDI (257 g, 1.59 mol, 1.20 eq). The reaction mixture was stirred at 25-30° C. for 1 hr. N-methoxymethanamine hydrochloride salt (155 g, 1.59 mol) was added to the mixture. Then DIPEA (512 g, 3.96 mol, 690 mL) was added and the mixture was stirred at 25~30° C. for 17 hrs. TLC (Petroleum ether:EtOAc=1:1) showed the starting material (Rf=0.15) was consumed and one new spot (Rf=0.55) was formed. The reaction mixture was quenched by addition water (1.00 L) and extracted with CH$_2$Cl2 (500 mL). The organic phase was washed with brine, dried over anhydrous sodium sulfate, filtered, and concentrated under reduced pressure to give the target compound (261 g, crude) as a white solid which was sufficiently pure for the next reaction.

$^1$H NMR (400 MHz, CDCl$_3$) δ 5.35-5.17 (m, 1H), 4.85-4.54 (m, 1H), 3.77 (s, 3H), 3.21 (s, 3H), 1.44 (s, 9H), 1.32 (d, J=6.8 Hz, 3H)

Intermediate 2 tert-Butyl N-[(1S)-2-[4-fluoro-3-(trifluoromethyl)phenyl]-1-methyl-2-oxo-ethyl]carbamate

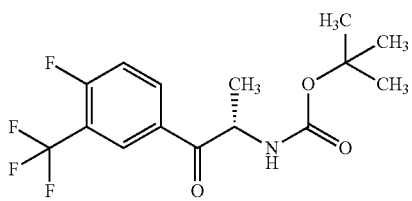 [SMILES: C[C@H](NC(=O)OC(C)(C)C)C(=O)c1ccc(F)c(C(F)(F)F)c1]

A solution of 31.2 g (129 mmol) of 4-bromo-1-fluoro-2-(trifluoromethyl)benzene in 200 mL of THF was added slowly to 3.10 g (129 mmol) of magnesium turnings vigorously stirred in 10 mL of THF. An exotherm appeared after the addition of a few mL of bromide solution, which was added at such a rate to maintain warming. Once the addition was complete the mixture was stirred until it cooled to room temperature. The Grignard reagent formed was then added via syringe to a solution of 15.0 g of tert-butyl N-[(1S)-1-[methoxy(methyl)carbamoyl]ethyl]carbamate (64.5 mmol, Intermediate 1) in 250 mL of THF cooled in an ice bath and the mixture was stirred overnight, warming to room temperature. The dark solution was cooled with an ice bath and then quenched with saturated NH$_4$Cl solution and transferred to a separatory funnel with EtOAc. The EtOAc layer was removed, dried (MgSO$_4$) and concentrated to a brown oil. Addition of hexane produced brown solids which were filtered and rinsed with hexane to collect 16.2 g of product (75%). $^1$H NMR (400 MHz, CDCl$_3$) δ 8.30 (d, J=6.6 Hz, 1H), 8.27-8.18 (m, 1H), 7.35 (t, J=9.2 Hz, 1H), 5.41 (d, J=7.2 Hz, 1H), 5.27 (p, J=7.1 Hz, 1H), 1.47 (s, 9H), 1.42 (d, J=7.1 Hz, 3H). $^{19}$F NMR (376 MHz, CDCl$_3$) δ−61.72 (d, J=12.7 Hz), −105.66 (q, J=12.5 Hz). $^{13}$C NMR (101 MHz, CDCl$_3$) δ 197.01, 164.21-161.17 (m), 155.13, 134.59 (d, J=9.9 Hz), 130.82 (d, J=3.4 Hz), 128.33, 121.96 (q, J=272.6 Hz), 119.29 (qd, J=33.8, 13.2 Hz), 117.62 (d, J=21.3 Hz), 80.10, 50.93, 28.27, 19.06. Mass 336 (M+1).

Intermediate 3

(5S)-6-[4-fluoro-3-(trifluoromethyl)phenyl]-5-methyl-4,5-dihydro-1,2,4-triazin-3(2H)-one

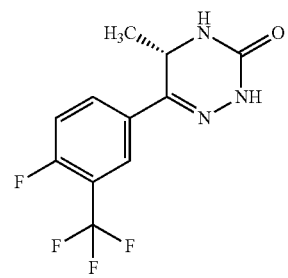 [SMILES: C[C@@H]1NC(=O)NN=C1c1ccc(F)c(C(F)(F)F)c1]

To 3.15 g of tert-butyl (S)-(1-(4-fluoro-3-(trifluoromethyl)phenyl)-1-oxopropan-2-yl)carbamate (9.39 mmol) in 10 mL of MeOH was added 927 mg (10.3 mmol) of methoxycarbohydrazide and 10 drops of 0.1 N HCl and this was heated at reflux temperature for 4 h. After cooling and concentration, chromatography with 10-70% EtOAc isolated 2.08 g of intermediate as an approx. 6:1 ratio (54%). $^1$H NMR of major isomer: $^1$H NMR (400 MHz, CDCl$_3$) δ 7.60-7.45 (m, 3H), 7.39 (t, J=9.1 Hz, 1H), 5.20 (s, 1H), 4.57 (p, J=7.0 Hz, 1H), 3.81 (s, 3H), 1.45 (s, 10H), 1.35 (d, J=6.9 Hz, 3H). $^{19}$F NMR (376 MHz, CDCl$_3$) δ −61.54 (d, J=12.6 Hz), −110.76 (q, J=12.5 Hz). To 335 mg of this intermediate (0.823 mmol) dissolved in 10 mL of CH$_2$Cl$_2$ and cooled in an ice bath was added 5 mL of TFA. The ice bath was removed and after 2 h the reaction was concentrated and dissolved in MeOH. Solid NaOEt was added to make the solution basic and the reaction was stirred overnight. The reaction was quenched with saturated NH$_4$Cl solution, rinsed twice with EtOAc, the combined EtOAc layers were dried (MgSO$_4$) and concentrated to an oil which was chromatographed with 0-100% EtOAc to yield 93 mg of product as a white solid (41%). $^1$H NMR (400 MHz, CDCl$_3$) δ 8.13

(s, 1H), 7.96 (dd, J=6.7, 2.1 Hz, 1H), 7.87 (ddd, J=8.4, 4.5, 2.3 Hz, 1H), 7.28 (t, J=9.2 Hz, 1H), 5.84 (s, 1H), 4.72 (qd, J=6.6, 2.8 Hz, 1H), 1.45 (d, J=6.8 Hz, 3H). $^{19}$F NMR (376 MHz, CDCl$_3$) δ −61.61 (d, J=12.6 Hz), −112.36 (q, J=12.7 Hz).

LC-MS (Method 1): R$_t$=1.02 min; MS (ESIpos): m/z=276 [M+H]+

EXPERIMENTAL SECTION—EXAMPLES

Example 1

(5S)-5-methyl-6-{3-(trifluoromethyl)-4-[3-(trifluoromethyl)-1H-pyrazol-1-yl]phenyl}-4,5-dihydro-1,2,4-triazin-3(2H)-one

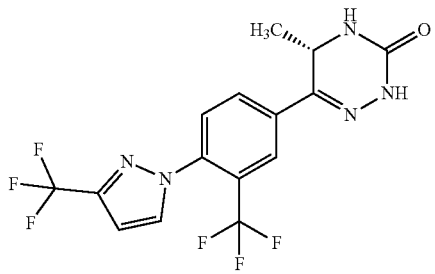 [SMILES: C[C@@H]1NC(=O)NN=C1c1ccc(-n2ccc(C(F)(F)F)n2)c(C(F)(F)F)c1]

To 86 mg of (S)-6-(4-fluoro-3-(trifluoromethyl)phenyl)-5-methyl-4,5-dihydro-1,2,4-triazin-3(2H)-one (0.31 mmol, Intermediate 3) dissolved in 1 mL of DMF was added 168 mg of 3-(trifluoromethyl)-1H-pyrazole (1.24 mmol) and 204 mg of cesium carbonate (0.62 mmoL) and the mixture was heated at 60° C. for 7 h. After cooling, water was added the mixture was rinsed several times with EtOAc, the combined EtOAc was dried (MgSO4) and concentrated to a solid that was recrystallized with CH2Cl2/hexane and then recrystallized from CH2Cl2 to yield 23 mg of white solid (23%). 1H NMR (400 MHz, CDCl$_3$) δ 8.33 (s, 1H), 8.22-8.13 (m, 1H), 7.97 (dd, J=8.3, 1.6 Hz, 1H), 7.78 (s, 1H), 7.66 (d, J=8.4 Hz, 1H), 6.77 (d, J=2.4 Hz, 1H), 5.96 (s, 1H), 4.80 (qd, J=6.6, 3.2 Hz, 1H), 1.48 (d, J=6.8 Hz, 3H). $^{19}$F NMR (376 MHz, CDCl$_3$) δ −59.31, −62.25. Mass 392 (M+1).

The following compounds can be made according to the procedure as described in the synthesis of example 1 above:
(5S)-6-{4-[(2-methoxyethyl)amino]-3-(trifluoromethyl)phenyl}-5-methyl-4,5-dihydro-1,2,4-triazin-3(2H)-one
(5S)-6-[4-(2-azaspiro[3.3]heptan-2-yl)-3-(trifluoromethyl)phenyl]-5-methyl-4,5-dihydro-1,2,4-triazin-3(2H)-one
(5S)-5-methyl-6-[4-{[(2S)-3,3,3-trifluoro-2-hydroxypropyl]amino}-3-(trifluoromethyl)phenyl]-4,5-dihydro-1,2,4-triazin-3(2H)-one
(5S)-5-methyl-6-[4-(morpholin-4-yl)-3-(trifluoromethyl)phenyl]-4,5-dihydro-1,2,4-triazin-3(2H)-one
(5S)-5-methyl-6-{3-(trifluoromethyl)-4-[4-(trifluoromethyl)-2H-1,2,3-triazol-2-yl]phenyl}-4,5-dihydro-1,2,4-triazin-3(2H)-one rel-(5R)-6-{4-[(1R,5R)-3-azabicyclo[3.1.0]hexan-3-yl]-3-(trifluoromethyl)phenyl}-5-methyl-4,5-dihydro-1,2,4-triazin-3(2H)-one
(5S)-6-[4-({[1-(hydroxymethyl)cyclobutyl]methyl}amino)-3-(trifluoromethyl)phenyl]-5-methyl-4,5-dihydro-1,2,4-triazin-3(2H)-one
(5S)-6-[4-(3-fluoro-1H-pyrazol-1-yl)-3-(trifluoromethyl)phenyl]-5-methyl-4,5-dihydro-1,2,4-triazin-3(2H)-one
(5S)-6-[4-(4-ethyl-4-hydroxypiperidin-1-yl)-3-(trifluoromethyl)phenyl]-5-methyl-4,5-dihydro-1,2,4-triazin-3(2H)-one
(5S)-6-{4-[(3S)-3-hydroxypiperidin-1-yl]-3-(trifluoromethyl)phenyl}-5-methyl-4,5-dihydro-1,2,4-triazin-3(2H)-one
(5S)-6-{4-[(3R)-3-hydroxypiperidin-1-yl]-3-(trifluoromethyl)phenyl}-5-methyl-4,5-dihydro-1,2,4-triazin-3(2H)-one
(5S)-5-methyl-6-[4-(piperidin-1-yl)-3-(trifluoromethyl)phenyl]-4,5-dihydro-1,2,4-triazin-3(2H)-one
(5S)-6-{4-[(3R)-3-hydroxy-3-methylpyrrolidin-1-yl]-3-(trifluoromethyl)phenyl}-5-methyl-4,5-dihydro-1,2,4-triazin-3(2H)-one
(5S)-6-{4-[(3S)-3-hydroxy-3-methylpyrrolidin-1-yl]-3-(trifluoromethyl)phenyl}-5-methyl-4,5-dihydro-1,2,4-triazin-3(2H)-one
(5S)-5-methyl-6-[4-(4-methylpiperazin-1-yl)-3-(trifluoromethyl)phenyl]-4,5-dihydro-1,2,4-triazin-3(2H)-one
(5S)-6-[4-(4,4-difluoropiperidin-1-yl)-3-(trifluoromethyl)phenyl]-5-methyl-4,5-dihydro-1,2,4-triazin-3(2H)-one Example 2

(5S)-5-methyl-6-[4-{[(1H-pyrazol-5-yl)methyl]amino}-3-(trifluoromethyl)phenyl]-4,5-dihydro-1,2,4-triazin-3(2H)-one

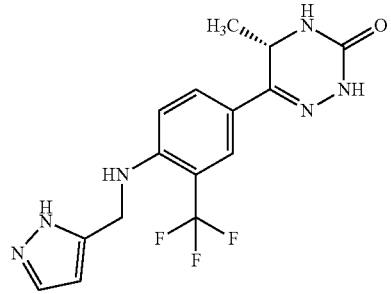 [SMILES: C[C@@H]1NC(=O)NN=C1c1ccc(NCc2ccn[nH]2)c(C(F)(F)F)c1]

To a stirred solution of (5S)-6-[4-fluoro-3-(trifluoromethyl)phenyl]-5-methyl-4,5-dihydro-1,2,4-triazin-3(2H)-one (Intermediate example 3, 150 mg, 545 μmol) in DMSO (1 mL) was added N,N-diisopropylethylamine (280 μl, 1.6 mmol), followed by 1-(1H-pyrazol-5-yl)methanamine (159 mg, 1.64 mmol) and the resulting mixture was stirred at 120° C. overnight. The mixture was purified by mass-triggered preparative HPLC (Method 4) and freeze dried to give an off-white solid.

LC-MS (Method 1): R$_t$=0.80 min; MS (ESIpos): m/z=353 [M+H]$^+$ $^1$H-NMR (400 MHz, DMSO-d6) δ[ppm]: 1.131 (16.00), 1.148 (15.83), 2.518 (2.59), 2.523 (1.63), 2.539 (6.68), 4.417 (4.21), 4.430 (4.19), 4.541 (0.68), 4.558 (2.37), 4.566 (2.38), 4.574 (2.36), 4.582 (2.35), 4.599 (0.67), 6.112 (5.42), 6.117 (5.29), 6.304 (1.44), 6.318 (2.70), 6.332 (1.43), 6.838 (2.57), 6.860 (2.69), 7.367 (3.08), 7.373 (4.22), 7.380 (3.03), 7.613 (0.82), 7.654 (3.19), 7.659 (3.34), 7.676 (2.85), 7.681 (3.03), 7.778 (6.69), 7.784 (6.21), 9.843 (6.23), 9.849 (6.14), 12.642 (0.79).

Example 3

(5S)-6-[4-(3-hydroxy-3-methylazetidin-1-yl)-3-(trifluoromethyl)phenyl]-5-methyl-4,5-dihydro-1,2,4-triazin-3(2H)-one

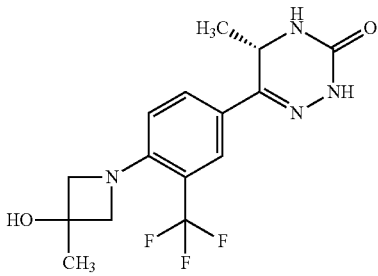 [SMILES: C[C@@H]1NC(=O)NN=C1c1ccc(N2CC(C)(O)C2)c(C(F)(F)F)c1]

Synthesized in analogy to Example 2 from Intermediate 3 and 3-methylazetidin-3-ol trifluoroacetic acid salt (1/1)

LC-MS (Method 1): $R_t$=0.92 min; MS (ESIpos): m/z=343 [M+H]$^+$ $^1$H-NMR (400 MHz, DMSO-d6) δ[ppm]: 1.145 (9.26), 1.163 (9.18), 1.439 (16.00), 2.074 (2.78), 2.518 (3.30), 2.523 (2.08), 2.673 (0.60), 3.864 (1.93), 3.884 (3.92), 3.918 (4.56), 3.938 (2.18), 4.586 (0.41), 4.594 (1.34), 4.602 (1.29), 4.611 (1.29), 4.619 (1.34), 4.627 (0.41), 5.606 (7.30), 6.587 (2.85), 6.609 (2.95), 7.392 (1.60), 7.399 (2.21), 7.405 (1.60), 7.720 (1.82), 7.725 (1.98), 7.742 (1.70), 7.747 (1.87), 7.816 (3.95), 7.822 (3.62), 9.891 (3.60), 9.896 (3.56).

Example 4

(5S)-6-[4-(cyclopentylamino)-3-(trifluoromethyl)phenyl]-5-methyl-4,5-dihydro-1,2,4-triazin-3(2H)-one

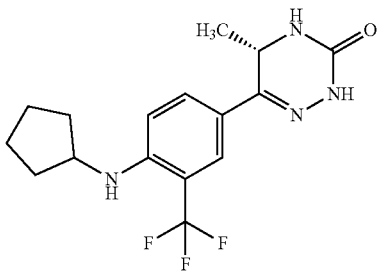 [SMILES: C[C@@H]1NC(=O)NN=C1c1ccc(NC2CCCC2)c(C(F)(F)F)c1]

Synthesized in analogy to Example 2 from Intermediate 3 and cyclopentanamine

LC-MS (Method 1): $R_t$=1.26 min; MS (ESIpos): m/z=341 [M+H]$^+$ $^1$H-NMR (400 MHz, DMSO-d6) δ[ppm]: 1.151 (15.41), 1.168 (16.00), 1.171 (9.66), 1.181 (1.45), 1.187 (2.35), 1.189 (2.98), 1.477 (0.61), 1.491 (1.54), 1.508 (2.30), 1.523 (2.47), 1.539 (3.02), 1.550 (3.36), 1.563 (2.30), 1.573 (2.74), 1.581 (1.91), 1.588 (2.22), 1.591 (2.26), 1.613 (1.22), 1.626 (0.95), 1.631 (0.89), 1.657 (2.60), 1.666 (2.34), 1.672 (3.08), 1.680 (1.97), 1.687 (1.82), 1.711 (0.43), 1.951 (1.06), 1.969 (2.30), 1.986 (9.55), 1.998 (2.67), 2.012 (1.58), 2.518 (2.74), 2.522 (1.67), 2.539 (5.54), 2.590 (0.50), 2.673 (0.93), 3.890 (0.93), 3.906 (1.76), 3.925 (2.76), 3.937 (0.98), 3.999 (0.50), 4.016 (1.58), 4.034 (1.58), 4.052 (0.50), 4.566 (0.59), 4.574 (0.65), 4.583 (2.15), 4.592 (2.10), 4.599 (2.08), 4.608 (2.11), 4.616 (0.65), 4.624 (0.56), 4.959 (2.69), 4.976 (2.63), 6.891 (4.02), 6.913 (4.19), 7.381 (2.52), 7.388 (3.49), 7.394 (2.50), 7.590 (0.46), 7.724 (2.35), 7.729 (2.86), 7.751 (2.97), 7.767 (6.49), 7.772 (4.80), 7.957 (0.50), 8.049 (0.57), 8.063 (0.56), 9.865 (5.58), 9.870 (5.51), 10.197 (0.46), 10.202 (0.48).

Example 5

(5S)-5-methyl-6-[4-{[(2R)-3,3,3-trifluoro-2-hydroxypropyl]amino}-3-(trifluoromethyl)phenyl]-4,5-dihydro-1,2,4-triazin-3(2H)-one

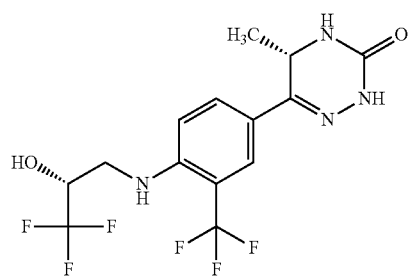 [SMILES: C[C@@H]1NC(=O)NN=C1c1ccc(NC[C@@H](O)C(F)(F)F)c(C(F)(F)F)c1]

Synthesized in analogy to Example 2 from Intermediate 3 and (2R)-3-amino-1,1,1-trifluoropropan-2-ol-hydrogen chloride (1/1)

LC-MS (Method 1): $R_t$=1.00 min; MS (ESIpos): m/z=385 [M+H]$^+$ $^1$H-NMR (400 MHz, DMSO-d6) δ[ppm]: 1.150 (16.00), 1.167 (15.98), 1.181 (0.91), 2.074 (5.53), 2.331 (0.69), 2.518 (4.22), 2.522 (2.62), 2.539 (0.45), 2.673 (0.73), 3.352 (1.52), 3.372 (2.16), 3.392 (1.58), 3.406 (1.22), 3.531 (1.25), 3.542 (1.76), 3.556 (1.47), 3.565 (1.07), 3.577 (1.25), 3.591 (0.89), 3.926 (1.39), 4.216 (0.66), 4.233 (1.24), 4.244 (1.40), 4.260 (1.29), 4.579 (0.66), 4.596 (2.34), 4.604 (2.31), 4.612 (2.29), 4.621 (2.29), 4.638 (0.63), 5.699 (1.58), 5.713 (3.12), 5.727 (1.57), 6.614 (4.85), 6.630 (4.83), 6.920 (4.49), 6.943 (4.67), 7.393 (2.99), 7.400 (4.12), 7.740 (2.77), 7.745 (3.15), 7.767 (3.10), 7.793 (7.08), 7.798 (5.71), 7.957 (0.41), 9.879 (6.45), 9.885 (6.33).

Example 6

(5S)-5-methyl-6-[4-{[(pyrazin-2-yl)methyl]amino}-3-(trifluoromethyl)phenyl]-4,5-dihydro-1,2,4-triazin-3(2H)-one

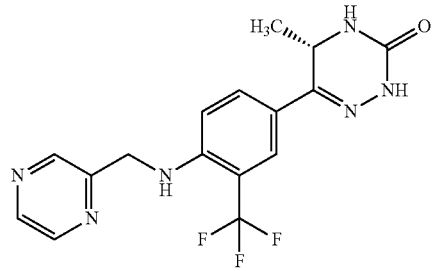 [SMILES: C[C@@H]1NC(=O)NN=C1c1ccc(NCc2cnccn2)c(C(F)(F)F)c1]

Synthesized in analogy to Example 2 from Intermediate 3 and 1-(pyrazin-2-yl)methanamine LC-MS (Method 1): R$_t$=0.92 min; MS (ESIpos): m/z=365 [M+H]$^+$ $^1$H-NMR (400 MHz, DMSO-d6) δ[ppm]: 1.125 (16.00), 1.142 (15.96), 2.322 (1.04), 2.326 (1.35), 2.331 (0.99), 2.522 (4.66), 2.664 (0.97), 2.668 (1.33), 2.673 (0.97), 4.537 (0.69), 4.554 (2.41), 4.562 (2.45), 4.570 (2.45), 4.579 (2.41), 4.595 (0.71), 4.645 (7.56), 4.659 (7.65), 6.679 (1.81), 6.694 (3.71), 6.708 (1.86), 6.737 (4.93), 6.759 (5.10), 7.381 (4.44), 7.654 (3.09), 7.659 (3.27), 7.676 (2.96), 7.680 (3.12), 7.820 (6.78), 7.825 (6.65), 8.543 (7.12), 8.550 (8.35), 8.599 (7.96), 8.602 (10.01), 8.620 (7.03), 8.623 (6.30), 8.626 (6.92), 8.630 (4.91), 9.864 (6.59), 9.869 (6.67).

The following compounds can be made according to the procedure as described in the general synthesis description herein:

According to general synthesis route 1 or route 2i:
(5S)-6-[4'-fluoro-2-(trifluoromethyl)[biphenyl]-4-yl]-5-methyl-4,5-dihydro-1,2,4-triazin-3(2H)-one
(5S)-6-[4-(2-aminopyridin-4-yl)-3-(trifluoromethyl)phenyl]-5-methyl-4,5-dihydro-1,2,4-triazin-3(2H)-one
(5S)-6-{4-[1-(difluoromethyl)-1H-pyrazol-4-yl]-3-(trifluoromethyl)phenyl}-5-methyl-4,5-dihydro-1,2,4-triazin-3(2H)-one
(5S)-6-[4-(5-chloropyridin-2-yl)-3-(trifluoromethyl)phenyl]-5-methyl-4,5-dihydro-1,2,4-triazin-3(2H)-one
(5S)-5-methyl-6-[4-(2-methylprop-1-en-1-yl)-3-(trifluoromethyl)phenyl]-4,5-dihydro-1,2,4-triazin-3(2H)-one
(5S)-6-{4-[(1E)-3-methoxyprop-1-en-1-yl]-3-(trifluoromethyl)phenyl}-5-methyl-4,5-dihydro-1,2,4-triazin-3(2H)-one
(5S)-6-{4-[(E)-2-ethoxyvinyl]-3-(trifluoromethyl)phenyl}-5-methyl-4,5-dihydro-1,2,4-triazin-3(2H)-one
(5S)-5-methyl-6-[4-(pyridin-4-yl)-3-(trifluoromethyl)phenyl]-4,5-dihydro-1,2,4-triazin-3(2H)-one
(5S)-6-[4-(cyclopent-1-en-1-yl)-3-(trifluoromethyl)phenyl]-5-methyl-4,5-dihydro-1,2,4-triazin-3(2H)-one
(5S)-6-[4'-chloro-2-(trifluoromethyl)[biphenyl]-4-yl]-5-methyl-4,5-dihydro-1,2,4-triazin-3(2H)-one
(5S)-6-[3'-fluoro-4'-methyl-2-(trifluoromethyl)[biphenyl]-4-yl]-5-methyl-4,5-dihydro-1,2,4-triazin-3(2H)-one
(5S)-6-{4-[(dimethylamino)methyl]-3-(trifluoromethyl)phenyl}-5-methyl-4,5-dihydro-1,2,4-triazin-3(2H)-one
(5S)-6-(4'-fluoro-2'-methyl[biphenyl]-4-yl)-5-methyl-4,5-dihydro-1,2,4-triazin-3(2H)-one
(5S)-6-[4'-fluoro-2'-(trifluoromethyl)[biphenyl]-4-yl]-5-methyl-4,5-dihydro-1,2,4-triazin-3(2H)-one
(5S)-5-methyl-6-[4-(morpholin-4-ylmethyl)-3-(trifluoromethyl)phenyl]-4,5-dihydro-1,2,4-triazin-3(2H)-one According to general synthesis route 1 or route 2i followed by hydrogenation:
(5S)-6-[4-isobutyl-3-(trifluoromethyl)phenyl]-5-methyl-4,5-dihydro-1,2,4-triazin-3(2H)-one
(5S)-6-[4-(3-methoxypropyl)-3-(trifluoromethyl)phenyl]-5-methyl-4,5-dihydro-1,2,4-triazin-3(2H)-one According to general synthesis route 1 or route 3m/n/o:
(5S)-6-{4-[(2R)-2-hydroxypropoxy]-3-(trifluoromethyl)phenyl}-5-methyl-4,5-dihydro-1,2,4-triazin-3(2H)-one
(5S)-6-[4-(2-hydroxy-2-methylpropoxy)-3-(trifluoromethyl)phenyl]-5-methyl-4,5-dihydro-1,2,4-triazin-3(2H)-one
(5S)-6-{4-[(2S)-2-hydroxypropoxy]-3-(trifluoromethyl)phenyl}-5-methyl-4,5-dihydro-1,2,4-triazin-3(2H)-one
(5S)-5-methyl-6-[4-propoxy-3-(trifluoromethyl)phenyl]-4,5-dihydro-1,2,4-triazin-3(2H)-one
(5S)-6-[4-(2-methoxyethoxy)-3-(trifluoromethyl)phenyl]-5-methyl-4,5-dihydro-1,2,4-triazin-3(2H)-one
(5S)-6-[4-(cyclobutylmethoxy)-3-(trifluoromethyl)phenyl]-5-methyl-4,5-dihydro-1,2,4-triazin-3(2H)-one
(5S)-5-methyl-6-{4-[(2S)-tetrahydrofuran-2-ylmethoxy]-3-(trifluoromethyl)phenyl}-4,5-dihydro-1,2,4-triazin-3(2H)-one
(5S)-5-methyl-6-{4-[(2R)-tetrahydrofuran-2-ylmethoxy]-3-(trifluoromethyl)phenyl}-4,5-dihydro-1,2,4-triazin-3(2H)-one
(5S)-5-methyl-6-[3-(trifluoromethyl)-4-(3,3,3-trifluoropropoxy)phenyl]-4,5-dihydro-1,2,4-triazin-3(2H)-one
(5S)-6-[4-butoxy-3-(trifluoromethyl)phenyl]-5-methyl-4,5-dihydro-1,2,4-triazin-3(2H)-one
(5S)-6-[4-(3,3-dimethylbutoxy)-3-(trifluoromethyl)phenyl]-5-methyl-4,5-dihydro-1,2,4-triazin-3(2H)-one
(5S)-5-methyl-6-[4-(1H-pyrazol-3-ylmethoxy)-3-(trifluoromethyl)phenyl]-4,5-dihydro-1,2,4-triazin-3(2H)-one

EXPERIMENTAL SECTION—BIOLOGICAL ASSAYS

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Assay 1

Cell Proliferation Measurement

The antiproliferative activity of the compounds of the general formula (I) was examined in vitro in human cancer cells. For this purpose, the appropriate number of cells (Hela: 800; SK-MEL-3: 1000; IGR37: 2000; GB-1: 600; H4: 600; PFSK: 1000, DBTRG05MG: 600, DKMG: 1000, SW1783: 1000, M059J: 800, 42-MG-BA: 600, GAMG: 800, LN229: 800, T98G: 800, U118-MG: 1000, U-251MG: 600, YKG1: 800, 92.1: 800, Mel202: 800 were plated in 384-well plates with appropriate growth medium (FCS 10% final (Biochrom; #S 0415); Hela: DMEM/Ham's F12 (Biochrom; #FG 4815 with stabile Glutamine), FCS 10% final (Biochrom; #S 0415); SK-MEL-3: McCoy's 5A (Biochrom; #F 1015), FCS 10% final (Biochrom; #S 0415), L-Alanyl-L-Glutamine final: 2 mM, (Biochrom; #K 0302)); IGR37 DMEM; (Biochrom; #FG 0445, high glucose; +FCS 10% final (Biochrom; #S 0415); H4 DMEM Gibco #31966-047+ FCS 10% final (Biochrom; #S 0415); PFSK RPMI-1640 Medium+FCS 10% final (Biochrom; #S 0415); DBTRG05MG RPMI 1640; (Biochrom; #FG 1215; +FCS 10% final (Biochrom; #S 0415); DKMG RPMI-1640 Medium+FCS 10% final (Biochrom; #S 0415); GB1 DMEM Gibco #31966-047+ FCS 10% final (Biochrom; #S 0415); SW1783 DMEM/Ham's F12; (Biochrom; #FG 4815; +FCS 10% final (Biochrom; #S 0415); M059J DMEM/Ham's F12;

(Biochrom; #FG 4815+ FCS 10% final (Biochrom; #S 0415); 42-MG-BA RPMI 1640 (50%); (Biochrom; #FG 1215)+MEM Earle's (50%); (Biochrom; #FG 0325); GAMG DMEM high glucose with GlutaMAX (Gibco #31966-021)+Calf Serum Superior (final: 10%); (Biochrom; #S 0615); LN229 DMEM; (Biochrom; #FG 0445, FCS Superior (final: 5%); (Biochrom; #S 0615) L-Alanyl-L-Glutamin; (2 mM extra for final 4 mM, Biochrom, #K 0302); T98G DMEM; (Biochrom; #FG 0445, high glucose; +FCS 10% final (Biochrom; #S 0415); U118-MG DMEM; (Biochrom; #FG 0435; +FCS 10% final (Biochrom; #S 0415); U-251MG RPMI-1640 Medium+FCS 10% final (Biochrom; #S 0415); YKG1 DMEM; (Biochrom; #FG 0435; +FCS 10% final (Biochrom; #S 0415); 92.1 RPMI-1640 Medium+FCS 10% final (Biochrom; #S 0415); Mel202 RPMI-1640 Medium+FCS 10% final (Biochrom; #S 0415); and incubated at 37° C. overnight. After 24 h, cells on one plate (0 h plate) were treated with 30 µl/cavity of CTG solution (Promega Cell Titer Glo (catalogue #G755B and G756B)) and incubated at room temperature for 10 min, and luminescence was measured by means of a VICTOR V (Perkin Elmer), in order to determine cell viability on commencement of treatment. The cells on the test plate were treated with the compounds of the general formula (I) as and incubated at 37° C. for 72 h. The compounds were added to the cells by means of an HP D300 digital dispenser in a 10-step 2,5-fold dilution series generally starting at a maximum final drug concentration of 100 nM, or 30 µM in the case of COV318. As control, the cells were treated with vehicle (DMSO at 0.3% final concentration). After 72 h, the cells were treated with 30 µl/cavity of CTG solution (Promega Cell Titer Glo (catalogue #G755B and G756B)) and incubated at room temperature for 10 min, and luminescence was measured by means of a VICTOR V (Perkin Elmer), in order to determine cell viability at the end of treatment. The percentage effect on cell growth and the IC50 derived therefrom were determined for each test substance using the values from the 0 h plate (=maximum inhibition) and the DMSO control (=minimum inhibition). The IC50 values were calculated using a 4-parameter fit.

TABLE 2

Anti-proliferation $IC_{50}$ values of several examples in vitro in different cell lines

| Example | HeLa $IC_{50}$ [nM] | SK-MEL-3 $IC_{50}$ [nM] |
|---|---|---|
| 1 | 1.5 | 4 |
| 2 | 0.7 | 0.3 |
| 3 | 0.1 | 0.3 |
| 4 | 0.1 | 0.4 |
| 5 | 0.2 | 0.6 |
| 6 | 0.3 | 0.7 |

TABLE 3

Anti-proliferation $IC_{50}$ values of Example 1 in vitro in additional cell lines

| Cell line | tissue | $IC_{50}$ [nM] |
|---|---|---|
| IGR37 | Melanoma | 4.01 |
| H4 | Brain (Astrocytoma) | 47.7 |
| PFSK | Brain (Primitive neuroectodermal tumor) | 2.95 |
| DBTRG05MG | Brain (Glioblastoma) | 30.5 |
| DKMG | Brain (Glioblastoma) | 16.6 |

TABLE 3-continued

Anti-proliferation $IC_{50}$ values of Example 1 in vitro in additional cell lines

| Cell line | tissue | $IC_{50}$ [nM] |
|---|---|---|
| GB1 | Brain (Glioblastoma) | 8.96 |
| SW1783 | Brain (Anaplastic astrocytoma) | >100 |
| M059J | Brain (Glioblastoma) | 40.5 |
| 42-MG-BA | Brain (Glioblastoma) | >100 |
| GAMG | Brain (Glioblastoma) | >100 |
| LN229 | Brain (Glioblastoma) | >100 |
| T98G | Brain (Glioblastoma) | >100 |
| U118-MG | Brain (Glioblastoma: Astrocytoma) | >100 |
| U-251MG | Brain (Glioblastoma: Astrocytoma) | >100 |
| YKG1 | Brain (Glioblastoma) | >100 |
| 92.1 | Uveal melanoma | 19.4 |
| Mel202 | Uveal melanoma | 74.2 |
| COV318 | Ovarian cancer | 8930 |

Thus one aspect of the invention is the use of the compounds of formula (I) for the treatment of cervical cancer.

Another aspect of the invention is the use of the compounds of formula (I) for the treatment of skin cancer, especially melanoma.

Thus one aspect of the invention is the use of the compounds of formula (I) for the treatment of brain cancer, especially glioblastoma, astrocytoma, anaplastic astrocytoma, primitive neuroectodermal tumor.

Yet another aspect of the invention is the use of compounds of formula (I), for the treatment of skin cancer, especially melanoma, cervical cancer and ovarian cancer.

Yet another aspect of the invention is the use of compounds of formula (I), for the treatment of skin cancer, especially melanoma, brain cancer, cervical cancer and ovarian cancer.

Another aspect are compounds of formula (I) which effectively inhibit tumor cell proliferation (e.g. in HeLa cells) with $IC_{50}$ values of <100 nM.

Another aspect are compounds of formula (I) which effectively inhibit tumor cell proliferation (e.g. in HeLa cells) with $IC_{50}$ values of <10 nM.

Assay 2
Method for PDE3A Enzyme Inhibition

The commercially available 3H-cAMP Scintillation Proximity Assay (SPA, Perkin Elmer) system was used for enzyme inhibition studies. For the determination of the in vitro effect of example compounds on the PDE3A reactions 2 µl of the respective example compound solution in DMSO (serial dilutions) were placed in wells of microtiter plates (Isoplate-96/200W; Perkin Elmer). 50 µl of a dilution of PDE3A cell extract from Sf9 cells overexpressing human full length PDE3A (SB Drug Discovery, UK) in buffer A (50 mM Tris/HCl pH 7.5, 8.3 mM $MgCl_2$, 1.7 mM EDTA, 0.2% BSA) was added. The dilution of the PDE3A cell extract was chosen such that the reaction kinetics was linear and less than 70% of the substrate was consumed (typical dilution 1:5000). The reaction was started by addition of 50 µl (0.025 µCi) of 1:2000 in buffer A w/o BSA diluted substrate [8-3H] adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). $IC_{50}$ values were determined from sigmoidal curves by plotting percentage PDE3A activity vs log compound concentration.

Assay 3
PDE3B Enzyme Inhibition

The commercially available 3H-cAMP Scintillation Proximity Assay (SPA, Perkin Elmer) system was used for enzyme inhibition studies. For the determination of the in vitro effect of example compounds on the PDE3B reactions 2 µl of the respective example compound solution in DMSO (serial dilutions) were placed in wells of microtiter plates (Isoplate-96/200W; Perkin Elmer). 50 µl of a dilution of PDE3B cell extract from Sf9 cells overexpressing human full length PDE3B (SB Drug Discovery, UK) in buffer A (50 mM Tris/HCl pH 7.5, 8.3 mM $MgCl_2$, 1.7 mM EDTA, 0.2% BSA) was added. The dilution of the PDE3B cell extract was chosen such that the reaction kinetics was linear and less than 70% of the substrate was consumed (typical dilution 1:6000). The reaction was started by addition of 50 µl (0.025 µCi) of 1:2000 in buffer A w/o BSA diluted substrate [8-3H] adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC50 values were determined from sigmoidal curves by plotting percentage PDE3B activity vs log compound concentration. Inhibitory activity for Examples 1-6 are shown in Table 4.

One-aspect of the invention are compounds of formula (I) which effectively inhibit tumor cell proliferation with $IC_{50}$ values of <100 nM in e.g. HeLa cells while $IC_{50}$ values for enzymatic PDE3A or PDE3B inhibition are often >10 times higher than $IC_{50}$ values for tumor cell proliferation.

Another aspect of the invention are compounds of formula (I) which effectively inhibit tumor cell proliferation with $IC_{50}$ values of <100 nM in e.g. HeLa cells while $IC_{50}$ values for enzymatic PDE3A or PDE3B inhibition are often >30 times higher than $IC_{50}$ values for tumor cell proliferation.

Another aspect of the invention are compounds of formula (I) which effectively inhibit tumor cell proliferation with $IC_{50}$ values of <10 nM in e.g. HeLa cells while $IC_{50}$ values for enzymatic PDE3A or PDE3B inhibition are often >30 times higher than $IC_{50}$ values for tumor cell proliferation.

TABLE 4

Inhibition of PDE3A and PDE3B

| Example | PDE3A $IC_{50}$ [nM] | PDE3B $IC_{50}$ [nM] |
| --- | --- | --- |
| 1 | 91 | 81 |
| 2 | 5 | 6 |
| 3 | 2 | 1 |
| 4 | 2 | 1 |
| 5 | 4 | 5 |
| 6 | 4 | 5 |

Assay 4
In Vivo Pharmacokinetics in Mice, Rats, Dogs and Monkeys

For in vivo pharmacokinetic experiments test compounds were administered to female CD-1 mice, male Wistar rats, Beagle dogs or Cynomolgus monkeys intravenously at doses of 0.3 to 1 mg/kg formulated as solutions using solubilizers such as PEG400 in well-tolerated amounts.

Studies may also have been performed as cassette administrations of up to 3 compounds given together simultaneously in low doses.

For pharmacokinetics after intravenous administration test compounds were given in the female mice and male rat as i.v. bolus and in dogs and monkeys as short term infusion (15 min). Blood samples were taken e.g. at 2 min, 8 min, 15 min, 30 min, 45 min, 1 h, 2 h, 4 h, 6 h, 8 h and 24 h after dosing from the vena jugularis (mouse, rat) or vena saphena (dog, monkey). Blood was collected into Lithium-Heparin-tubes (Monovetten®, Sarstedt) and centrifuged for 15 min at 3000 rpm. An aliquot of 100 µL from the supernatant (plasma) was taken and precipitated by addition of 400 µL cold acetonitril and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software (e.g. Phoenix WinNonlin®, Certara USA, Inc.).

PK parameters derived from concentration-time profiles after i.v.: CLplasma (in L/kg/h): Total plasma clearance of test compound calculated by dose (in µg/kg) divided by area under the concentration-time curve from t=0 h to infinity (extrapolated) (AUCinf in µg*h/L); CLblood: Total blood clearance of test compound: CLplasma*Cp/Cb (in L/kg/h) with Cp/Cb being the ratio of test compound concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h).

Pharmacokinetics describe the time course of drug concentration in the body, CLblood (CLb) is an important pharmacokinetic property of drugs. Preferred examples of the present invention show a CLb of ≤1.6 L/h/kg, ≤1.3 L/h/kg, ≤0.6 L/h/kg and ≤0.8 L/h/kg in mice, rat, dog & monkey, respectively. Results for Example 1 ((5S)-5-methyl-6-{3-(trifluoromethyl)-4-[3-(trifluoromethyl)-1H-pyrazol-1-yl]phenyl}-4,5-dihydro-1,2,4-triazin-3(2H)-one) administration are shown in Table 5.

TABLE 5

| Example | Species/Sex/Strain | Formulation | Dose | CLblood |
| --- | --- | --- | --- | --- |
| Example 1 | Mouse/female/CD1 | PEG400 60% + Water 35% + EtOH 5% | 0.5 mg/kg | 0.18 L/h/kg |
| Example 1 | Rat/male/Wistar | Plasma 95% + EtOH 4% + DMSO 1% | 0.5 mg/kg | 0.22 L/h/kg |
| Example 1 | Dog/female/Beagle | PEG400 50% + Water 40% + EtOH 10% | 0.3 mg/kg | 0.27 L/h/kg |

Assay 5
Validation of PDE3A Modulator-Induced PDE3A Protein Interactions Using Immunoprecipitation and Immunoblotting HeLa cells can be transfected with ORF overexpression constructs expressing V5-tagged SLFN12, or V5-tagged GFP. ORF expression constructs can be obtained from the TRC (clone IDs: TRCN0000468231, TRCN0000476272, ccsbBroad304_99997). At 72 hours post transfection, cells can be treated with 10 µM DNMDP or trequinsin for 4 hours followed by lysis using the ModRipa lysis buffer and immunoprecipitation of PDE3A. For each condition, 2 mg total protein lysate can be incubated with 1 μg of anti-PDE3A antibody at 4° C. overnight, after which 7.5 μl each of Protein A- and Protein G-Dynabeads (Life Technologies 10001D and 10003D) can be added and incubated for another 1 hour. Beads can be washed and bound proteins can be eluted with 30 μl of LDS PAGE gel loading buffer. Input (~60 μg total protein lysate) and IP products can be resolved on 4-12% Tris-Glycine PAGE gels and can be immunoblotted with an anti-V5 antibody (Life Technologies R96205, 1:5000), the Bethyl anti-PDE3A antibody (1:1000), and secondary antibodies from LiCOR Biosciences (Cat. #926-32210 and 926068021, each at 1:10,000). Blots can be washed and imaged using a LiCOR Odyssey infrared imager.

Assay 6
In Vivo Xenotransplantation Models

The anti-tumor activity of Example 1, ((5S)-5-methyl-6-{3-(trifluoromethyl)-4-[3-(trifluoromethyl)-1H-pyrazol-1-yl]phenyl}-4,5-dihydro-1,2,4-triazin-3(2H)-one), was examined in murine xenotransplantation models of human cancer. For this purpose, mice were implanted subcutaneously with tumor cells. At a mean tumor size of 20-40 mm² animals were randomized into treatment and control groups (at least n=10 animals/group) and treatment started with vehicle only or Example 1 (formulation: 90% PEG400/10% Ethanol; application route: per os ("p.o."), orally). The oral application volume was 10 ml/kg. In the case of twice daily treatments, the time interval between two applications per day was 6-7 h. The tumor size and the body weight were determined at least weekly. The tumor area was detected by means of an electronic caliper [length (mm)×width (mm)]. The experiment was ended when the tumors of the vehicle control reached the pre-determined ethical endpoint based on German and European animal welfare regulations. In vivo anti-tumor efficacy is presented as T/C ratio at study end (Treatment/Control; mean tumor area or weight of treatment group/mean tumor area or weight of control group) in Table 7. A compound having a T/C below 0.5 is defined as active (i.e., effective). Statistical analysis was assessed using SigmaStat software. A one-way analysis of variance was performed and differences to the control were compared by a pair-wise comparison procedure (Dunn's method).

Results:

Example 1 showed potent anti-tumor efficacy in a xenograft model of human tumors upon monotherapy treatment. Specifically, Example 1 was effective in reduction of tumor area in melanoma.

Anti-tumor activity of Example 1 in human cancer xenograft models in mice is shown in Table 6.

TABLE 6

| Xenograft Model | Indication | Dose and schedule | T/C |
|---|---|---|---|
| IGR-37 | Melanoma | 4 mg/kg 2QD p.o. | 0.06 * |
| IGR-37 | Melanoma | 4 mg/kg QD p.o. | 0.07 * |
| IGR-37 | Melanoma | 2 mg/kg 2QD p.o. | 0.06 * |
| IGR-37 | Melanoma | 1 mg/kg 2QD p.o. | 0.06 * |

* P < 0.05 treatment vs control at study end
T/C = ratio of mean final tumor weight of treatment group versus mean final tumor weight of control group The abbreviation 2QD means twice per day, p.o. means per os or-oral.

Assay 7
Effects on Cardiovascular Function in Conscious Telemetered Rats

The measurement of cardiovascular parameters in small laboratory animals such as the rat by telemetry is an integral part of cardiac safety assessment. The telemetry technology provides precise measurements while avoiding stress artifacts inherent with the use of physical or chemical restraint and is suitable to detect potential drug-induced alterations of cardiovascular parameters.

Conscious telemetered normotensive Wistar rats (n=4-6/group) are treated with single doses of a compound (three dose groups and a vehicle control group). Cardiovascular parameters such as arterial systolic and diastolic blood pressure, heart rate, left ventricular systolic and end diastolic pressure, left ventricular contractility, as well as body temperature and locomotor activity are continuously monitored before and over 24 hours after administration. For statistical analysis of cardiovascular parameters a mixed model approach and a Dunnett's t-test procedure is used.

A compound of formula (I) not causing substantial effects on cardiovascular parameters is preferred.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The invention claimed is:
1. A compound of formula (I)

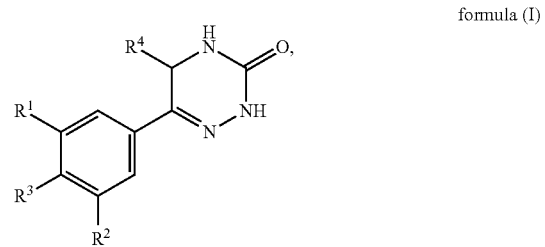

formula (I)

wherein
R¹ is a hydrogen atom, a halogen atom, a $C_1$-$C_3$-alkyl group, or a $C_1$-$C_3$-haloalkyl group;
R² is a hydrogen atom, or a halogen atom;
with the proviso that both, R¹ and R², may not be a hydrogen atom at the same time with the exception if R³ is an ortho substituted phenyl group, both, R¹ and R², may also be a hydrogen atom;
R³ is
a $C_1$-$C_3$-alkyl group which is substituted one or more times with a group independently selected from a $C_1$-$C_3$-alkyl group, a $C_1$-$C_3$-alkoxy group, a heterocycloalkyl group, and an amino group which is substituted once or twice with a $C_1$-$C_3$-alkyl group,
a $C_2$-$C_6$-alkenyl group, which is optionally substituted with a $C_1$-$C_3$-alkoxy group,
a $C_5$-$C_6$-cycloalkenyl group, a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

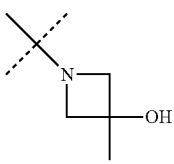

group, a

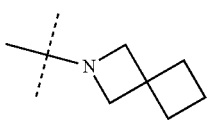

group, a

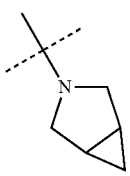

group, a 5- to 10-membered heteroaryl group which is substituted one or more times with a group independently selected from an amino group, a halogen atom, and a $C_1$-$C_3$-haloalkyl group, a $C_1$-$C_6$-alkoxy group which is optionally substituted with a group independently selected from $C_1$-$C_3$-haloalkyl group, a hydroxy group, a $C_1$-$C_3$-alkyoxy group, a $C_4$-$C_6$-cycloalkyl group, a 4- to 6-membered heterocycloalkyl group, a 5- to 6-membered heteroaryl group, with the proviso that an unsubstituted methoxy group is excluded;

a $NR^5R^6$ group, and a

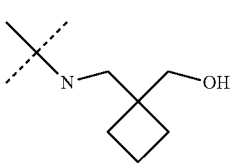

group, $R^4$ is a hydrogen atom or a $C_1$-$C_3$-alkyl group;

$R^5$ is a hydrogen atom $R^6$ is selected from a $C_1$-$C_3$-alkyl group which is substituted one or more times with a group selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group, and a $C_5$-$C_6$-cycloalkyl group;

or a stereoisomer, a tautomer, an N-oxide, or a salt thereof, or a salt of a stereoisomer, a salt of a tautomer, a salt of an N-oxide or a mixture of same.

2. The compound according to claim 1, wherein:

$R^1$ is a hydrogen atom, a halogen atom, a $C_1$-$C_3$-alkyl group, or a $C_1$-$C_3$-haloalkyl group;

$R^2$ is a hydrogen atom, or a halogen atom;

with the proviso that both, $R^1$ and $R^2$, may not be a hydrogen atom at the same time $R^3$ is a phenyl group which is substituted one or more times with a group independently selected from halogen atom, $C_1$-$C_3$-alkyl group, and a $C_1$-$C_3$-haloalkyl group, a 4- to 6-membered heterocycloalkyl group which is substituted one or more times with a group independently selected from a fluorine atom, a hydroxy group, and a $C_1$-$C_3$-alkyl group, a

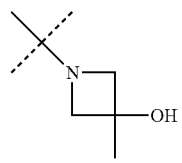

group, a

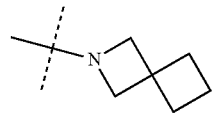

group, a

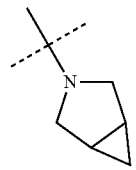

group, a 5- to 10-membered heteroaryl group which is substituted one or more times with a group independently selected from an amino group, a chlorine atom, a fluorine atom, a trifluormethyl group, and a difluoromethyl group,
a NR⁵R⁶ group, and
a

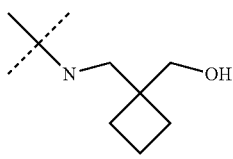

group,
R⁴ is a hydrogen atom or a $C_1$-$C_3$-alkyl group;
R⁵ is a hydrogen atom
R⁶ is selected from
a $C_1$-$C_3$-alkyl group which is substituted one or more times with a group selected from a 5- to 6-membered heteroaryl group, a $C_1$-$C_3$-alkoxy group, a hydroxy group, a $C_1$-$C_3$-haloalkyl group, and a $C_4$-$C_6$-cycloalkyl group which itself is optionally substituted with a $C_1$-$C_3$-hydroxyalkyl group,
and
a $C_5$-$C_6$-cycloalkyl group;
or a stereoisomer, a tautomer, an N-oxide, or a salt thereof, or a salt of a stereoisomer, a salt of a tautomer, a salt of an N-oxide or a mixture of same.

3. The compound according to claim 1, wherein:
R¹ is a hydrogen atom, a fluorine atom, a chlorine atom, a methyl group, or a trifluoromethyl group;
R² is a hydrogen atom, a fluorine atom, or a chlorine atom; with the proviso that both, R¹ and R², may not be a hydrogen atom at the same time;
R³ is selected from a —(CH₂)—CH(CH₃)₂ group, a —(CH₂)₃—O—CH₃ group, a —CH₂-(morpholin-4-yl) group, a —CH₂—N(CH₃)₂ group,
a —CH=C(CH₃)₂ group, a —CH=CH—CH₂—O—CH₃ group, a —CH=CH—CH₂—O—CH₂—CH₃ group,
a cyclopent-1-en-1-yl group,
a 4-chlorophenyl group, a 4-fluoro-phenyl group, a 4-fluoro-2-methyl-phenyl group, a 3-fluoro-4-methyl-phenyl group, a 4-fluoro-2-trifluoromethyl-phenyl group,
a piperidin1-yl group, a 3-hydroxy-piperidin-1-yl group, a 4,4-difluoro-piperidin-1-yl group,
a 4-ethyl-4-hydroxy-piperidin-1-yl group, a

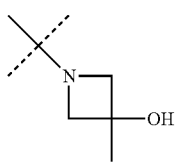

group, a

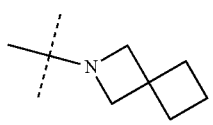

group, a

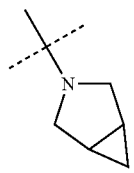

group, a 3-hydroxy-3-methyl-pyrrolidin-1-yl group, a 4-methyl-piperazin-1-yl group, a morpholin-4-yl group,
a pyridin-4-yl group, a 2-amino-pyridin-4-yl group, a 3-chloro-pyridin-6-yl group, a 3-fluoro-pyrazol-1-yl group, a 3-trifluoromethyl-pyrazol-1-yl group, a 1-difluoromethylpyrazol-4-yl group, a 4-trifluoromethyl-1,2,3-triazol-2-yl group,
a —NH—CH₂-(pyrazol-3-yl) group, a —NH—CH₂-(pyrazol-5-yl) group, a —NH—CH₂-pyrazin-2-yl group, a —NH—(CH₂)₂—O—CH₃ group, a —NH—CH₂—CH(OH)CF₃ group, a

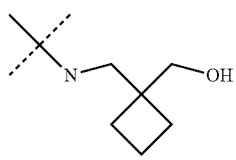

group, a NH-cyclopentyl group,
a —O—(CH₂)₂—CH₃ group, a —O—(CH₂)₂—C(CH₃)₃ group, a —O—(CH₂)—CH(CH₃)—OH group, a —O—(CH₂)—C(CH₃)₂—OH group, a —O—CH₂-(pyrazol-3-yl) group, a —O—(CH₂)₂—O—CH₃ group, a —O—CH₂-cyclobutyl group, a —O—CH₂-tetrahydofuran-2-yl group, a —O—(CH₂)₂—CF₃ group, and a —O—(CH₂)₃CH₃ group,
R⁴ is a hydrogen atom or a methyl group;
or a stereoisomer, a tautomer, an N-oxide, or a salt thereof, or a salt of a stereoisomer, a salt of a tautomer, a salt of an N-oxide or a mixture of same.

4. The compound according to claim 1, wherein:
R¹ is a hydrogen atom, a fluorine atom, a chlorine atom, a methyl group, or a trifluoromethyl group,
R² is a hydrogen atom, a fluorine atom, or a chlorine atom, with the proviso that both, R¹ and R², may not be a hydrogen atom at the same time;
R³ is selected from
a 5- to 6-membered heteroaryl group, which is substituted with a trifluoromethyl group,
a 4- to 6-membered heterocycloalkyl group, which is substituted with a hydroxy group or a $C_1$-$C_3$-alkyl group,
a $C_4$-$C_6$-heterocycloalkyl group which is optionally substituted with one or two groups selected from a $C_1$-$C_3$-alkyl group and a hydroxy group,
and
a NR⁵R⁶ group
R⁴ is a methyl group;
R⁵ is a hydrogen atom;
R⁶ is
an $C_1$-$C_3$-alkyl group which itself is substituted one or more times with a group independently selected from a heteroaryl group, a $C_1$-$C_3$-haloalkyl group, and a hydroxy group, and a $C_5$-$C_6$-cycloalkyl group, or a stereoisomer, a tautomer, an N-oxide, or a salt thereof, or a salt of a stereoisomer, a salt of a tautomer, a salt of an N-oxide or a mixture of same.

5. The compound according to claim 1, wherein:

$R^1$ is a trifluormethyl group;

$R^2$ is; a hydrogen atom $R^3$ is selected from a —NH—CH$_2$—CH(OH)CF$_3$ group, a —NH-cyclopentyl group, a —NH—CH$_2$-(pyrazol-5-yl) group, a —NH—CH$_2$-pyrazin-2-yl group, a 3-hydroxy-3-methyl-azetidin-1-yl group, and a 3-trifluoromethyl-pyrazol-1-yl group, and $R^4$ is a methyl group;

or a stereoisomer, a tautomer, an N-oxide, or a salt thereof, or a salt of a stereoisomer, a salt of a tautomer, a salt of an N-oxide or a mixture of same.

6. The compound according to claim 1 which is selected from:

(5S)-5-methyl-6-{3-(trifluoromethyl)-4-[3-(trifluoromethyl)-1H-pyrazol-1-yl]phenyl}-4,5-dihydro-1,2,4-triazin-3 (2H)-one (5S)-5-methyl-6-[4-{[(1H-pyrazol-5-yl)methyl]amino}-3-(trifluoromethyl)phenyl]-4,5-dihydro-1,2,4-triazin-3 (2H)-one (5S)-6-[4-(3-hydroxy-3-methylazetidin-1-yl)-3-(trifluoromethyl)phenyl]-5-methyl-4,5-dihydro-1,2,4-triazin-3 (2H)-one (5S)-6-[4-(cyclopentylamino)-3-(trifluoromethyl)phenyl]-5-methyl-4,5-dihydro-1,2,4-triazin-3 (2H)-one (5S)-5-methyl-6-[4-{[(2R)-3,3,3-trifluoro-2-hydroxypropyl]amino}-3-(trifluoromethyl)phenyl]-4,5-dihydro-1,2,4-triazin-3 (2H)-one (5S)-5-methyl-6-[4-{[(pyrazin-2-yl)methyl]amino}-3-(trifluoromethyl)phenyl]-4,5-dihydro-1,2,4-triazin-3 (2H)-one or a stereoisomer, a tautomer, an N-oxide, or a salt thereof, or a salt of a stereoisomer, a salt of a tautomer, a salt of an N-oxide or a mixture of same.

7. A pharmaceutical composition comprising a compound of general formula (I) according to claim 1 and one or more pharmaceutically acceptable excipients.

8. A pharmaceutical combination comprising:

one or more first active ingredients, in particular compounds of general formula (I) according to claim 1, and one or more further active ingredients.

* * * * *